(12) United States Patent
Nik-Zainal et al.

(10) Patent No.: US 12,062,416 B2
(45) Date of Patent: *Aug. 13, 2024

(54) METHOD OF CHARACTERIZING A DNA SAMPLE

(71) Applicant: GENOME RESEARCH LIMITED, Hinxton (GB)

(72) Inventors: Serena Nik-Zainal, Hinxton (GB); Helen Davies, Hinxton (GB); Dominik Glodzik, Hinxton (GB); Sandro Morganella, Hinxton (GB)

(73) Assignee: Genome Research Limited, Hinxton (GB)

( * ) Notice: Subject to any disclaimer, the term of this patent is extended or adjusted under 35 U.S.C. 154(b) by 1333 days.

This patent is subject to a terminal disclaimer.

(21) Appl. No.: 16/096,731

(22) PCT Filed: Apr. 28, 2017

(86) PCT No.: PCT/EP2017/060298
§ 371 (c)(1),
(2) Date: Oct. 26, 2018

(87) PCT Pub. No.: WO2017/191076
PCT Pub. Date: Nov. 9, 2017

(65) Prior Publication Data
US 2019/0130997 A1 May 2, 2019

(30) Foreign Application Priority Data

May 1, 2016 (GB) .................................. 1607635
Mar. 10, 2017 (GB) .................................. 1703903

(51) Int. Cl.
G16B 25/10 (2019.01)
C12Q 1/6809 (2018.01)
G16B 20/00 (2019.01)
G16B 20/10 (2019.01)
G16B 20/20 (2019.01)
G16B 20/40 (2019.01)
G16B 40/30 (2019.01)

(52) U.S. Cl.
CPC ........... *G16B 25/10* (2019.02); *C12Q 1/6809* (2013.01); *G16B 20/00* (2019.02); *G16B 20/10* (2019.02); *G16B 20/20* (2019.02); *G16B 20/40* (2019.02); *G16B 40/30* (2019.02)

(58) Field of Classification Search
CPC ........ G16B 25/10; G16B 20/20; G16B 40/30; G16B 20/00
See application file for complete search history.

(56) References Cited

U.S. PATENT DOCUMENTS

| | | |
|---|---|---|
| 7,097,977 B1 | 8/2006 | Takeda et al. |
| 2012/0035244 A1 | 2/2012 | Chinnaiyan et al. |
| 2013/0281312 A1 | 10/2013 | Richardson et al. |
| 2014/0278135 A1 | 9/2014 | Pruss et al. |
| 2014/0363521 A1 | 12/2014 | Abkevich et al. |
| 2014/0364434 A1 | 12/2014 | Daeman et al. |
| 2019/0115105 A1 | 4/2019 | Liu et al. |
| 2019/0119759 A1 | 4/2019 | Nik-Zainal et al. |
| 2019/0139625 A1 | 5/2019 | Nik-Zainal et al. |
| 2020/0126635 A1 | 4/2020 | Nik-Zainal et al. |

FOREIGN PATENT DOCUMENTS

| | | | |
|---|---|---|---|
| CN | 1976711 A | 6/2007 | |
| CN | 101490553 A | 7/2009 | |
| EP | 3452938 | 3/2019 | |
| JP | 2010-506939 A | 3/2010 | |
| JP | 2013-537045 A | 9/2013 | |
| JP | 2014-532859 A | 12/2014 | |
| JP | 2015/506678 A | 3/2015 | |
| WO | WO-02/06481 A1 | 1/2002 | |
| WO | 2008/016374 A2 | 2/2008 | |
| WO | WO-2008016374 A2 * | 2/2008 | ........... C12Q 1/6883 |
| WO | WO-2013/096843 A1 | 6/2013 | |
| WO | WO 2013/130347 A1 | 9/2013 | |
| WO | WO-2013/182645 A1 | 12/2013 | |
| WO | WO-2013/190441 A2 | 12/2013 | |
| WO | WO-2015/086473 A1 | 6/2015 | |
| WO | WO 2016/025958 A1 | 2/2016 | |
| WO | WO-2017/191068 A1 | 11/2017 | |
| WO | WO-2017/191073 A1 | 11/2017 | |

(Continued)

OTHER PUBLICATIONS

Stratton, Exploring the Genomes of Cancer Cells: Progress and Promise, 2011, Science, 331, p. 1553-1558 (Year: 2011).*
Garassino, Personalised Cancer Medicine: An ESMO Guide for Patients, 2013, ESMO, p. 1-46 (Year: 2013).*
Helleday et al., Mechanisms underlying mutational signatures in human cancers, 2014, Nature Reviews Genetics, 15, p. 585-598 (Year: 2014).*
Telli et al., Homologous Recombination Deficiency (HRD) Score Predicts Response to Platinum-Containing Neoadjuvant Chemotherapy in Patients with Triple-Negative Breast Cancers, 2016, Clin Cancer Res, 22(15), p. 3764-3773 (Year: 2016).*
Timms et al., Association of BRCA1/2 defects with genomic scores predictive of DNA damage repair deficiency among breast cancer subtypes, 2014, Breast Cancer Research, 16:475, p. 1-9, suppl. (Year: 2014).*

(Continued)

*Primary Examiner* — Kaitlyn L Minchella
(74) *Attorney, Agent, or Firm* — Wolf, Greenfield & Sacks, P.C.

(57) ABSTRACT

The present invention provides methods of characterising a DNA sample obtained from a tumour to produce an interpreted profile of the tumour based on a combination of a range of tests on the tumour, the tests including a selection from: determining a catalogue of base substitution signatures which are present in the sample; determining a catalogue of rearrangement signatures which are present in the sample; determining a catalogue of insertion/deletion signatures which are present in the sample; determining the overall copy number profile in the sample and identifying putative driver mutations present in the sample.

13 Claims, 37 Drawing Sheets

(56) References Cited

FOREIGN PATENT DOCUMENTS

| WO | WO-2017/191074 A1 | 11/2017 |
|---|---|---|
| WO | WO-2017/191076 A1 | 11/2017 |

OTHER PUBLICATIONS

Abkevich et al., Patterns of genomic loss of heterozygosity predict homologous recombination repair defects in epithelial ovarian cancer; 2012 British Journal of Cancer, 107, p. 1776-1782 (Year: 2012).*
Piraino et al., Beyond the exome: the role of non-coding somatic mutations in cancer, 2016, Annals of Oncology, 27, p. 240-248 (Year: 2016).*
Volleberg et al., "Genomic instability in breast and ovarian cancers: translation into clinical predictive biomarkers," Cell Mol Life Sci. 69(2):223-45 (2012).
Combined Search and Examination Report Under Sections 17 and 18(3) for British Application No. 1706944.4, dated Feb. 8, 2018 (8 pages).
Office Action for Japanese Patent Application No. 2018-557362, dated Aug. 3, 2021.
Nik-Zainal et al., "Mutational processes molding the genomes of 21 breast cancers," Cell. 149(5):979-93 (2012).
Notice of Reasons for Rejection and English Translation for Japanese Patent Application No. 2019-508296, mailed Apr. 13, 2021 (5 pages).
Abkevich et al., "Patterns of genomic loss of heterozygosity predict homologous recombination repair defects in epithelial ovarian cancer," Br J Cancer. 107(10):1776-1782 (2012).
Abkevich et al., "Supplementary Material for: Patterns of Genomic Loss of Heterozygosity Predict Homologous Recombination Repair Defects in Epithelial Ovarian Cancer," Br J Cancer. (2012) (20 pages).
Alexandrov et al., "A mutational signature in gastric cancer suggests therapeutic strategies," Nat Commun. 6:8683 (2015) (7 pages).
Alexandrov et al., "Clock-like mutational processes in human somatic cells," Nat Genet. 47(12):1402-1407, doi: 10.1038/ng.3441 (2015) (9 pages).
Alexandrov et al., "Deciphering Signatures of Mutational Processes Operative in Human Cancer," Cell Rep. 3(1):246-59 (2013).
Alexandrov, Ludmil B., Thesis: "Signatures of Mutational Processes in Human Cancer," Doctor of Philosophy, Darwin College, University of Cambridge, 2014 (247 pages).
Chan et al., "Clusters of Multiple Mutations: Incidence and Molecular Mechanisms," available in PMC Jan. 12, 2016, published in final edited form as: Annu Rev Genet. 49:243-67 (2015) (32 pages).
International Preliminary Report on Patentability for International Application No. PCT/EP2017/060279, issued Nov. 6, 2018 (7 pages).
International Preliminary Report on Patentability for International Application No. PCT/EP2017/060289, issued Nov. 6, 2018 (9 pages).
International Preliminary Report on Patentability for International Application No. PCT/EP2017/060294, issued Nov. 6, 2018 (10 pages).
International Preliminary Report on Patentability for International Application No. PCT/EP2017/060298, issued Nov. 6, 2018 (8 pages).
International Search Report and Written Opinion for International Application No. PCT/EP2017/060279, mailed Aug. 31, 2017 (10 pages).
International Search Report and Written Opinion for International Application No. PCT/EP2017/060289, mailed Jul. 17, 2017 (12 pages).
International Search Report and Written Opinion for International Application No. PCT/EP2017/060294, mailed Jul. 31, 2017 (15 pages).
International Search Report and Written Opinion for International Application No. PCT/EP2017/060298, mailed Aug. 2, 2017 (12 pages).
Malhotra et al., "Breakpoint profiling of 64 cancer genomes reveals numerous complex rearrangements spawned by homology-independent mechanisms," Genome Research. 23(5): 762-776 (2013) (17 Pages).
Menghi et al., "The tandem duplicator phenotype as a distinct genomic configuration in cancer," Proc Natl Acad Sci USA. 113(17):E2373-E2382 (2016).
Nik-Zainal et al., "Landscape of somatic mutations in 560 breast cancer whole genome sequences," available in PMC Nov. 2, 2016, published in final edited form as: Nature. 534(7605):47-54 (2016) (40 pages).
Nik-Zainal, Serena, Thesis: "Exploring mutational signatures in twenty-one breast cancers," Doctor of Philosophy, University of Cambridge, 2012 (235 pages).
Pleasance et al., "A small-cell lung cancer genome with complex signatures of tobacco exposure," Nature. 463(7278): 184-190 (2009) (9 Pages).
Schulze et al., "Exome sequencing of hepatocellular carcinomas identifies new mutational signatures and potential therapeutic targets," available in PMC Nov. 1, 2015, published in final edited form as: Nature Genet. 47(5):505-11 (2015) (22 pages).
Waddell et al., "Whole genomes redefine the mutational landscape of pancreatic cancer," Nature. 518(7540):495-501 (2015) (19 pages).
Chopra et al., "Homologous recombination DNA repair deficiency and PARP inhibition activity in primary triple negative breast cancer," Nat Commun. 11(1):2662 (2020) (12 pages).
Davies et al., "HRDetect is a predictor of BRCA1 and BRCA2 deficiency based on mutational signatures," available in PMC Mar. 2, 2018 published in final edited form as: Nat Med. 23(4):517-525 (2017) (28 pages).
Degasperi et al., "A practical framework and online tool for mutational signature analyses show intertissue variation and driver dependencies," available in PMC Feb. 28, 2020, published in final edited form as: Nat Cancer. 1(2):249-263 (2020) (45 pages).
Stratton et al., "The cancer genome," Nature. (458)7239:719-24 (2009).
Nik-Zainal et al., "The Life History of 21 Breast Cancers," Cell. 149(5):994-1007 (2012).
Hicks et al., "Novel patterns of genome rearrangement and their association with survival in breast cancer," Genome research. 16(12): 1465-79 (2006).
Bergamaschi et al., "Extracellular matrix signature identifies breast cancer subgroups with different clinical outcome," J Pathol. 214(3):357-67 (2008) (Abstract only) (2 pages).
Ching et al., "Integrated analysis of copy number and loss of heterozygosity in primary breast carcinomas using high-density SNP array," Int J Oncol. 39(3):621-33 (2011).
Fang et al., "Genomic differences between estrogen receptor (ER)-positive and ER-negative human breast carcinoma identified by single nucleotide polymorphism array comparative genome hybridization analysis," available in PMC Jul. 31, 2015 published in final edited form as: Cancer. 117(10):2024-34 (2011) (17 pages).
Curtis et al., "The genomic and transcriptomic architecture of 2,000 breast tumours reveals novel subgroups," available in PMC Dec. 21, 2012, published in final edited form as: Nature. 486(7403):346-52 (2012) (15 pages).
Pleasance et al., "A comprehensive catalogue of somatic mutations from a human cancer genome," available in PMC Jul. 28, 2011, published in final edited form as: Nature. 463(7278):191-6 (2010) (14 pages).
Pleasance et al., "A small-cell lung cancer genome with complex signatures of tobacco exposure," Nature. 463(7278):184-90 (2010) (9 pages).
Banerji et al., "Sequence analysis of mutations and translocations across breast cancer subtypes," available in PMC Aug. 29, 2014, published in final edited form as: Nature. 486(7403):405-9 (2012) (11 pages).
Ellis et al., "Whole-genome analysis informs breast cancer response to aromatase inhibition," available in PMC Dec. 21, 2012, published in final edited form as: Nature. 486(7403):353-60 (2012) (20 pages).

(56) References Cited

OTHER PUBLICATIONS

Shah et al., "The clonal and mutational evolution spectrum of primary triple-negative breast cancers," available in PMC Dec. 16, 2013, published in final edited form as: Nature. 486(7403):395-9 (2012) (13 pages).
Birkbak et al., "Telomeric allelic imbalance indicates defective DNA repair and sensitivity to DNA-damaging agents," available in PMC Oct. 23, 2013, published in final edited form as: Cancer Discov. 2(4):366-375 (2012) (19 pages).
Popova et al., "Ploidy and large-scale genomic instability consistently identify basal-like breast carcinomas with BRCA1/2 inactivation," Cancer Res. 72(21):5454-62 (2012).
Fischer et al., "EMu: probabilistic inference of mutational processes and their localization in the cancer genome," Genome Biol. 14(4):R39 (2013) (10 pages).
Sherry et al., "dbSNP: the NCBI database of genetic variation," Nucleic Acids Res. 29(1):308-11 (2001).
1000 Genomes Project Consortium et al., "An integrated map of genetic variation from 1,092 human genomes," available in PMC May 1, 2013, published in final edited form as: Nature. 491(7422):56-65 (2012) (24 pages).
Fu et al., "Analysis of 6,515 exomes reveals the recent origin of most human protein-coding variants," available in PMC Jul. 10, 2013, published in final edited form as: Nature (493) 7431:216-20 (2013) (11 pages).
Polak et al., "A mutational signature reveals alterations underlying deficient homologous recombination repair in breast cancer," available in PMC Jul. 23, 2020, published in final edited form as: Nat Genet. 49(10):1476-1486 (2017) (22 pages).
Iolascon et al., "Frequent clonal loss of heterozygosity (LOH) in the chromosomal region 1p32 occurs in childhood T cell acute lymphoblastic leukemia (T-ALL) carrying rearrangements of the TAL1 gene," Leukemia. 11(3):359-363 (1997).
Communication pursuant to Article 94(3) EPC for European Patent Application No. 17720779.2, dated Mar. 11, 2022 (6 pages).
Communication pursuant to Article 94(3) EPC for European Patent Application No. 17721610.8, dated Apr. 5, 2022 (8 pages).
Communication pursuant to Article 94(3) EPC for European Application No. 17720140.7, dated Feb. 18, 2022 (7 pages).
Final Rejection for Japanese Application No. 2018-557362, mailed Jul. 5, 2022 (2 pages). English translation included.
Alexandrov, Ludmil B., Thesis. Chapter 2 of "Signatures of Mutational Processes in Human Cancer," Doctor of Philosophy, Darwin College, University of Cambridge, 2014 (247 pages).
Notice of the Second Office Action for Chinese Patent Application No. 201780027340.5, dated Aug. 12, 2022 (15 pages).
Bao et al., "Review of current methods, applications, and data management for the bioinformatics analysis of whole exome sequencing," Cancer Inform. 13(Suppl 2):67-82 (Sep. 21, 2014).
Ayers et al., "SNP selection in genome-wide and candidate gene studies via penalized logistic regression," Genet Epidemiol. 34(8):879-91 (Dec. 2010).
Marquard et al., "Pan-cancer analysis of genomic scar signatures associated with homologous recombination deficiency suggests novel indications for existing cancer drugs," Biomark Res. 3:9 (May 1, 2015) (10 pages).
Office Action for United States U.S. Appl. No. 16/096,723 dated Sep. 28, 2022 (84 pages).
Office Action for United States U.S. Appl. No. 16/096,731 dated Dec. 7, 2022 (68 pages).
Office Action for Chinese Patent Application No. 201780027322.7 dated Nov. 14, 2022 (7 pages).
English Translation for the Office Action for Chinese Patent Application No. 201780027314.2 dated Nov. 30, 2022 (9 pages).
Chinese Search Report for Chinese Patent Application No. 201780027314.2 dated Nov. 24, 2022 (4 pages).
Piraino et al., Beyond the exome: the role of non-coding somatic mutations in cancer. Annals of Oncology. Feb. 1, 2016;27(2):240-8.
Notice of Reasons for Rejection for Japanese Application No. 2022-175913 mailed Feb. 27, 2024.

\* cited by examiner

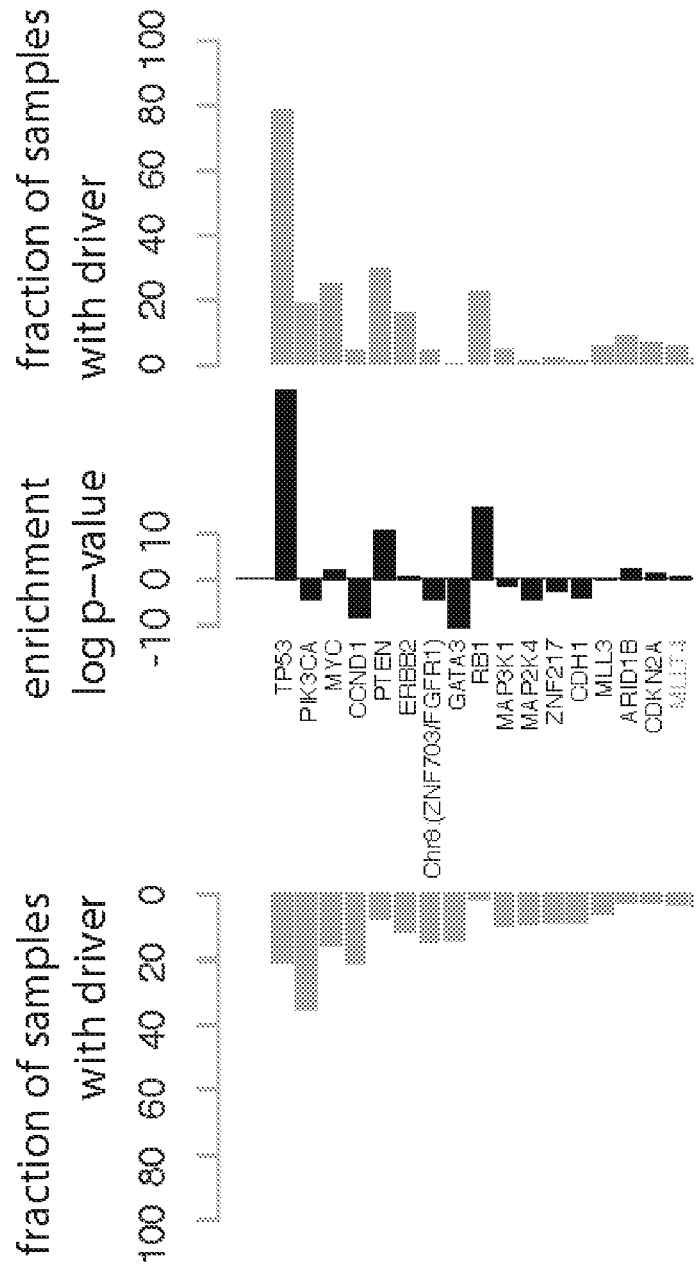

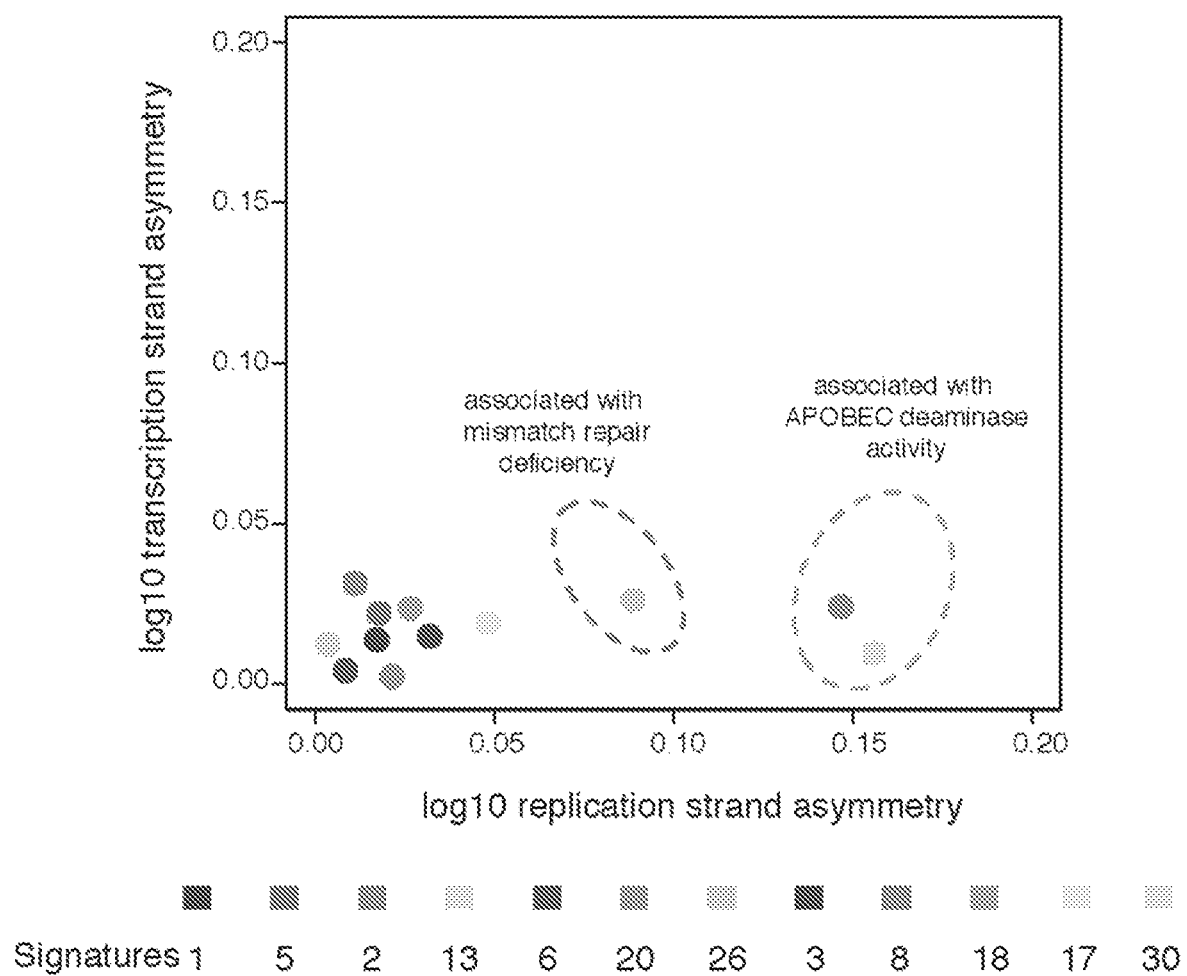

Extended Data Figure 1

FIG. 10A

| chr | start | end | length | number of breakpoints | number of samples | known fragile site | nearby cancer gene |
|---|---|---|---|---|---|---|---|
| 1 | 735890 | 1491917 | 756027 | 25 | 13 | FRA1A | |
| 1 | 66670535 | 67015462 | 344927 | 52 | 21 | | |
| 12 | 11843027 | 12728445 | 885418 | 91 | 35 | | ETV6 |
| 8 | 128355027 | 129238954 | 883927 | 114 | 58 | | MYC |
| 5 | 44222786 | 44992104 | 769318 | 49 | 22 | | |
| 5 | 106572301 | 107085560 | 513259 | 36 | 18 | FRA5F | |
| 7 | 92014640 | 92358020 | 343380 | 31 | 13 | FRA7E | CDK6 |
| 11 | 33671711 | 34956790 | 1285079 | 66 | 31 | FRA11E FRA11E-narrow | LMO2 |
| 11 | 64715221 | 65348449 | 633228 | 64 | 31 | FRA11H | |

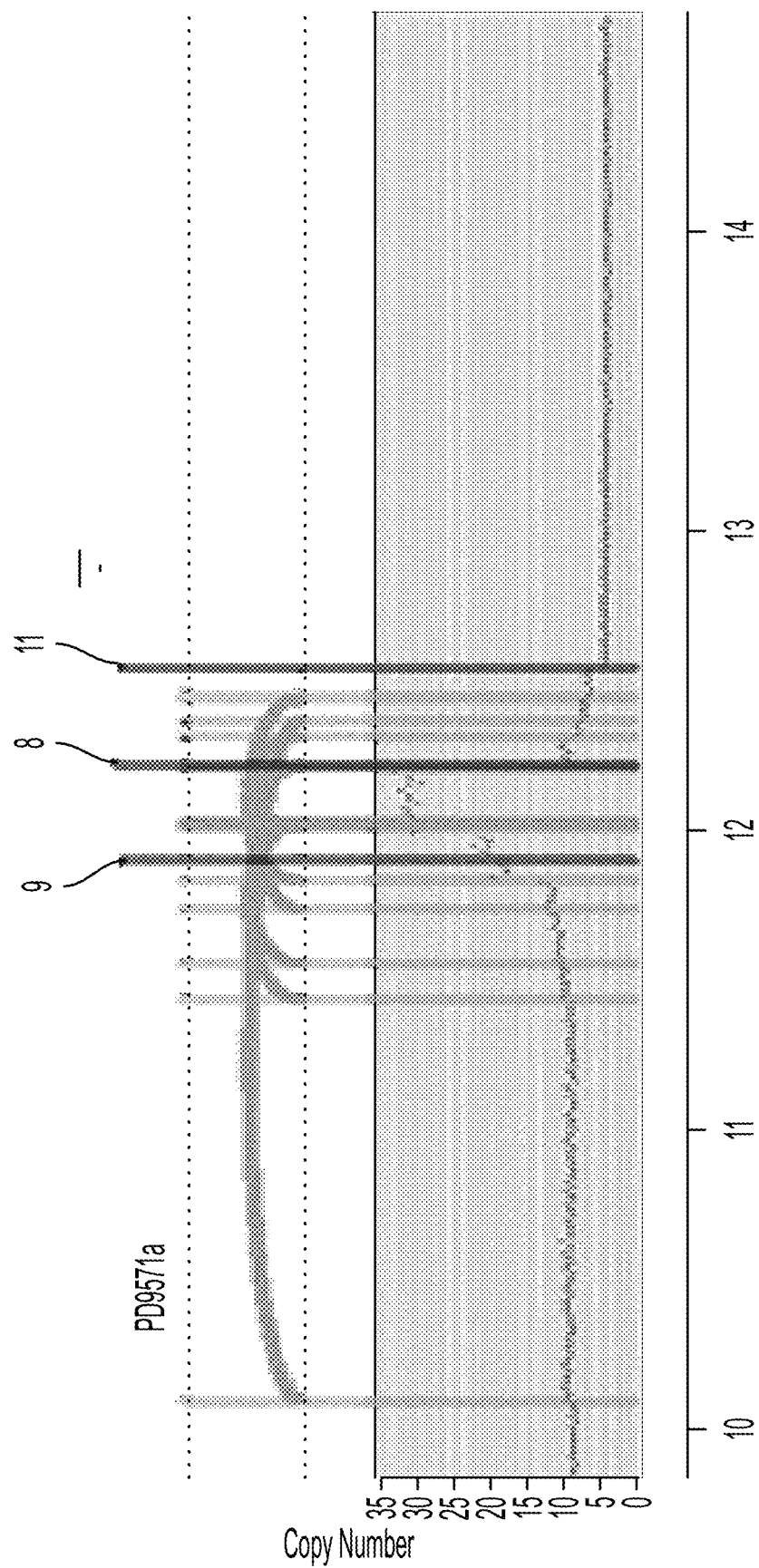

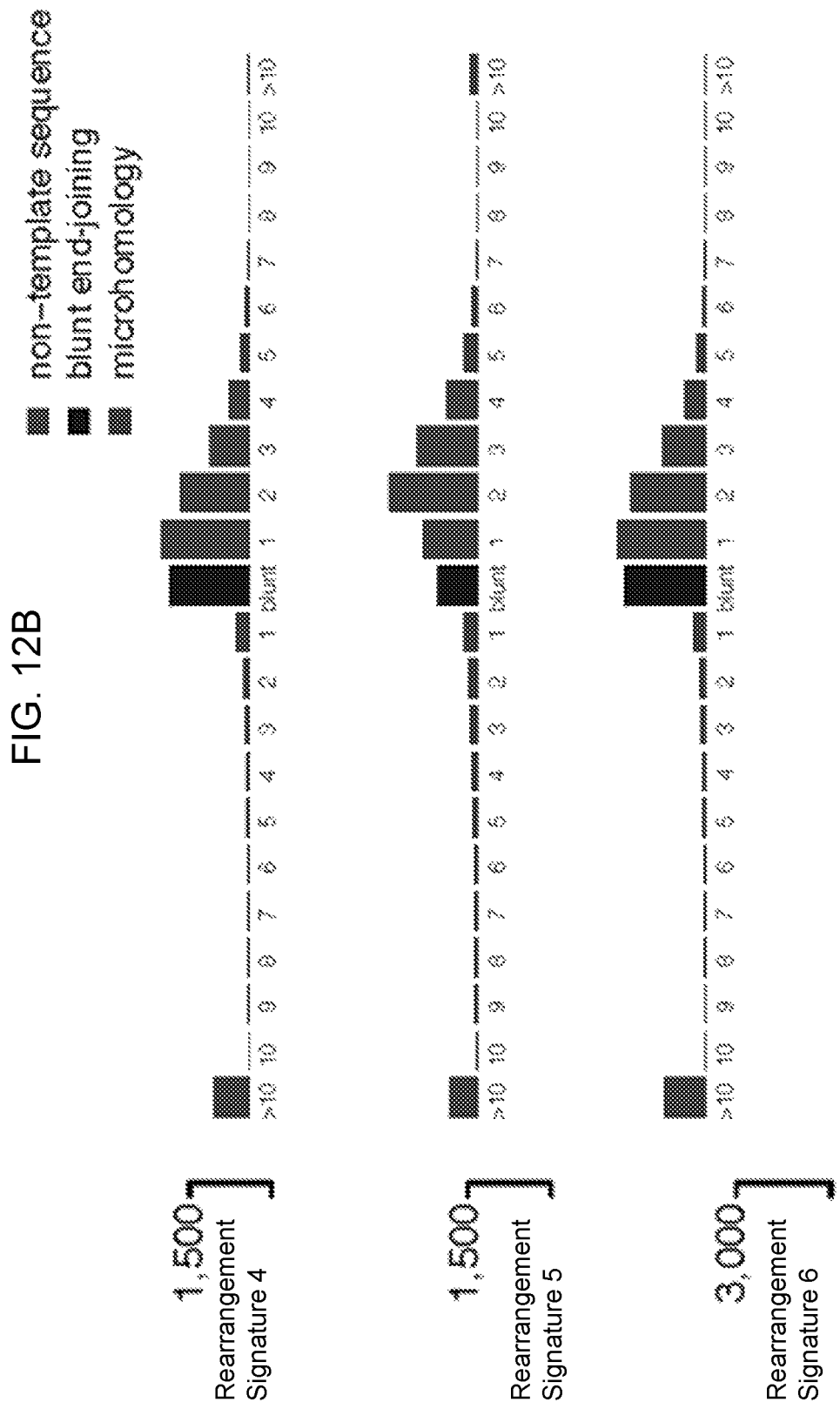

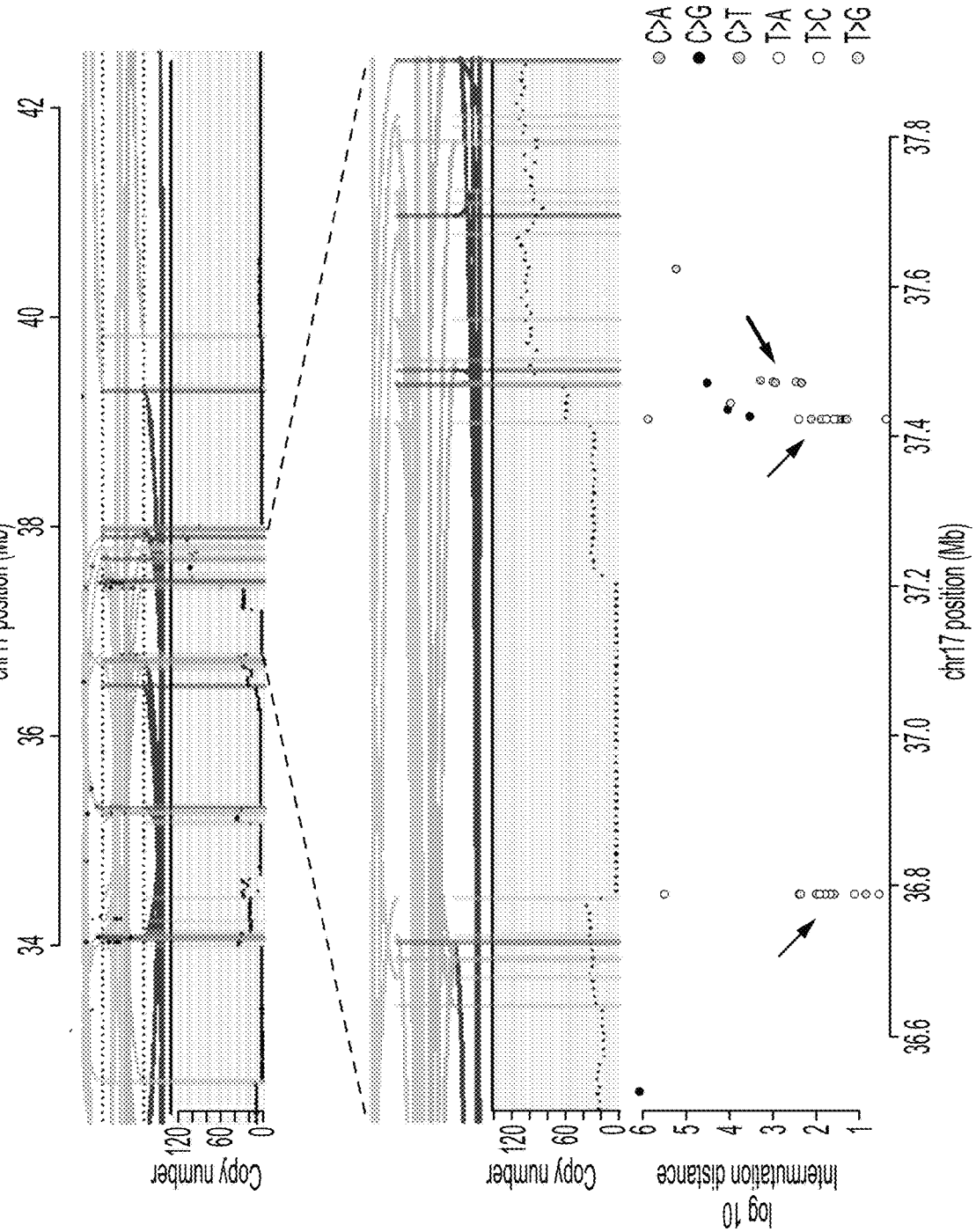

METHOD OF CHARACTERIZING A DNA SAMPLE

FIELD OF INVENTION

The present invention relates to a method of characterising a DNA sample. It is particularly, but not exclusively, concerned with a method for characterising the properties of cancer based on a DNA sample from a tumour.

BACKGROUND TO THE INVENTION

The mutational theory of cancer proposes that changes in DNA sequence, termed "driver" mutations, confer proliferative advantage upon a cell, leading to outgrowth of a neoplastic clone [1]. Some driver mutations are inherited in the germline, but most arise in somatic cells during the lifetime of the cancer patient, together with many "passenger" mutations not implicated in cancer development [1]. Multiple mutational processes, including endogenous and exogenous mutagen exposures, aberrant DNA editing, replication errors and defective DNA maintenance, are responsible for generating these mutations [1-3].

Over the past five decades, several waves of technology have advanced the characterisation of mutations in cancer genomes. Karyotype analysis revealed rearranged chromosomes and copy number alterations. Subsequently, loss of heterozygosity analysis, hybridisation of cancer-derived DNA to microarrays and other approaches provided higher resolution insights into copy number changes [4-8]. Recently, DNA sequencing has enabled systematic characterisation of the full repertoire of mutation types including base substitutions, small insertions/deletions, rearrangements and copy number changes [9-13], yielding substantial insights into the mutated cancer genes and mutational processes operative in human cancer.

As for many cancer classes, most currently available breast cancer sequences target protein-coding exons [8, 11-15]. Consequently, there has been limited consideration of mutations in untranslated, intronic and intergenic regions, leaving central questions pertaining to the molecular pathogenesis of the disease unresolved. First, the role of activating driver rearrangements [16-18] forming chimeric (fusion) genes/proteins or relocating genes adjacent to new regulatory regions as observed in renal [19] and haemopoietic malignancies. Second, the role of driver substitutions and indels in non-coding regions of the genome [20, 21]. Common inherited variants conferring susceptibility to human disease are generally in non-coding regulatory regions and the possibility that similar mechanisms operate somatically in cancer was highlighted by the discovery of somatic driver substitutions in the TERT gene promoter [22, 23]. Third, which mutational processes generate the somatic mutations found in breast cancer [2, 24]. Addressing this question has been constrained because exome sequences do not inform on genome rearrangements and capture relatively few base substitution mutations, thus limiting statistical power to extract the mutational signatures imprinted on the genome by these processes [24, 25].

The present inventors have analysed the complete genome sequences of 560 cases in order to address these and other questions and to pave the way to a comprehensive understanding of the origins and consequences of somatic mutations in breast cancer.

From this analysis, it has been possible to determine certain characteristics of a cancer tumour based on the mutations found in DNA obtained from that tumour.

STATEMENTS OF INVENTION

An exemplary embodiment of the present invention provides a method of characterising a DNA sample obtained from a tumour, the method including three or more of the following steps a) to e):
  a) determining a catalogue of base substitution signatures which are present in the sample;
  b) determining a catalogue of rearrangement signatures which are present in the sample;
  c) determining a catalogue of insertion/deletion signatures which are present in the sample
  d) determining the overall copy number profile in the sample
  e) identifying putative driver mutations present in the sample and
based on said determinations and identifications, constructing an interpreted profile of the tumour.

A further exemplary embodiment of the present invention provides a computer program product containing non-transitory memory storing a computer program which, when run on a computer, performs three or more of the following steps a) to e):
  a) determining a catalogue of base substitution signatures which are present in the sample;
  b) determining a catalogue of rearrangement signatures which are present in the sample;
  c) determining a catalogue of insertion/deletion signatures which are present in the sample
  d) determining the overall copy number profile in the sample
  e) identifying putative driver mutations present in the sample and
based on said determinations and identifications, constructs an interpreted profile of the tumour.

A further exemplary aspect of the present invention provides a computer having a processor, wherein the processor is configured to perform three or more of the following steps a) to e):
  a) determining a catalogue of base substitution signatures which are present in the sample;
  b) determining a catalogue of rearrangement signatures which are present in the sample;
  c) determining a catalogue of insertion/deletion signatures which are present in the sample
  d) determining the overall copy number profile in the sample
  e) identifying putative driver mutations present in the sample and
based on said determinations and identifications, to construct an interpreted profile of the tumour.

BRIEF DESCRIPTION OF THE FIGURES

FIGS. 3A-3D show the cohort and catalogue of somatic mutations in 560 breast cancers; FIG. 3A is a summary of the 560 human breast cancers; FIGS. 3B-3D show a catalogue of base substitutions, insertions/deletions, rearrangements and driver mutations in the 560 breast cancers (sorted by total substitution burden) with the indel axis limited to 5,000(*); FIGS. 3B-3D also show a complete list of curated driver genes sorted by frequency (descending) and showing the fraction of ER positive (left, total 366) and ER negative (right, total 194) samples carrying a mutation in the relevant driver gene presented in grey along with the log 10 p-value of enrichment of each driver gene towards the ER positive or ER negative cohort in black;

FIG. 4A shows the distributions of substitution (darker dots, top lines) and indel (lighter dots, bottom lines) mutations within the footprint of five regulatory regions identified as being more significantly mutated than expected is provided on the left, along with the proportion of base substitution mutation signatures associated with corresponding samples carrying mutations in each of these non-coding regions on the right; FIG. 4B shows the mutability of TGAACA/TGTTCA motifs within inverted repeats of varying flanking palindromic sequence length compared to motifs not within an inverted repeat; FIG. 4C shows the variation in mutability between loci of TGAACA/TGTTCA inverted repeats with 9 bp palindromes;

FIG. 5A shows twelve mutation signatures extracted using Non-Negative Matrix Factorization with each signature ordered by mutation class (C>A/G>T, C>G/G>C, C>T/G>A, T>A/A>T, T>C/A>G, T>G/A>C), taking immediate flanking sequence into account. For each class, mutations are ordered by 5' base (A,C,G,T) first before 3' base (A,C,G,T); FIG. 5B shows the spectrum of base substitution signatures within 560 breast cancers, the mutation signatures are ordered according to broad biological groups: Signatures 1 and 5 are correlated with age of diagnosis, Signatures 2 and 13 are putatively APOBEC-related, Signatures 6, 20 and 26 are associated with MMR deficiency, Signatures 3 and 8 are associated with HR deficiency, Signatures 18, 17 and 30 have unknown etiology; FIG. 5C shows the distribution of mutation counts for each signature in relevant breast cancer samples with the percentage of samples carrying each signature provided above each signature;

FIGS. 6A-6B show the distribution of base substitution signatures in 560 breast cancers; FIG. 6A shows the contrasting transcriptional strand asymmetry and replication strand asymmetry between twelve base substitution signatures; FIG. 6B shows the six rearrangement signatures extracted using Non-Negative Matrix Factorization with the probability of rearrangement element on y-axis and the rearrangement size on x-axis.

FIG. 8A shows the frequency of driver mutations in breast cancer genes; FIG. 8B shows driver mutations by mutation type; FIGS. 8C and 8D show the distribution of rearrangements throughout the genome including background rearrangement density (continuous line) based on rearrangement breakpoints in intergenic regions only) and frequency of rearrangement within breast cancer genes (spikes);

FIG. 9A is a Manhattan plot demonstrating sites with most significant p-values as identified by binning analysis with highlighted sites which were also detected by the method seeking recurrence when partitioned by genomic features; FIGS. 9B-9D show the locus at chr11:65 Mb which was identified by independent analyses as being more mutated than expected by chance and, in the lowermost panel, a rearrangement hotspot analysis identified this region as a tandem duplication hotspot, with nested tandem duplications noted at this site; partitioning the genome into different regulatory elements, an analysis of substitutions and indels identified lncRNAs MALAT1 and NEAT1 (topmost panels) with significant p-values;

FIGS. 10A-10D show hotspots of tandem duplications; FIG. 10A lists hotspots of tandem duplications; FIG. 10B-10D show ETV6 tandem duplication hotspot occurring in 6 different patients;

FIG. 11B, age of diagnosis; FIG. 11C, tumour grade; FIG. 11D, menopausal status; FIG. 11E, ER status; FIG. 11F, immune response metagene panel; FIG. 11G, lymphocytic infiltration score;

FIGS. 12A-12C show the rearrangement breakpoint junctions; FIGS. 12A-12B show the breakpoint features of rearrangements in the 560 breast cancers sorted by rearrangement signature with non-template sequences to the left of the "blunt" marking and microhomology to the right; FIG. 12C shows the breakpoint features in BRCA and non-BRCA cancers; and FIGS. 13A-13B show signatures of focal hypermutation; FIG. 13A shows kataegis and alternative kataegis occurring at the same locus (ERBB2 amplicon in PD13164a) with the copy number (y-axis) depicted as black dots; lines represent rearrangements breakpoints with the topmost panel showing a ~10 Mb region including the ERBB2 locus; the second panel from top zooms in 10-fold to a ~1 Mb window highlighting co-occurrence of rearrangement breakpoints, with copy number changes and three different kataegis loci; the third panel from top demonstrates kataegis loci in more detail with log 10 intermutation distance on y axis and black arrow highlighting kataegis and light grey blue arrows highlighting alternative kataegis;

FIG. 13B shows sequence context of kataegis and alternative kataegis identified in this dataset.

BRIEF DESCRIPTION OF THE TABLES

Figure 1:
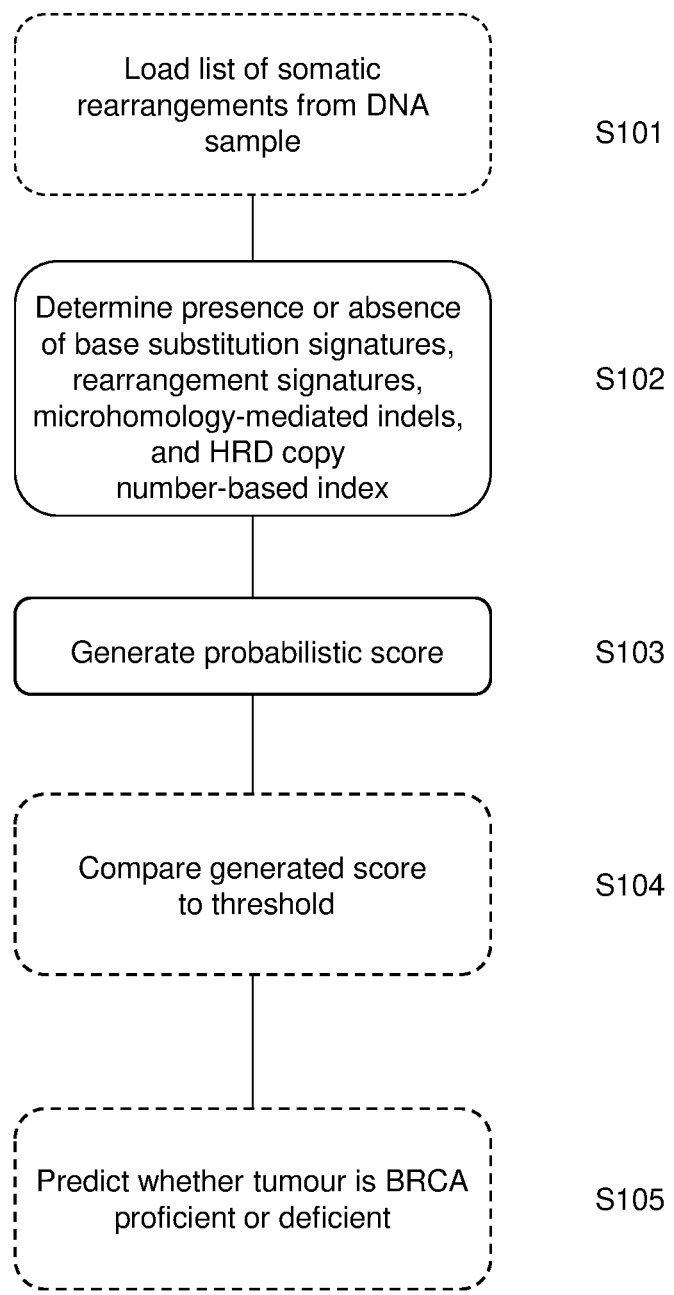
FIG. 1 is a flow diagram showing, in schematic form, steps S101-S105 of a method of characterising a DNA sample according to an embodiment of the present invention.

Table 1 sets out a quantitative definition of a number of rearrangement signatures;

Table 2 is a summary of the somatic mutation catalogue;

Table 3 is a summary of the hunt for novel driver mutations using base substitutions only Table 4 is a summary of the hunt for novel driver mutations using insertions/deletions only Table 5 is a summary of the hunt for novel driver mutations using a combination of base substitutions and insertions/deletions Table 6 is a curated cancer gene list for all cancer types Table 7 is a summary of the hunt for driver mutations from amongst rearrangements Table 8 is the list of driver mutations identified in 560 breast cancers Table 9 is a summary of an analysis searching for predicted in-frame gene fusions, recurrent donors and acceptors Table 10 is a summary of the analysis for recurrent non-coding events.

DETAILED DESCRIPTION

A first aspect of the present invention provides a method of characterising a DNA sample obtained from a tumour, the method including three or more of the following steps a) to e):

a) determining a catalogue of base substitution signatures which are present in the sample;

b) determining a catalogue of rearrangement signatures which are present in the sample;

c) determining a catalogue of insertion/deletion signatures which are present in the sample d) determining the overall copy number profile in the sample e) identifying putative driver mutations present in the sample and based on said determinations and identifications, constructing an interpreted profile of the tumour.

For the avoidance of doubt, the method according to this aspect may include any combination of three or more of the steps a) to e), being: steps a), b) and c); steps a), b) and d); steps a), b) and e); steps a), c) and d); steps a), c) and e); steps a), d) and e); steps b), c) and d); steps b), d) and e); steps c), d) and e); steps a), b), c) and d); steps a), c), d) and e); steps b), c), d) and e); or all of the steps a) to e).

In certain embodiments the method further includes the steps of:

f) identifying putative recurrently mutated non-coding sites, and using the identified putative recurrently mutated non-coding sites in constructing the interpreted profile.

In certain embodiments the method further includes the steps of:

g) obtaining a biologically useful over-arching summary of the sample, and using the obtained summary in constructing the interpreted profile.

In certain of those embodiments, step g) includes identifying whether the sample has a high or low likelihood of being homologous recombination (HR)-deficient by performing the steps of: determining the presence or absence of a plurality of base substitution signatures, rearrangement signatures and insertion/deletion (indel) signatures in the sample and copy number profiles for the sample; generating, from the presence or absence of said plurality of base substitution signatures, rearrangement signatures and indel signatures in the sample and the copy number profiles for the sample, a probabilistic score; and based on said probabilistic score, identifying whether said sample has a high or low likelihood of being homologous recombination (HR)-deficient.

Alternatively, step g) may include identifying whether the sample has a high or low likelihood of being homologous recombination (HR)-deficient by performing the steps of: performing two or more of the following steps:

a) determining the presence or absence of at least one base substitution signature in the sample b) determining the presence or absence of at least one rearrangement signature in the sample c) determining the presence or absence of at least one indel signature in the sample; and d) determining a copy number profile for the sample;

generating, from the above determinations, a probabilistic score; and based on said probabilistic score, identifying whether said sample has a high or low likelihood of being homologous recombination (HR)-deficient.

Preferably three or more and more preferably all four of the determining steps of this aspect are performed. The probabilistic score and the weighting of the determinations in generating that probabilistic score may vary depending on which determining steps are performed and/or depending on the number of determining steps performed and/or the number of signatures or profiles used in each determining step.

Where base substitution signatures are considered, preferably the plurality of base substitution signatures include either base substitution signature 3 or base substitution signature 8 or both.

Where rearrangement signatures are considered, preferably the plurality of rearrangement signatures includes either rearrangement signature 5 or rearrangement signature 3 or both.

Where indel signatures are considered, preferably the plurality of indel signatures include microhomology-mediated indels.

Preferably the copy number profiles, if considered, include the HRD copy number-based index.

In particular embodiments of the present invention, the plurality of base substitution signatures, the plurality of rearrangement signatures and the plurality of indel signatures consist of base substitution signature 3, base substitution signature 8, rearrangement signature 5 and rearrangement signature 3 and microhomology-mediated indels. Following an extensive study of WGS from breast cancers, these five factors, together with the copy number profile, have been found to have the greatest influence on whether a tumour is HR-deficient or not.

Preferably in such embodiments, the probabilistic score is a weighted score which gives weight to the factors in the following precedence (greatest first): microhomology-mediated indels, base substitution signature 3, rearrangement signature 5, the HRD copy number-based index, rearrangement signature 3 and base substitution signature 8. The study of WGS from breast cancers found that the above order was indicative of the importance of these six factors.

The method may further include the step of cataloguing the somatic mutations in said sample to produce a mutational catalogue for that sample, wherein the presence or absence of said base substitution signatures, rearrangement signatures and/or indel signatures as required, is derived from said mutational catalogue.

When such a catalogue has been obtained, the method may further include the step of determining the number of mutations in the mutational catalogue which are attributable to each of the base substitution signatures, rearrangement signatures and/or indel signatures, as required, which are determined to be present.

Generating the probabilistic score may include the sub steps of: log-transforming the number of mutations attributed to each of the signatures; normalising the log-transformed number of mutations for each signature and the copy number profile; and weighting each of said normalised values by a predetermined weighting factor which represents the likelihood of the signature or profile associated with that value causing the tumour to be HR deficient.

By log-transforming the number of mutations and normalising all of the features, an accurate balance between the influence of the various factors can be obtained.

In one particular embodiment, the probabilistic score is generated as $$P(C_i = BRCA) = \frac{1}{1 + e^{-(\beta_0 + x_i^T \beta)}}$$

where $C_i$ is the variable encoding the status of $i^{th}$ sample $\beta_0$ is the intercept weight $x_i^T$ is the vector encoding features of $i^{th}$ sample; and $\beta$ is the vector of weights.

For embodiments wherein the features consist of the six features set out above, the vector of weights $\beta$ may be as set out in the table below, or within a variation of ±10%, preferably ±5% of these weights:

| Feature | weight β |
|---|---|
| Proportion of indels with micro-homology | 2.129 |
| Number of base substitutions of signature 3 | 1.239 |
| Number of rearrangement signature 5 rearrangements | 0.978 |
| HRD index | 0.613 |
| Number of rearrangement signature 3 rearrangements | 0.588 |
| Number of base substitutions of signature 8 | 0.444 |

For other embodiments wherein the features consist of the six features set out above, the vector of weights $\beta$ may be as set out below in the table below, or within a variation of ±10%, preferably ±5% of these weights:

| Feature | weight β |
|---|---|
| Proportion of indels with micro-homology | 2.398 |
| Number of base substitutions of signature 3 | 1.611 |
| Number of rearrangement signature 5 rearrangements | 0.847 |
| HRD index | 0.667 |
| Number of rearrangement signature 3 rearrangements | 1.153 |
| Number of base substitutions of signature 8 | 0.091 |

For embodiments wherein the features consist of a subset of the six features set out above, the vector of weights $\beta$ may be as set out in the table below, or within a variation of ±10%, preferably ±5% of these weights:

| Feature 1 | Weight | Feature 2 | Weight |
|---|---|---|---|
| Number of base substitutions of signature 3 | 2.371 | Number of rearrangement signature 3 rearrangements | 1.835 |
| Number of base substitutions of signature 3 | 1.876 | Number of rearrangement signature 5 rearrangements | 2.989 |
| Number of base substitutions of signature 3 | 2.931 | Proportion of indels with micro-homology | 3.984 |
| Number of base substitutions of signature 3 | 2.429 | HRD index | 2.051 |
| Number of rearrangement signature 3 rearrangements | 3.559 | Proportion of indels with micro-homology | 4.819 |
| Number of rearrangement signature 3 rearrangements | 1.650 | HRD index | 1.895 |
| Number of rearrangement signature 3 rearrangements | 2.297 | Number of base substitutions of signature 8 | 0.676 |
| Number of rearrangement signature 5 rearrangements | 3.026 | Proportion of indels with micro-homology | 1.933 |
| Number of rearrangement signature 5 rearrangements | 3.715 | HRD index | 1.017 |
| Proportion of indels with micro-homology | 2.523 | HRD index | 1.894 |
| Proportion of indels with micro-homology | 3.223 | Number of base substitutions of signature 8 | 0.807 |
| HRD index | 2.813 | Number of base substitutions of signature 8 | 0.357 |

The step of identifying may include comparing said score to a predetermined threshold and performing said identification based on said comparison. The threshold may be set based on clinical parameters. For example, the weighted score may be compared to a threshold and, from that comparison, a clinical decision as to how to treat a tumour from which the DNA sample was taken can be made.

The predetermined threshold may be selected in a number of ways. In particular, different thresholds for this determination may be set depending on the context and the desired certainty of the outcome.

In some embodiments, the threshold will be an absolute number of rearrangements from the rearrangement catalogue of the DNA sample which are determined to be associated with a particular rearrangement signature. If this number is exceeded, then it can be determined that a particular rearrangement signature is present in the DNA sample.

The rearrangement signatures are generally "additive" with respect to each other (i.e. a tumour may be affected by the underlying mutational processes associated with more than one signature and, if this is the case, a sample from that tumour will generally display a higher overall number of rearrangements (being the sum of the separate rearrangements associated with each of the underlying processes), but with the proportion of rearrangements spread over the signatures which are present). As a result, in determining the presence or absence of a particular signature, attention may focus on the absolute number of rearrangements associated with a particular signature in the sample (which may be calculated by the methods described below in other aspects of the invention). Such thresholds are generally better in situations where multiple signatures are present in a sample.

In these embodiments, a signature may be determined to be present if at least 5 and preferably at least 10 informative rearrangements are associated with it.

In other embodiments, the threshold combines the total number of rearrangements detected in the sample (which may be set to ensure that the analysis is representative) along with a proportion of the rearrangements which are associated with a particular signature (again, as determined by the methods described below in other aspects of the invention).

For example, the requirements for determination that a signature is present may be that there are at least 20, preferably at least 40, more preferably at least 50 informative rearrangements and a signature may be deemed to be present if a proportion of at least 10%, preferably at least 20%, more preferably at least 30% of the rearrangements are associated with it. The higher the number of rearrangements present in a sample, the lower the proportional threshold for detection of a specific signature may be.

The proportional thresholds may be adjusted depending on the number of other signatures which make up a significant portion of the rearrangements found in the sample (e.g., if 4 signatures are each present with 20-25% of the rearrangements, then it may be determined that all 4 signatures are present, rather than no signatures at all are present), even if the threshold determined under the present embodiments is 30%.

The above thresholds are based on data obtained from genomes sequenced to 30-40 fold depth. If data is obtained from genomes sequenced at lower coverages, then the number of rearrangements detected overall is likely to be lower, and the thresholds will need to be adjusted accordingly.

The method may further include the steps of:
h) identifying the presence of mis-match repair (MMR) deficiency in the sample by using the presence or absence of base substitution signatures and indel signatures, and
using this identification in constructing the interpreted profile.

The method may further include the steps of:
i) identifying mutational characteristics in the sample that are informative of pathophysiological processes that are targetable including signatures relating to the immunological responses or to other DNA damage response processes, and
using the identified characteristics in constructing the interpreted profile.

Preferably the catalogue of base substitution signatures, if obtained, is obtained by: cataloguing the somatic mutations in said sample to produce a mutational catalogue for that sample; determining the contributions of known mutational signatures to said mutational catalogue by determining a scalar factor for each of a plurality of said known mutational signatures which together minimize a function representing the difference between the mutations in said catalogue and the mutations expected from a combination of said plurality of known mutational signatures scaled by said scalar factors; and if the scalar factor corresponding to any one of said mutational signatures exceeds a predetermined threshold, including said mutation signature in the catalogue of base substitution signatures for the sample.

Preferably the method of this aspect includes the further step of, prior to said step of determining, filtering the mutations in said catalogue to remove either residual germline mutations or known sequencing artefacts or both. Such filtering can be highly advantageous to remove mutations from the catalogue which are known to arise from mechanisms other than somatic mutation, and may therefore cloud or obscure the contributions of the mutational signatures, or lead to false positive results.

For example, the filtering may use a list of known germline polymorphisms and remove somatic mutations resulting from those polymorphisms from the catalogue prior to determining the contributions of the mutational signatures.

As a further example, the filtering may use BAM files of unmatched normal human tissue sequenced by the same process as the DNA sample and discard any somatic mutation which is present in at least two well-mapping reads in at least two of said BAM files. This approach can remove artefacts resulting from the sequencing technology used to obtain the sample.

The method may further include the step of selecting said plurality of known mutational signatures as a subset of all known mutational signatures. By selecting a subset, for example, based on prior knowledge about the sample, the number of possible signatures contributing to the mutational catalogue is reduced, which is likely to increase the accuracy of the determining step.

For example, the subset of mutational signatures may be selected based on biological knowledge about the DNA sample or the mutational signatures or both. Thus, it may be immediately apparent that a certain DNA sample cannot have resulted from a particular mutational signature as a result of characteristics of the DNA sample and the particular mutational signature. Further possibilities are described in more detail in the embodiments below.

In particular embodiments, the step of determining may determine the scalars $E_i$ which minimize the Frobenius norm:

$$\min\left\|\vec{M} - \sum_{i=1}^{q} (\vec{S}_i \times E_i)\right\|_2^F$$

wherein $\vec{S}_i$ and $\vec{M}$ are equally-sized vectors with nonnegative components being, respectively, a consensus mutational signature and the mutational catalogue and q is the number of signatures in said plurality of known mutational signatures, and wherein $E_i$ are further constrained by the requirements that $0 \leq E_i \leq \|\vec{S}_i\|_1$, i=1 . . . q, and $$\sum_{i=1}^{q} E_i = \|\vec{S}_i\|_1.$$

Preferably the catalogue of rearrangement signatures, if obtained, is obtained by: cataloguing the somatic mutations in said sample to produce a rearrangement catalogue for that sample which classifies identified rearrangement mutations in the sample into a plurality of categories; determining the contributions of known rearrangement signatures to said rearrangement catalogue by computing the cosine similarity between the rearrangement mutations in said catalogue and the known rearrangement signatures; and if the number or proportion of rearrangements in the rearrangement catalogue which are determined to be associated with one of said rearrangement signatures exceeds a predetermined threshold, including said rearrangement signature in the catalogue of rearrangement signatures for the sample.

Preferably the method includes the further step of, prior to said step of determining, filtering the mutations in said catalogue to remove either residual germline structural variations or known sequencing artefacts or both. Such filtering can be highly advantageous to remove rearrangements from the catalogue which are known to arise from mechanisms other than somatic mutation, and may therefore cloud or obscure the contributions of the rearrangement signatures, or lead to false positive results.

For example, the filtering may use a list of known germline rearrangement or copy number polymorphisms and remove somatic mutations resulting from those polymorphisms from the catalogue prior to determining the contributions of the rearrangement signatures.

As a further example, the filtering may use BAM files of unmatched normal human tissue sequenced by the same process as the DNA sample and discards any somatic mutation which is present in at least two well-mapping reads in at least two of said BAM files. This approach can remove artefacts resulting from the sequencing technology used to obtain the sample.

The classification of the rearrangement mutations may include identifying mutations as being clustered or non-clustered. This may be determined by a piecewise-constant fitting ("PCF") algorithm which is a method of segmentation of sequential data. In particular embodiments, rearrangements may be identified as being clustered if the average density of rearrangement breakpoints within a segment is a certain factor greater than the whole genome average density of rearrangements for an individual patient's sample. For example the factor may be at least 8 times, preferably at least 9 times and in particular embodiments is 10 times. The inter-rearrangement distance is the distance from a rearrangement breakpoint to the one immediately preceding it in the reference genome. For any given breakpoint, this measurement is already known.

The classification of the rearrangement mutations may include identifying rearrangements as one of: tandem duplications, deletions, inversions or translocations. Such classifications of rearrangement mutations are already known.

The classification of the rearrangement mutations may further include grouping mutations identified as tandem duplications, deletions or inversions by size. For example, the mutations may be grouped into a plurality of size groups by the number of bases in the rearrangement. Preferably the size groups are logarithmically based, for example 1-10 kb, 10-100 kb, 100 kb-1 Mb, 1 Mb-10 Mb and greater than 10 Mb. Translocations cannot be classified by size.

In particular embodiments, in each DNA sample the number of rearrangements $E_i$ associated with the ith mutational signature $\vec{S}_i$ is determined as proportional to the cosine similarity ($\vec{C}_i$) between the catalogue of this sample $\vec{M}$ and $\vec{S}_i$:

$$\vec{C}_i = \frac{\vec{S}_i \cdot \vec{M}}{\|\vec{S}_i\| \|\vec{M}\|}$$

wherein:

$$E_i = \frac{\vec{C}_i}{\sum_{i=1}^{q} \vec{C}_i} \sum_{j=1}^{36} \vec{M}^j$$

wherein $\vec{S}_i$ and $\vec{M}$ are equally-sized vectors with nonnegative components being, respectively, a known rearrangement signature and the mutational catalogue and q is the number of signatures in said plurality of known rearrangement signatures.

The method may further include the step of filtering the number of rearrangements determined to be assigned to each signature by reassigning one or more rearrangements from signatures that are less correlated with the catalogue to signatures that are more correlated with the catalogue. Such filtering can serve to reassign rearrangements from a signature which has only a few rearrangements associated with it (and so is probably not present) to a signature which has a greater number of rearrangement associated with it. This can have the effect of reducing "noise" in the assignment process.

In one embodiment, the step of filtering uses a greedy algorithm to iteratively find an alternative assignment of rearrangements to signatures that improves or does not change the cosine similarity between the catalogue $\vec{M}$ and the reconstructed catalogue $\vec{M}'=S\times\vec{E}'_{ij}$, wherein $\vec{E}'_{ij}$ is the version of the vector $\vec{E}$ obtained by moving the mutations from the signature i to signature j, wherein, in each iteration, the effects of all possible movements between signatures are estimated, and the filtering step terminates when all of these possible reassignments have a negative impact on the cosine similarity.

The subject may be a cancer patient or a suspected cancer patient. For example, the method may be used in the determination or identification of a rearrangement sequence to predict whether the subject has cancer or not or what type of cancer a patient has, or to select the subject for a particular form of treatment.

The method may further include the step of determining if the number or proportion of rearrangements in the rearrangement catalogue which are determined to be associated with one or more of said rearrangement signatures each or in combination exceeds a predetermined threshold and, if so, determining that said rearrangement signature is present in the sample.

Figure 3A:
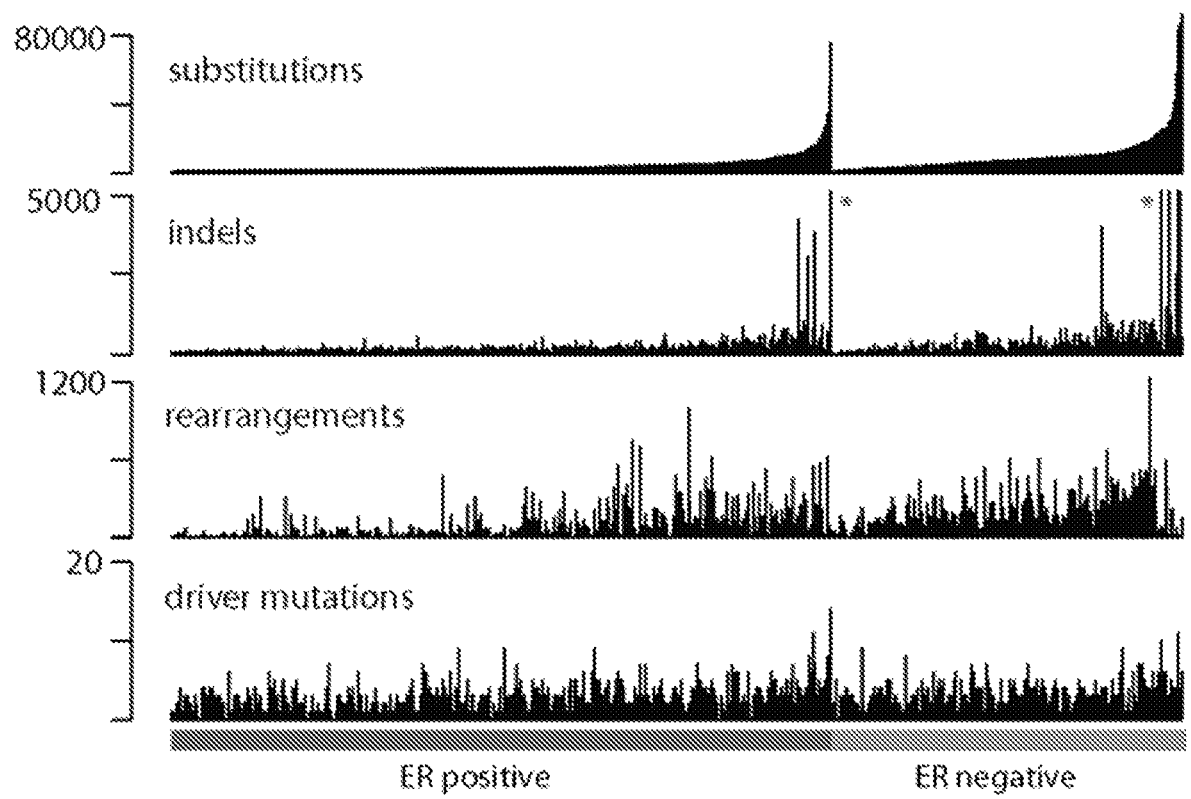
Figure 3C:
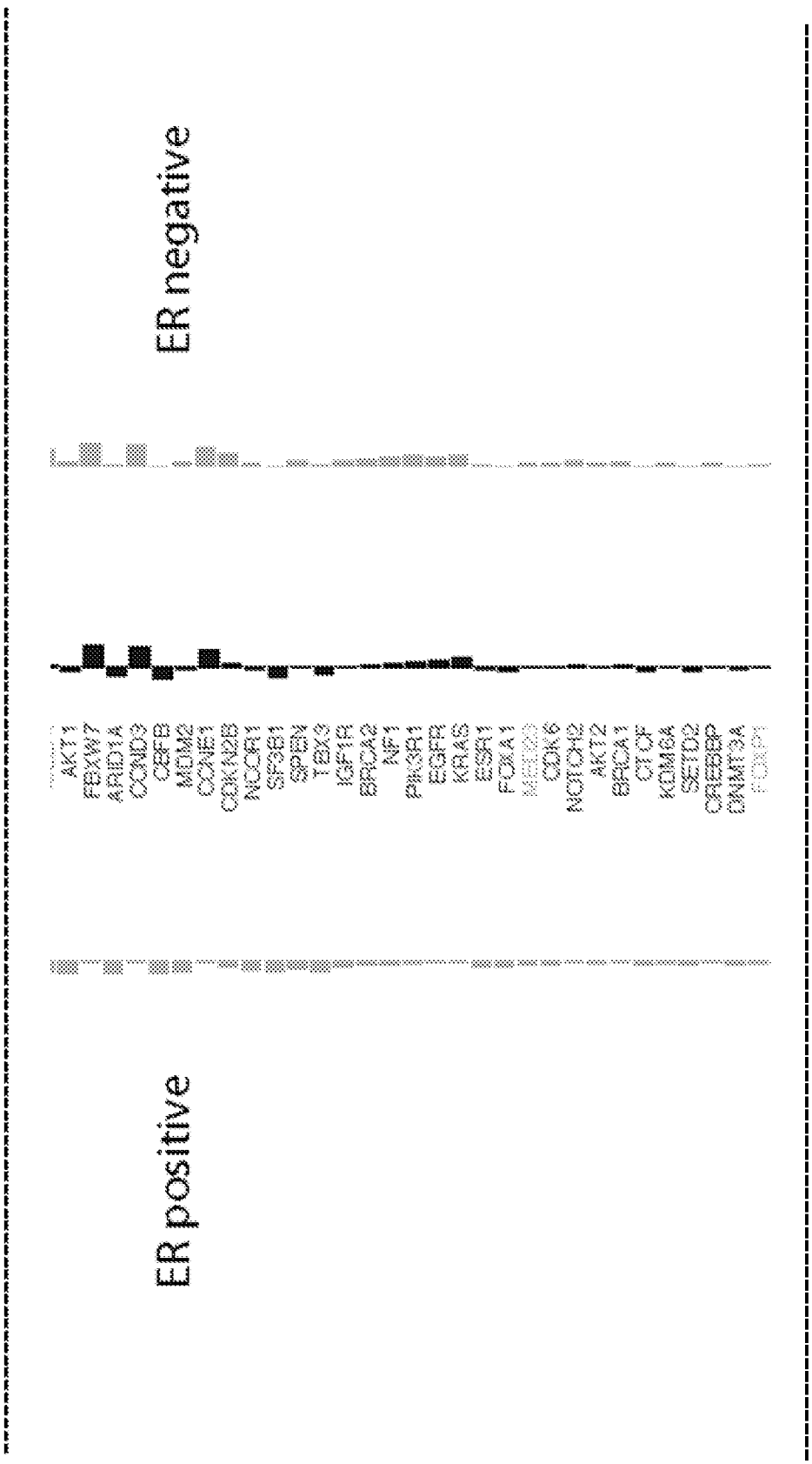
Figure 3D:
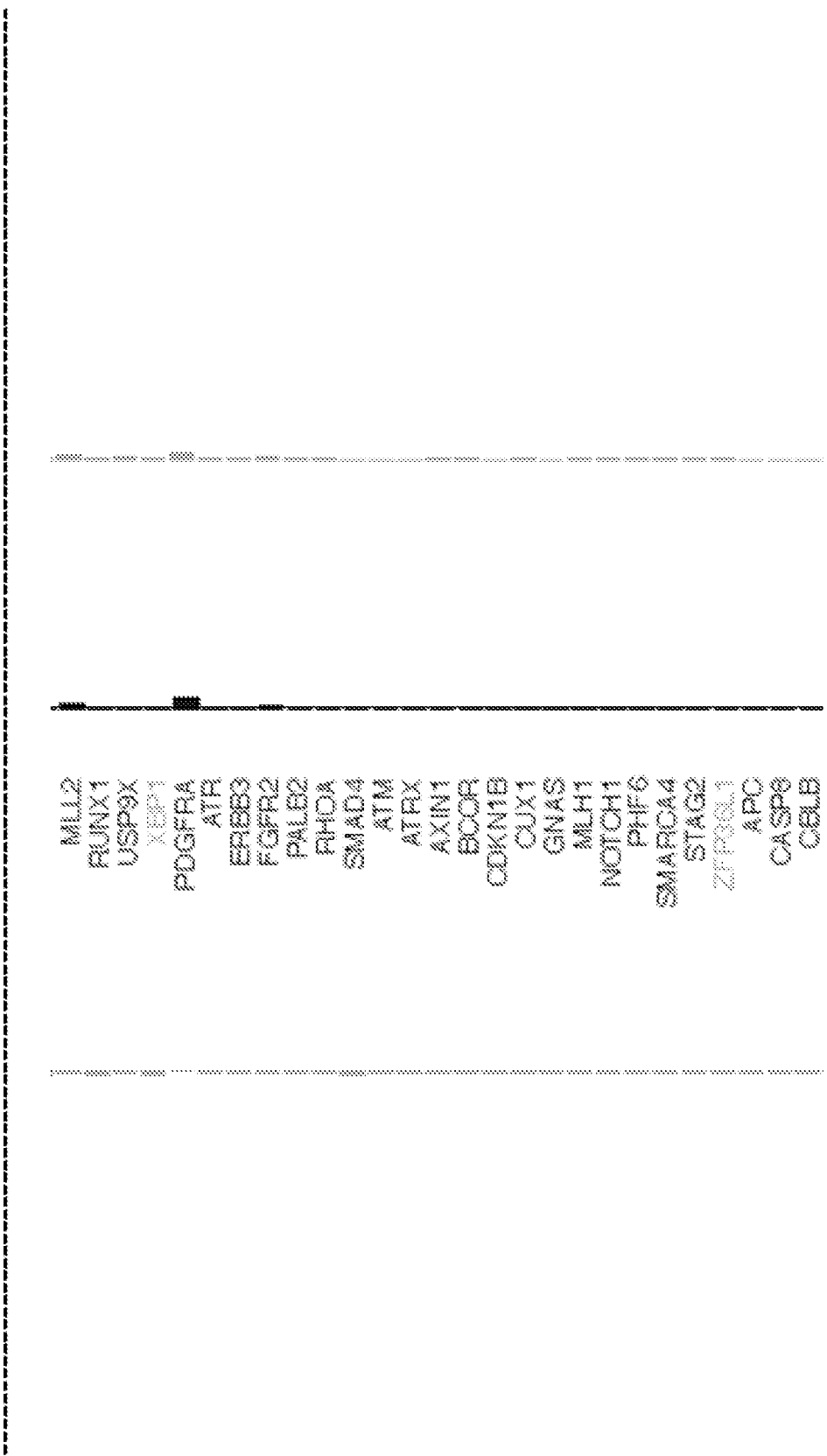

Preferably the step of identifying driver mutations present in the sample determines whether one or more, preferably at least 50%, preferably 75%, more preferably all of the breast cancer genes from the list of 93 cancer genes in FIG. 3C/Table 8 are present or not.

The DNA samples are preferably obtained from both tumour and normal tissues obtained from the patient, e.g. blood sample from the patient and tumour tissue obtained by a biopsy. Somatic mutations in the tumour sample are detected, standardly, by comparing its genomic sequences with the one of the normal tissue.

The patient to be treated is preferably a human patient.

The method of the present aspect may include any combination of some, all or none of the above described preferred and optional features.

Further aspects of the present invention include computer programs for running on computer systems which carry out the method of the above aspect, including some, all or none of the preferred and optional features of that aspect.

A further aspect of the present invention provides a computer program product containing non-transitory memory storing a computer program which, when run on a computer, performs three or more of the following steps a) to e):
  a) determining a catalogue of base substitution signatures which are present in the sample;
  b) determining a catalogue of rearrangement signatures which are present in the sample;
  c) determining a catalogue of insertion/deletion signatures which are present in the sample
  d) determining the overall copy number profile in the sample
  e) identifying putative driver mutations present in the sample and
based on said determinations and identifications, constructs an interpreted profile of the tumour.

A further aspect of the present invention provides a computer having a processor, wherein the processor is configured to perform three or more of the following steps a) to e):
  a) determining a catalogue of base substitution signatures which are present in the sample;
  b) determining a catalogue of rearrangement signatures which are present in the sample;
  c) determining a catalogue of insertion/deletion signatures which are present in the sample
  d) determining the overall copy number profile in the sample
  e) identifying putative driver mutations present in the sample and
based on said determinations and identifications, to construct an interpreted profile of the tumour.

The computer program and the processor of the above two aspects may also carry out some or all of the optional or preferred steps described above in relation to the first aspect.

These and other aspects of the invention are described in further detail below.

Uses of Predictor Outcome

The characterisation (or "genomic profiling") of DNA samples from tumours according to embodiments of the present invention has many uses.

In particular, it is envisaged that this characterisation will allow for significant advances in the interpretation of clinical outcomes and clinical trials data by allowing the identification of common features amongst those patients who respond to a particular treatment and those who do not. At present little is known about what causes two apparently similar tumours to respond or not to a particular therapy. If the tumours are characterised, either before or after the treatment, differences in the tumours may be identified which allow a profile to be developed of the tumours which respond and which do not.

Similarly, the characterisation may be used to select or stratify patients for clinical trials by profiling the tumour in advance and conducting the trial only on patients with particular types of tumour, or ensuring that patients with particular types of tumour are considered as a cohort within the trial and their results considered separately from patients with tumours which exhibit different features.

The characterisation may also be used to guide treatment decisions or in prognosis. In particular, if tumours with particular features or combinations of features are found to respond particularly well or particularly poorly to a certain treatment as a result of studies such as those described in the previous paragraphs, the characterisation may in future be performed in advance of commencing treatment on a patient in order to determine the suitability of that treatment for the patient in question.

Specifically, aspects of the present invention provide methods of classifying of patients undergoing treatment for cancer, or participating in a clinical trial, based on the profile constructed from a DNA sample obtained from a tumour in the patient by a method according to the above described aspects, including some, all or none of the optional or preferred features of those aspects as described above.

Further aspects of the present invention provide methods of selecting a patient for a clinical trial of a cancer therapy, the selection being made on the basis of the profile constructed from a DNA sample obtained from a tumour in the patient by a method according to the above described aspects, including some, all or none of the optional or preferred features of those aspects as described above.

Further aspects of the present invention provide a method of classifying patients who have completed a clinical trial or course of treatment, the method including: characterising a DNA sample obtained from a tumour in each of said patients using a method according to the above described aspects, including some, all or none of the optional or preferred features of those aspects; and correlating the interpreted profile obtained for each patient with the clinical outcome of the trial or treatment as well as a method of determining a prognosis of a tumour, the method including characterising a DNA sample obtained from said tumour using a method according to the above described aspects, including some, all or none of the optional or preferred features of those aspects; and determining the prognosis from the interpreted profile.

Genomic Profiling to Characterise Tumour DNA

The complete genomes of 560 breast cancers and non-neoplastic tissue from different individuals (556 female and four male) were sequenced (FIG. 3A). 3,479,652 somatic base substitutions, 371,993 small indels and 77,695 rearrangements were detected, with substantial variation in the number of each between individual samples (FIG. 3B). Transcriptome sequence, microRNA expression, array based copy number and DNA methylation data were obtained from subsets of cases.

To identify new cancer genes, the inventors combined somatic substitutions and indels in protein-coding exons with data from other series [12-15, 26], constituting a total of 1,332 breast cancers, and searched for mutation clustering in each gene beyond that expected by chance. Five cancer genes were found for which evidence was previously absent or equivocal (MED23, FOXP1, MLLT4, XBP1, ZFP36L1), or for which the mutations indicate the gene acts as a recessive cancer gene in breast cancer rather than in a dominant fashion, as previously reported in other cancer types. From published reports on all cancer types (cancer.sanger.ac.uk/census), a list of 727 human cancer genes was compiled. Based on driver mutations found previously, conservative rules were defined for somatic driver base substitutions and indel mutations in each gene and sought mutations conforming to these rules in the 560 breast cancers. 916 likely driver mutations of these classes were identified (FIG. 3B).

To explore the role of genomic rearrangements as driver mutations [16, 18, 19, 27], the inventors sought predicted in-frame fusion genes that might create activated, dominant cancer genes. 1,278 unique and 39 infrequently recurrent in-frame gene fusions were identified. Many of the latter, however, were in regions of high rearrangement density, including amplicons [28] and fragile sites, and their recurrence is likely attributable to chance [27]. Furthermore, transcriptome sequences from 260 cancers did not show expression of these fusions and generally confirmed the rarity of recurrent in-frame fusion genes. By contrast, recurrent rearrangements interrupting the gene footprints of CDKN2A, RB1, MAP3K1, PTEN, MAP2K4, ARID1B, FBXW7, MLLT4 and TP53 were found beyond the numbers expected from local background rearrangement rates, indicating that they contribute to the driver mutation burden of recessive cancer genes. Several other recurrently rearranged genomic regions were observed, including dominantly-acting cancer genes ET/6 and ESR1 without consistent elevation in expression levels, L1-retrotransposition sites [29] and fragile sites.

Incorporation of recurrent copy number changes, including homozygous deletions and amplifications, generated a final tally of 1,628 likely driver mutations in 93 cancer genes. At least one driver was identifiable in 95% of cancers. The 10 most frequently mutated genes were TP53, PIK3CA, MYC, CCND1, PTEN, ERBB2, chr8:ZNF703/FGFR1 locus, GATA3, RB1 and MAP3K1 (FIG. 3B, FIG. 8) and accounted for 62% of drivers.

Recurrent Somatic Mutations in Non-Coding Genomic Regions

Figure 2:
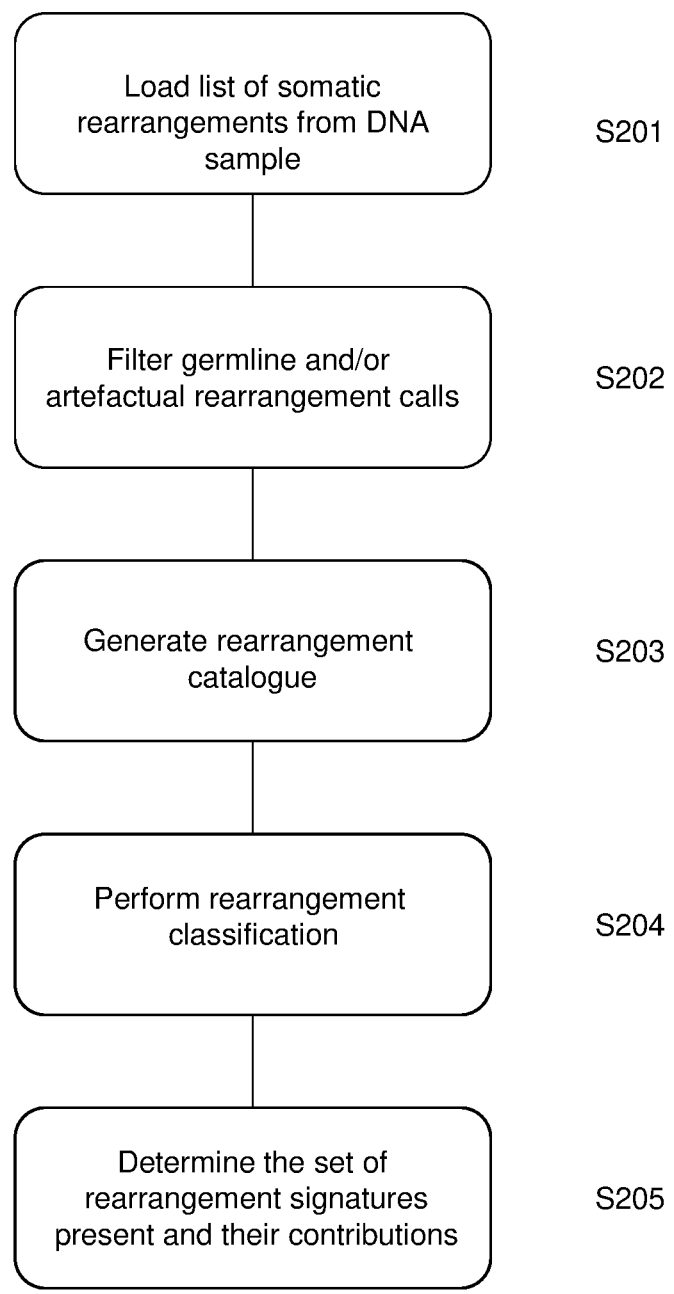
FIG. 2 is a flow diagram showing, in schematic form, steps S201-S205 of a method of determining the likelihood of a DNA sample being HR-deficient or not.
Figure 4A:
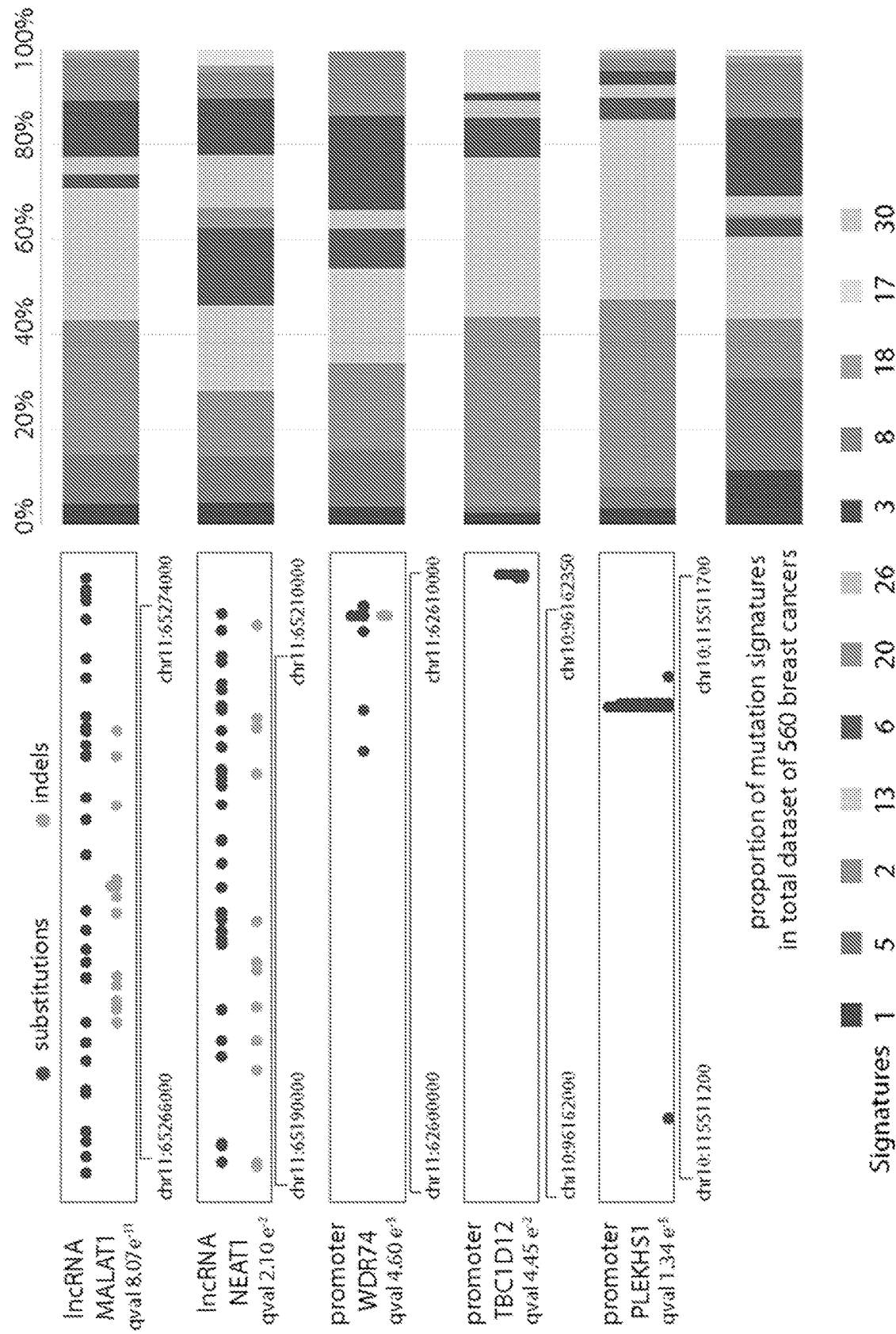
FIGS. 4A-4C show non-coding analyses of breast cancer genomes.

To investigate non-coding somatic driver substitutions and indels, the inventors searched for non-coding genomic regions with more mutations than expected by chance (FIG. 4A, FIG. 9). The promoter of PLEKHS1 (pleckstrin homology domain containing, family S member 1) exhibited recurrent mutations at two genomic positions [30] (FIG. 2A), the underlined bases in the sequence CAGCAAGC TGAACA GCTTGCTG (as previously reported [30]). The two mutated bases are flanked on either side by 9 bp of palindromic sequence forming inverted repeats [31]. Most cancers with these mutations showed many base substitutions of mutational signatures 2 and 13 that have been attributed to activity of APOBEC DNA-editing proteins that target the TCN sequence motif. One of the mutated bases is a cytosine in a TCA sequence context (shown above as the reverse complement, TGA) at which predominantly C>T substitutions were found. The other is a cytosine in ACA context which showed both C>T and C>G mutations.

Figure 4B:
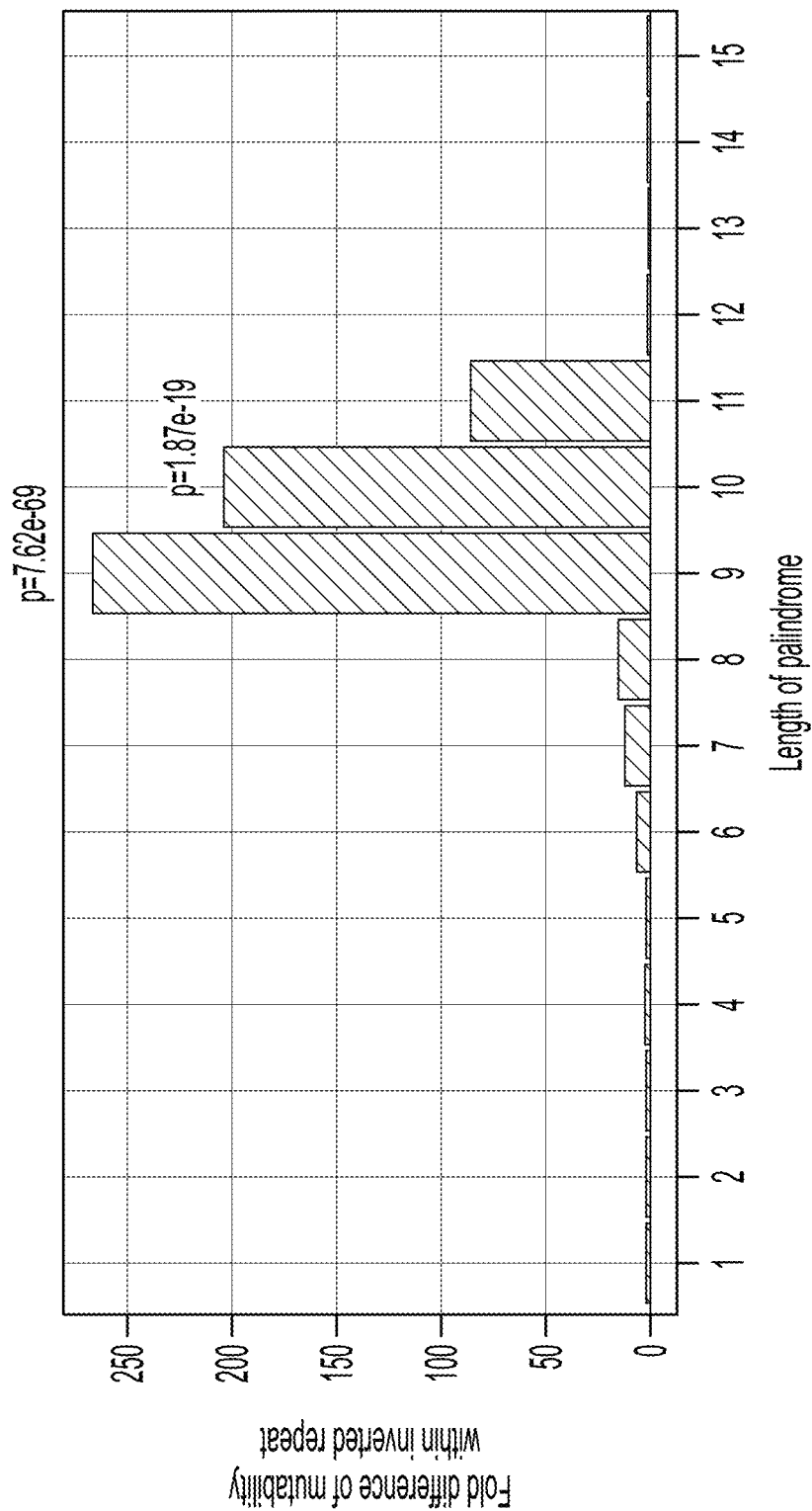
Figure 4C:
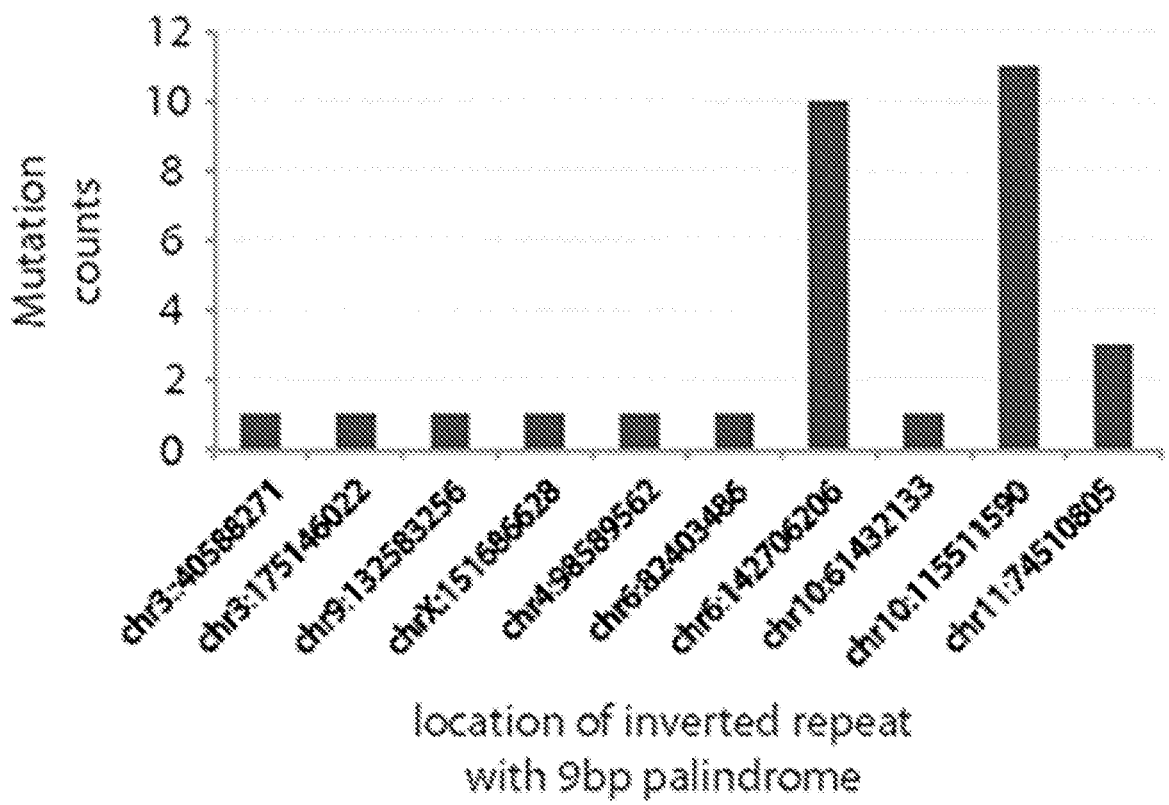

The TGAACA core sequence was mutated at the same two positions at multiple locations elsewhere in the genome (FIG. 4B) where the TGAACA core was also flanked by palindromes (inverted repeat), albeit of different sequences and lengths (FIG. 4B). These mutations were also usually found in cancers with many signature 2 and 13 mutations (FIG. 4A). TGAACA core sequences with longer flanking palindromes generally exhibited a higher mutation rate, and TGAACA sequences flanked by 9 bp palindromes exhibited a ~265-fold higher mutation rate than sequences without them (FIG. 4C). However, additional factors must influence the mutation rate because it varied markedly between TGAACA core sequences with different palindromes of the same length (FIG. 4D). Some TGAACA-inverted repeat sites were in regulatory regions but others were intronic or intergenic without functional annotation (examples in FIG. 4B) or exonic. The propensity for mutation recurrence at specific positions in a distinctive sequence motif in cancers with numerous mutations of particular signatures renders it plausible that these are hypermutable hotspots [32-34], perhaps through formation of DNA hairpin structures [35], which are single stranded at their tips enabling attack by APOBEC enzymes, rather than driver mutations.

Two recurrently mutated sites were also observed in the promoter of TBC1D12 (TBC1 domain family, member 12) (q-value $4.5e^{-2}$) (FIG. 4A). The mutations were characteristic of signatures 2 and 13 and enriched in cancers with many signature 2 and 13 mutations (FIG. 4A). The mutations were within the TBC1D12 Kozak consensus sequence (CCCCAGATGGTGGG)) shifting it away from the consensus [36]. The association with particular mutational signatures suggests that these may also be in a region of hypermutability rather than drivers.

The WDR74 (WD repeat domain 74) promoter showed base substitutions and indels (q-value $4.6e^{-3}$) forming a cluster of overlapping mutations (FIG. 4A) [20]. Coding sequence driver mutations in WDR74 have not been reported. No differences were observed in WDR74 transcript levels between cancers with WDR74 promoter mutations compared to those without. Nevertheless, the pattern of this non-coding mutation cluster, with overlapping and different mutation types, is more compatible with the possibility of the mutations being drivers.

Two long non-coding RNAs, MALAT1 (q-value $8.7e^{-11}$, as previously reported [12]) and NEAT1 (q-value $2.1e^{-2}$) were enriched with mutations. Transcript levels were not significantly different between mutated and non-mutated samples. Whether these mutations are drivers, or result from local hypermutability, is unclear.

Mutational Signatures

Figure 5A:
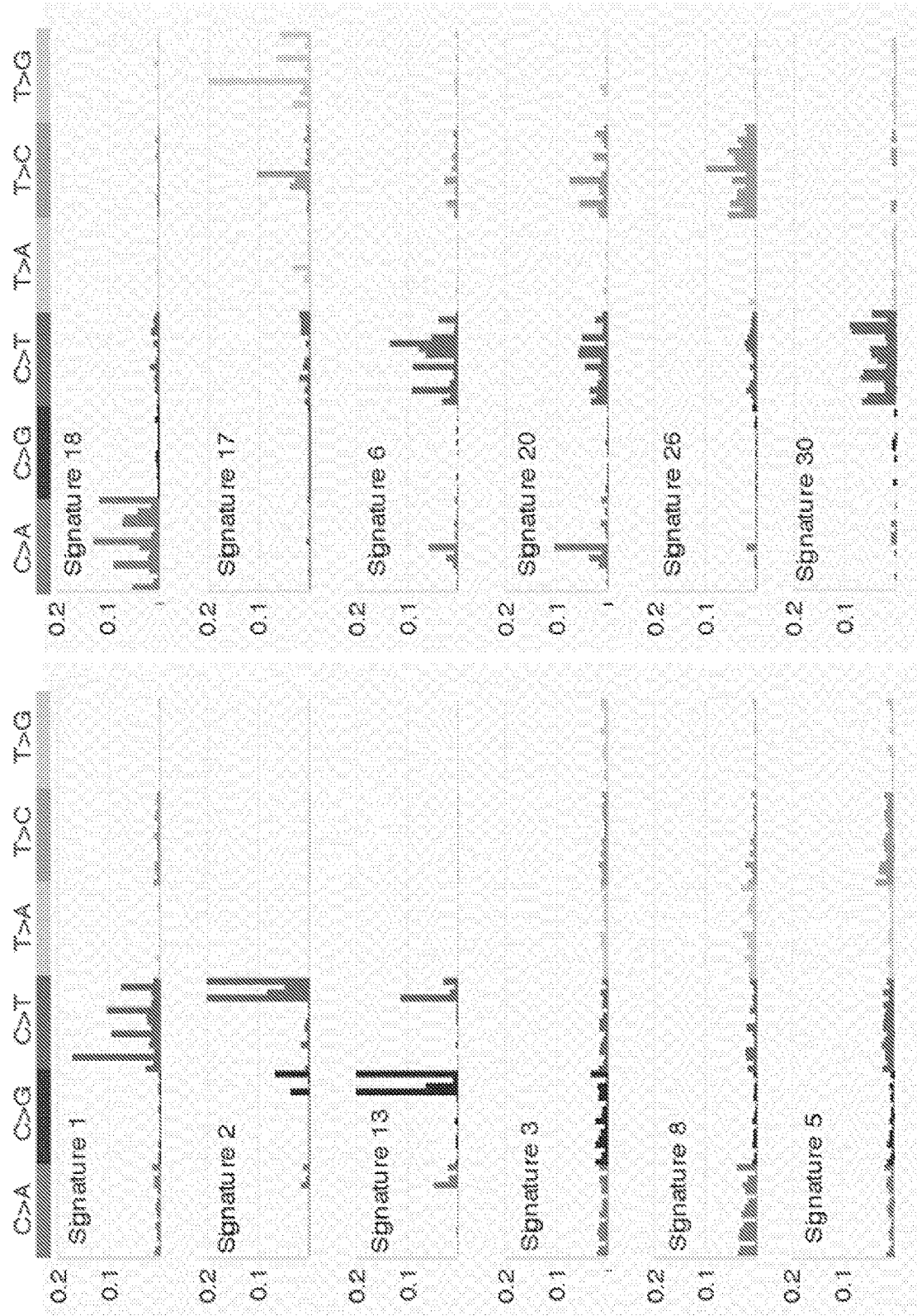
FIGS. 5A-5C show the extraction and contributions of base substitution signatures in 560 breast cancers.
Figure 5B:
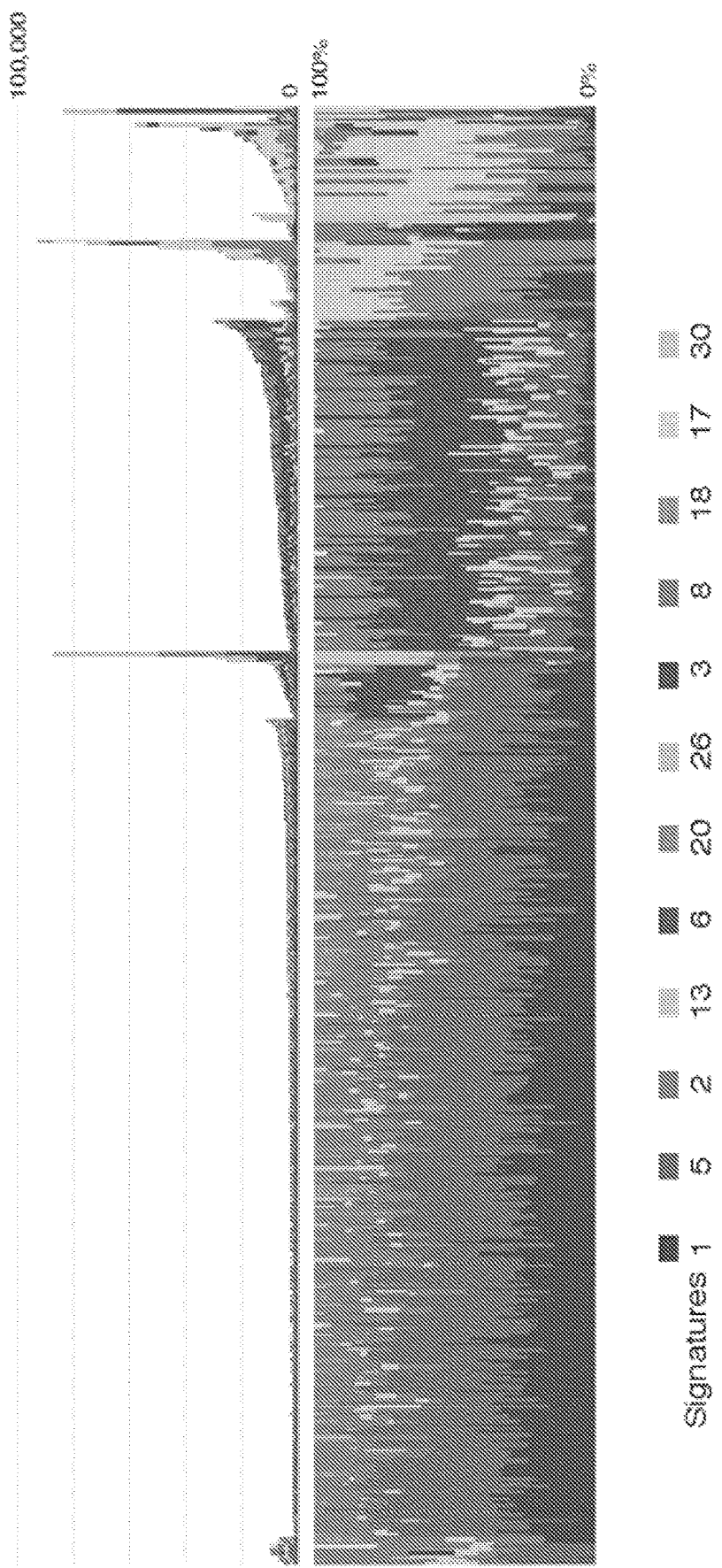
Figure 6B:
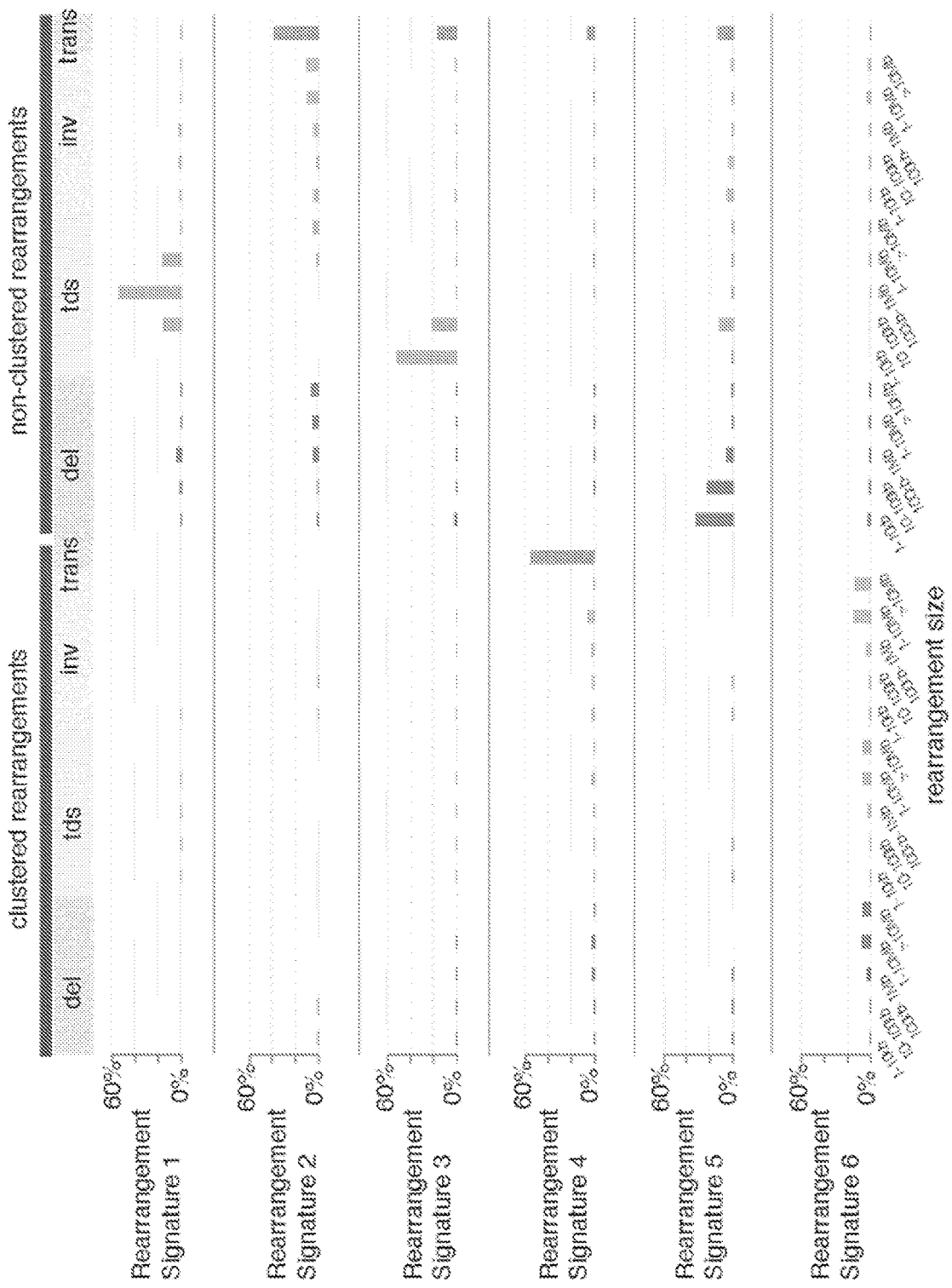

Mutational processes generating somatic mutations imprint particular patterns of mutations on cancer genomes, termed signatures [2, 24, 37]. Applying a mathematical approach [25] to extract mutational signatures previously revealed five base substitution signatures in breast cancer; signatures 1, 2, 3, 8 and 13 [2, 24]. Using this method in the 560 cases revealed 12 signatures, including those previously observed and a further seven, of which five have formerly been detected in other cancer types (signatures 5, 6, 17, 18 and 20) and two are new (signatures 26 and 30) (FIG. 5A-B, FIG. 6A). Two indel signatures were also found [2, 24].

In embodiments of the present invention, detection of the presence of base substitution signatures in a DNA sample obtained from a tumour is carried out using the methods disclosed in [58].

Signatures of rearrangement mutational processes have not previously been formally investigated. To enable this we adopted a rearrangement classification incorporating 32 subclasses. In many cancer genomes, large numbers of rearrangements are regionally clustered, for example in zones of gene amplification. Therefore, the rearrangements were first classified into those inside and outside clusters, further subclassified into deletions, inversions and tandem duplications, and then according to the size of the rearranged segment. The final category in both groups was interchromosomal translocations.

Figure 7:
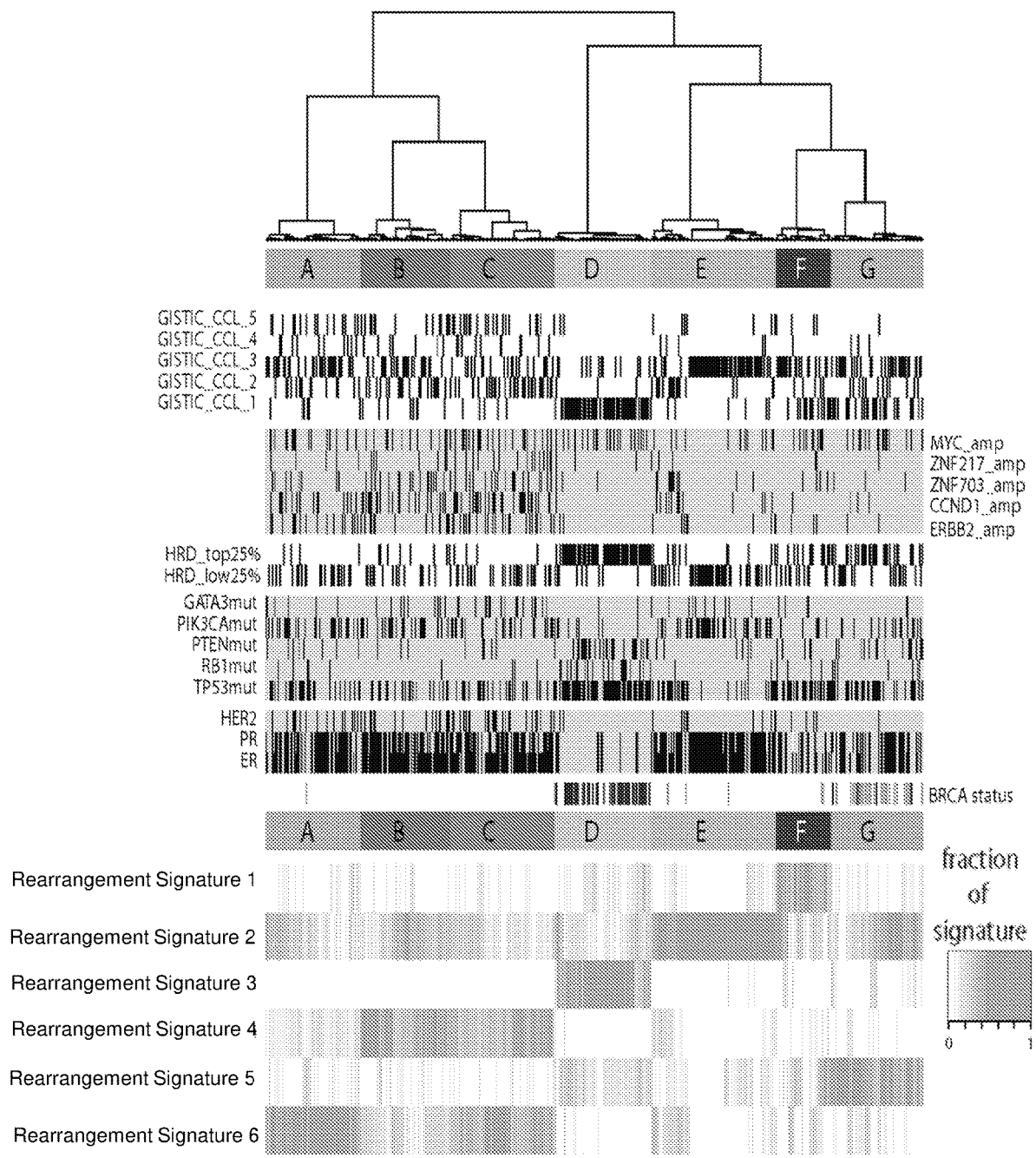
FIG. 7 shows the rearrangement signatures in the 560 breast cancers as a heatmap of rearrangement signatures (RS) following unsupervised hierarchical clustering based on proportions of RS in each cancer; 7 cluster groups (A-G) were noted and relationships with expression (AIMS) subtype, immunohistopathology status (ER, PR, HER2 status—black=positive), abrogation of BRCA1 and BRCA2 (whether germline, somatic or through promoter hypermethylation), presence of 3 or more foci of kataegis (black=positive), HRD index (top 25% or lowest 25%—black=positive), GISTIC cluster group (black=positive) and driver mutations in cancer genes and miRNA cluster groups with the contribution of base substitution signatures in these 7 cluster groups provided in the lowermost panel.
Figure 8A:
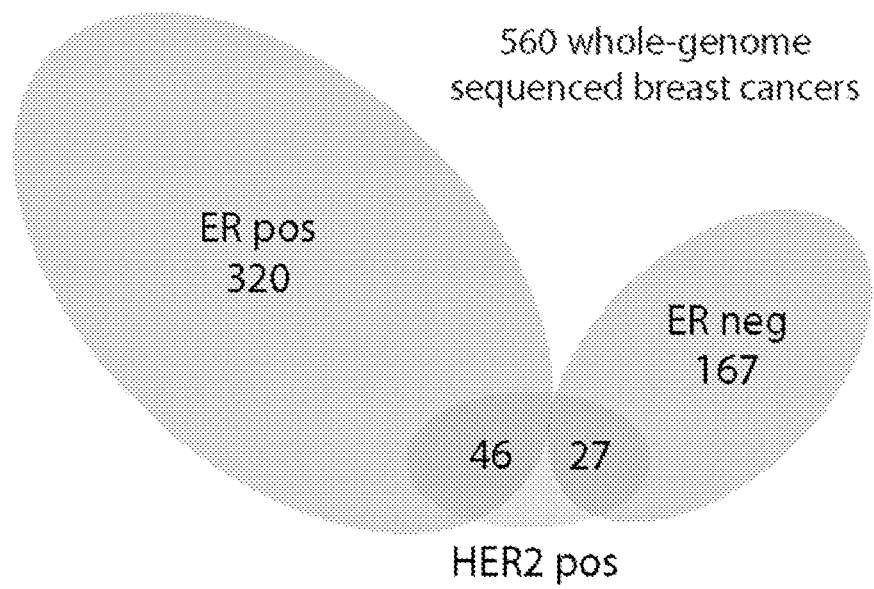
FIGS. 8A-8D show a landscape of driver mutations.
Figure 8B:
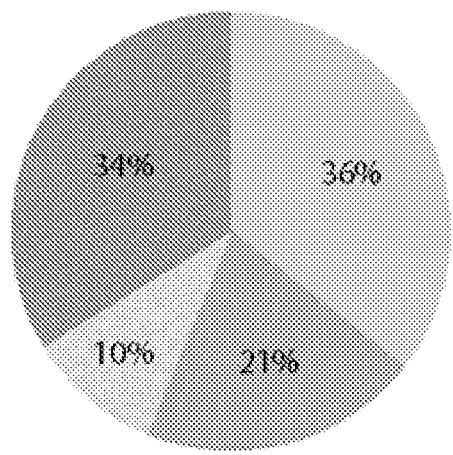
Figure 8B:
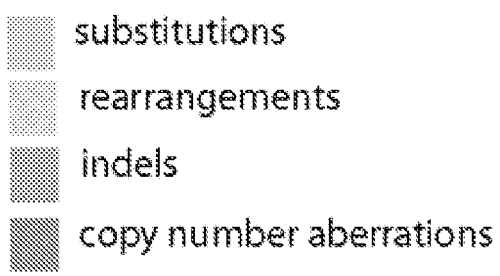
Figure 8C:
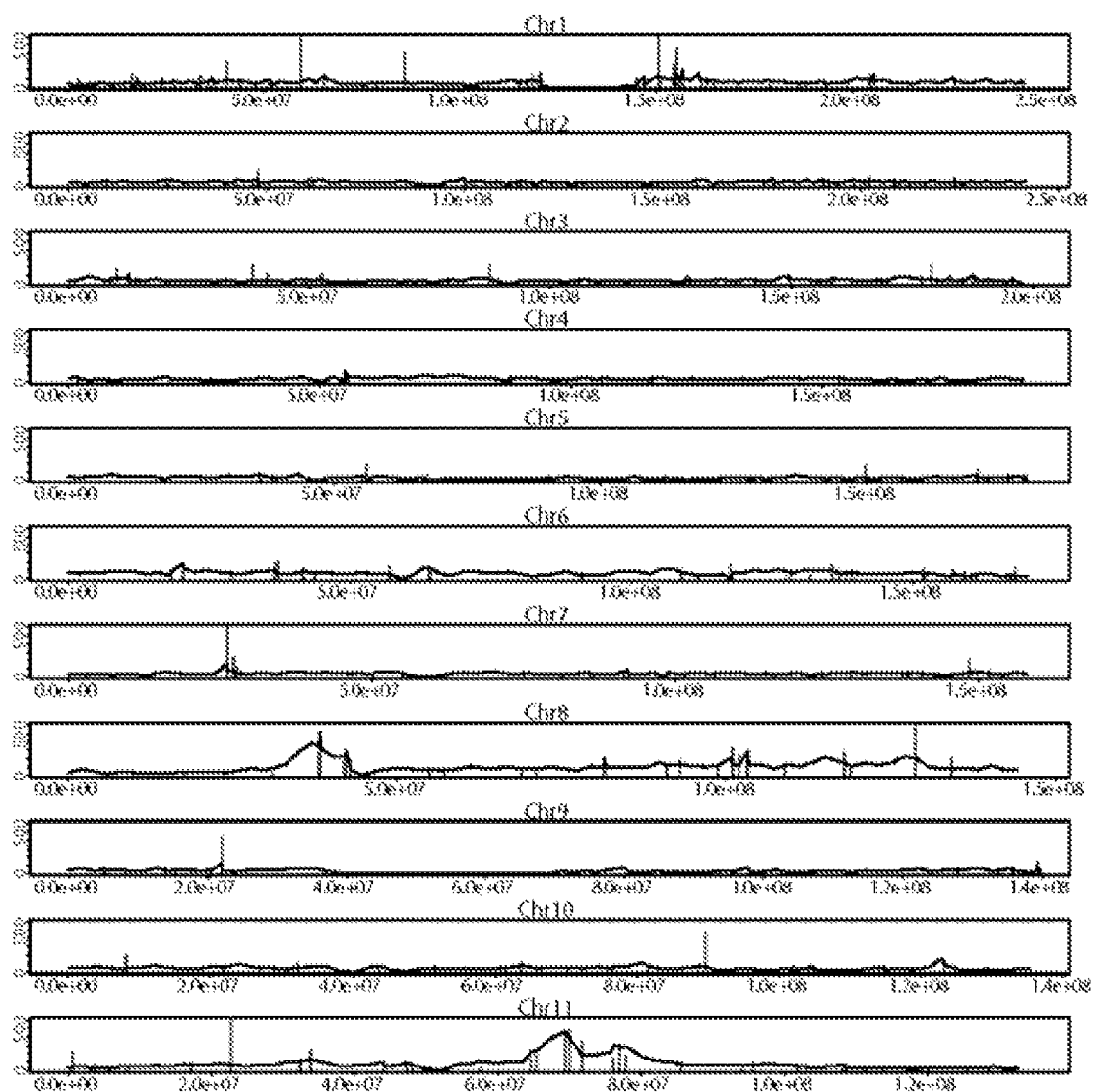
Figure 8D:
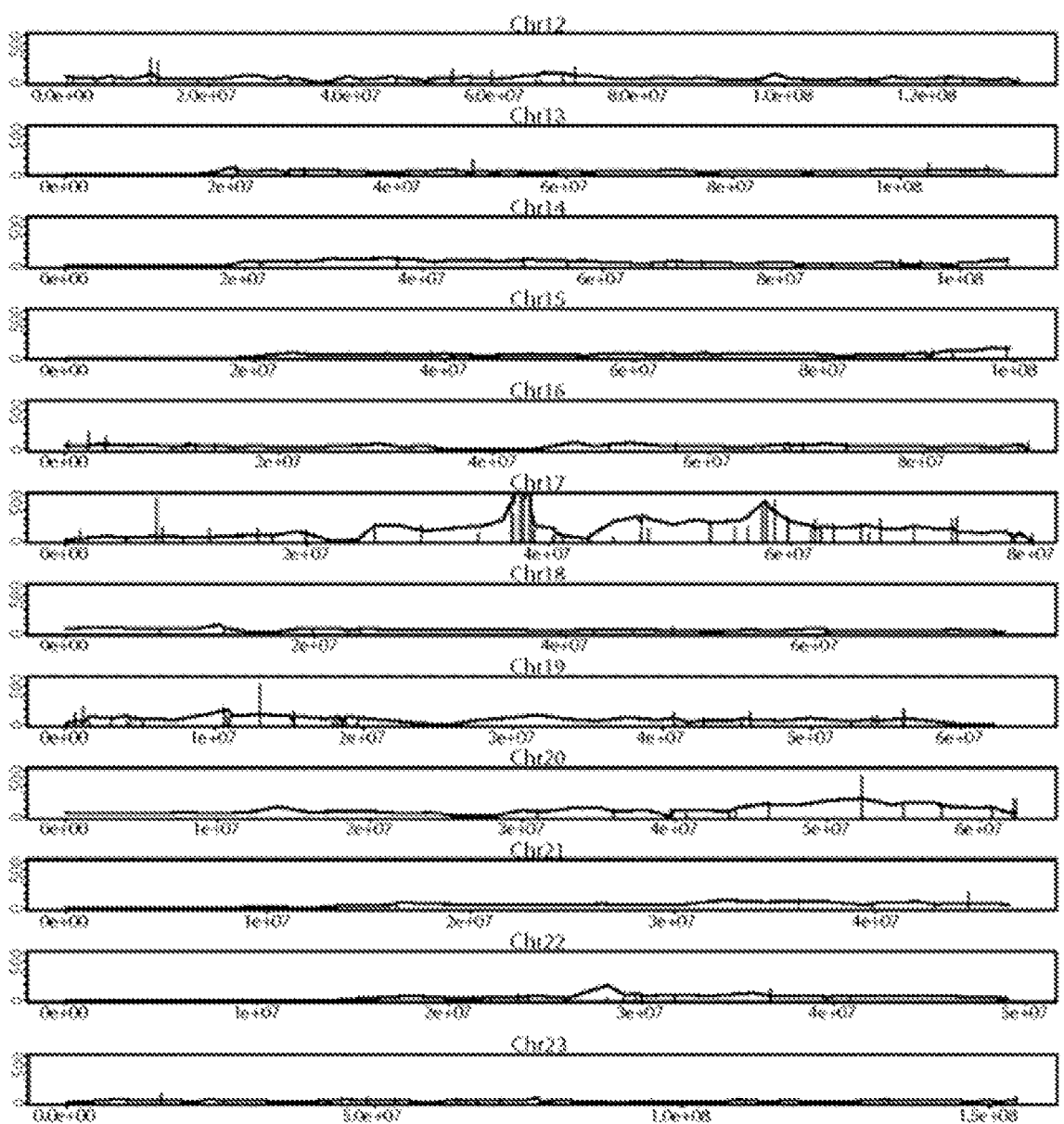

Application of the mathematical framework used for base substitution signatures [2, 24, 25] extracted six rearrangement signatures (FIG. 7A). Unsupervised hierarchical clustering on the basis of the proportion of rearrangements attributed to each signature in each breast cancer yielded seven major subgroups exhibiting distinct associations with other genomic, histological or gene expression features.

Rearrangement Signature 1 (9% of all rearrangements) and Rearrangement Signature 3 (18% rearrangements) were characterised predominantly by tandem duplications (FIG. 7A). Tandem duplications associated with Rearrangement Signature 1 were mostly >100 kb (FIG. 7B), and those with Rearrangement Signature 3<10 kb (FIG. 7C). More than 95% of Rearrangement Signature 3 tandem duplications were concentrated in 15% of cancers (Cluster D, FIG. 8), many with several hundred rearrangements of this type. Almost all cancers (91%) with BRCA1 mutations or promoter hypermethylation were in this group, which was enriched for basal-like, triple negative cancers and copy number classification of a high Homologous Recombination Deficiency (HRD) index [38-40]. Thus, inactivation of BRCA1, but not BRCA2, may be responsible for the Rearrangement Signature 3 small tandem duplication mutator phenotype.

More than 35% of Rearrangement Signature 1 tandem duplications were found in just 8.5% of the breast cancers and some cases had hundreds of these (Cluster F, FIG. 8). The cause of this large tandem duplication mutator phenotype (FIG. 7B) is unknown. Cancers exhibiting it are frequently TP53-mutated, relatively late diagnosis, triple-negative breast cancers, showing enrichment for base substitution signature 3 and a high Homologous Recombination Deficiency (HRD) index (FIG. 8) but do not have BRCA1/2 mutations or BRCA1 promoter hypermethylation.

Figure 10B:
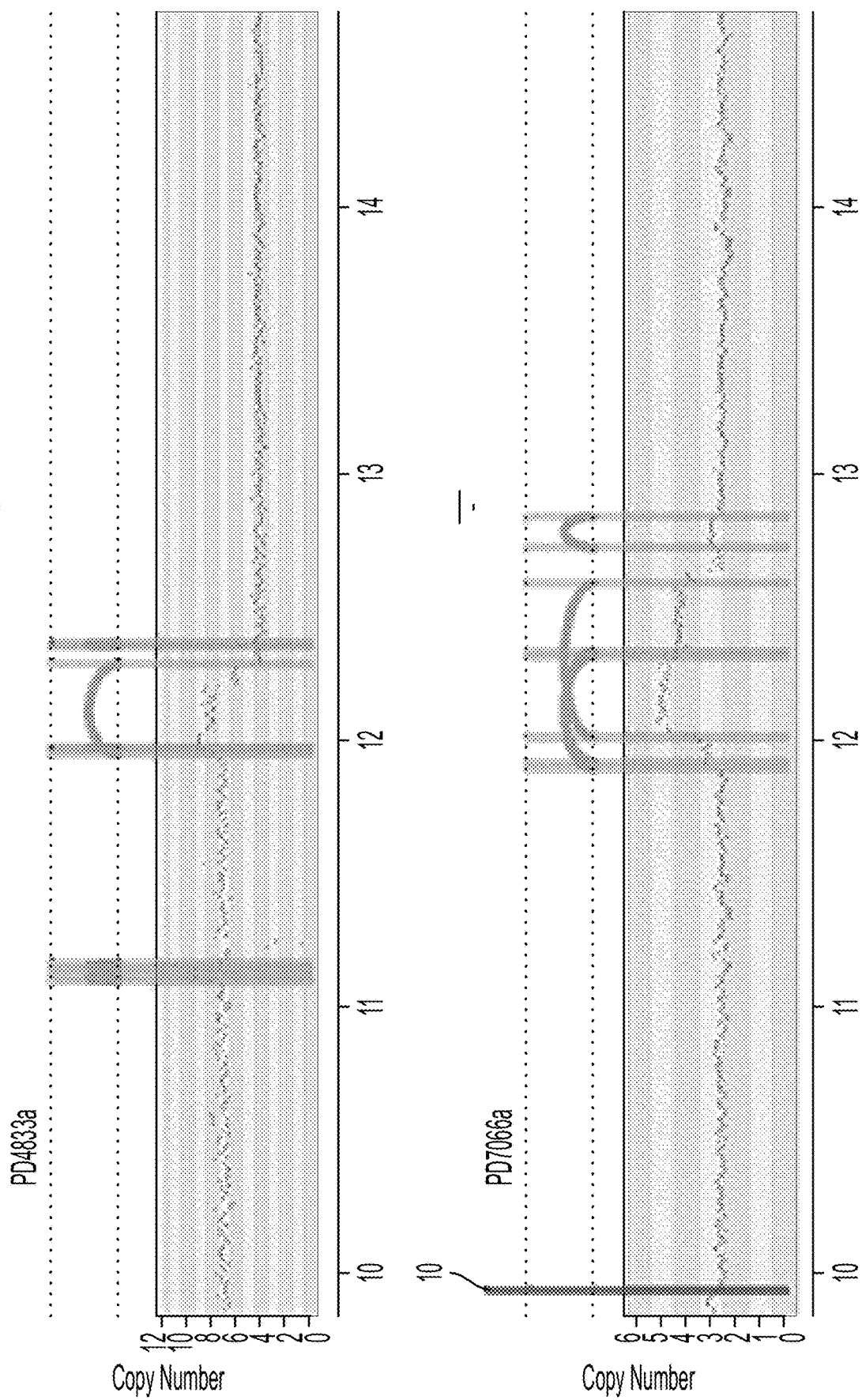
Figure 10D:
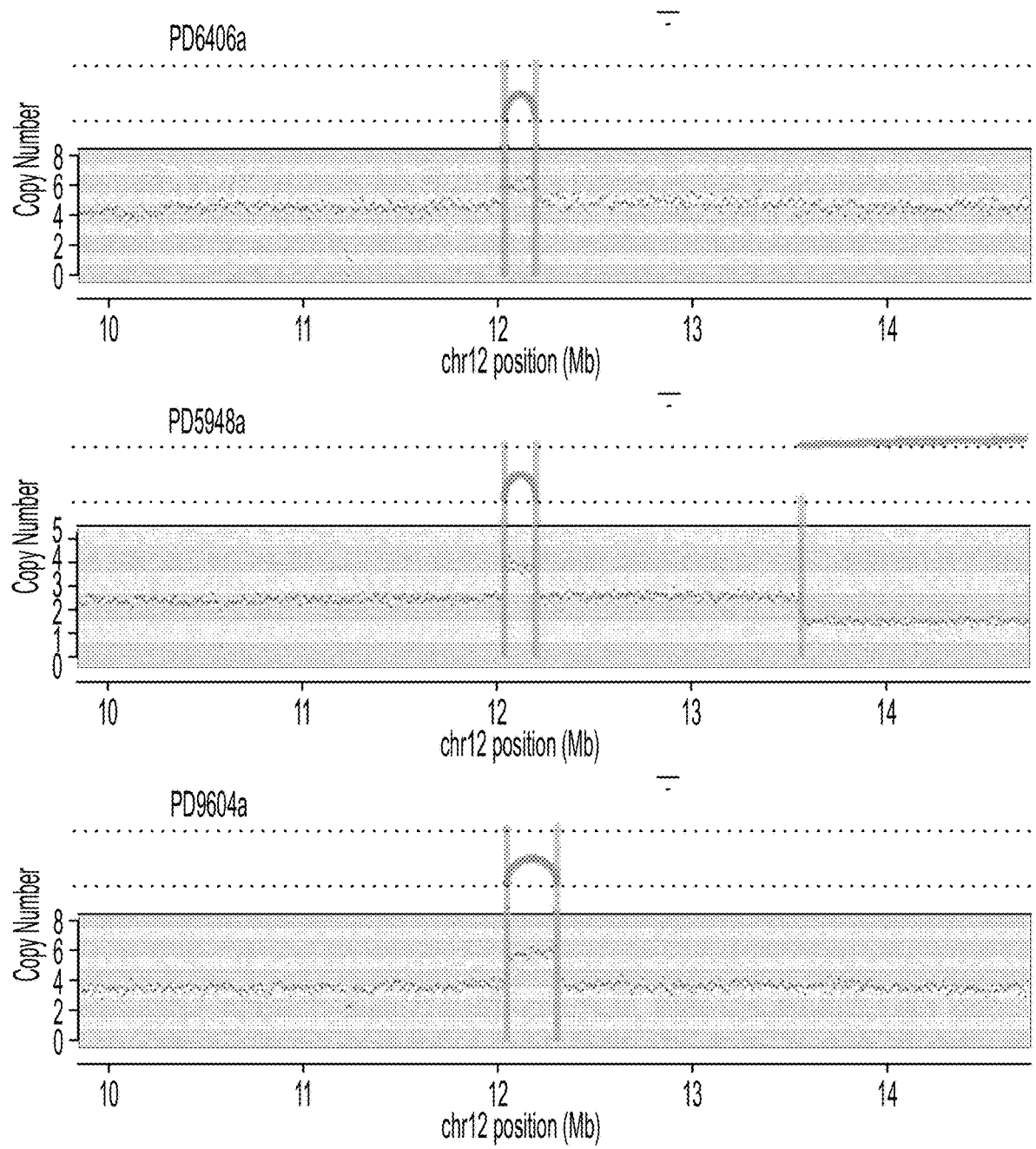
Figure 11A:
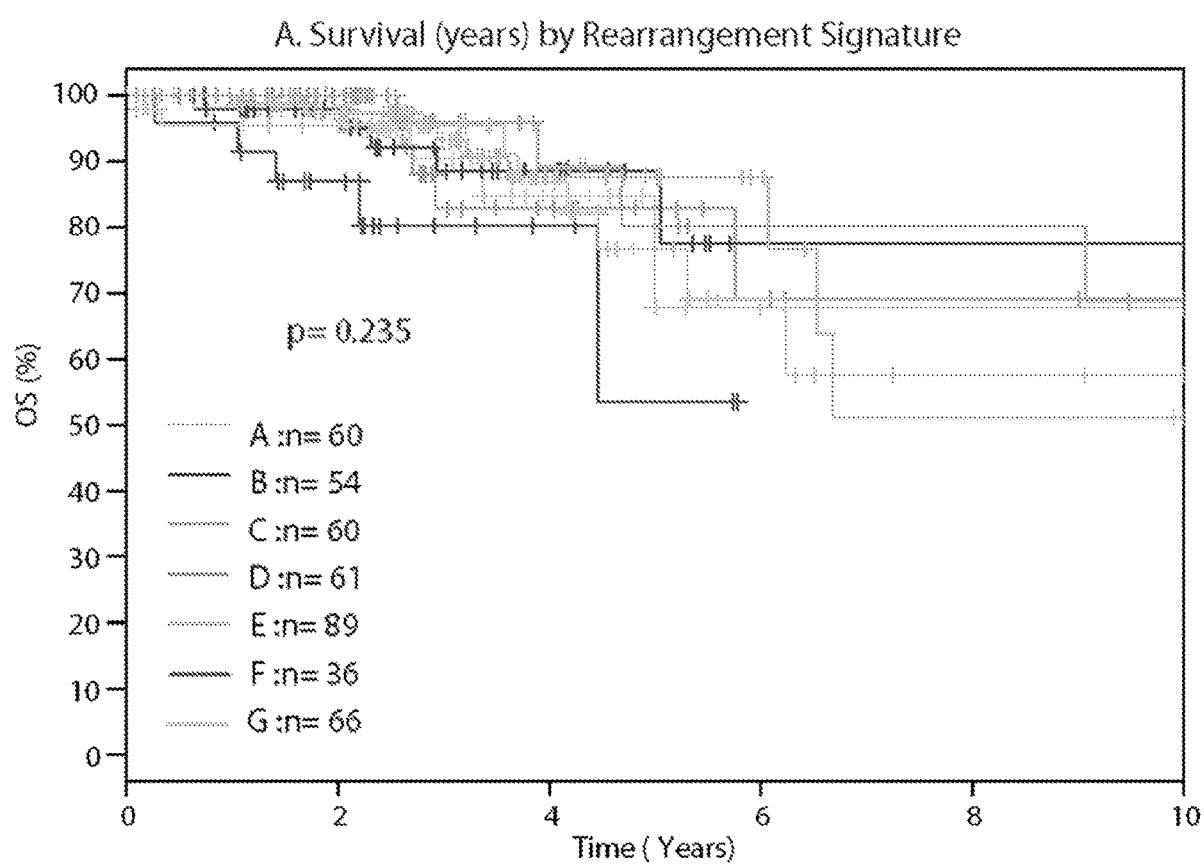
FIGS. 11A-11G show the rearrangement cluster groups and associated features, including FIG. 11A, overall survival by rearrangement cluster group.
Figure 11B:
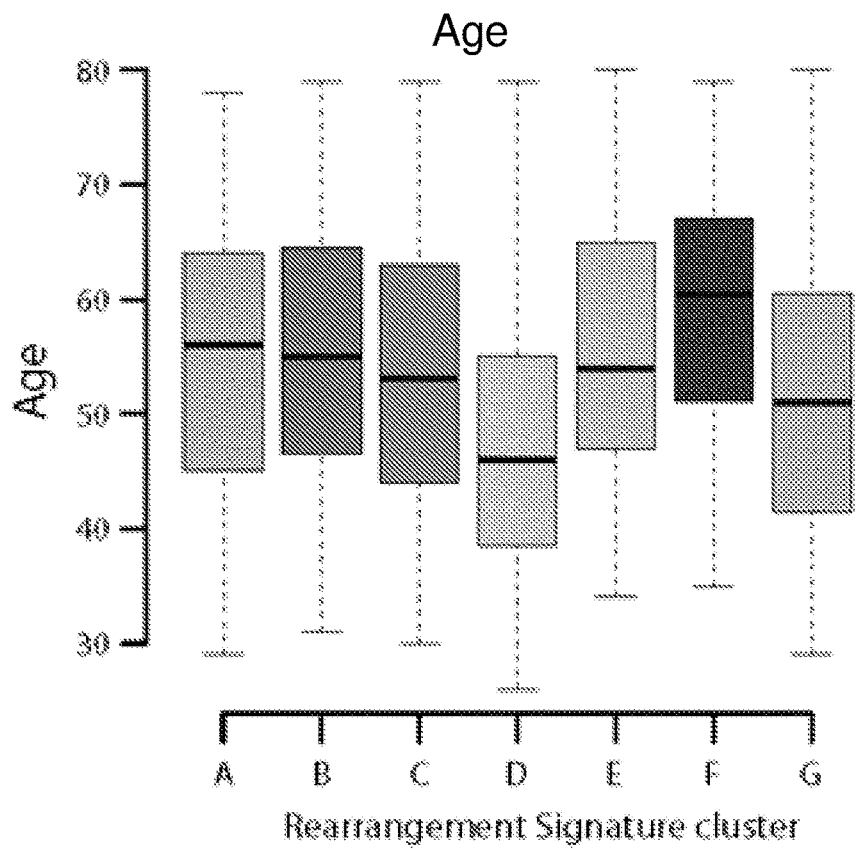
Figure 11C:
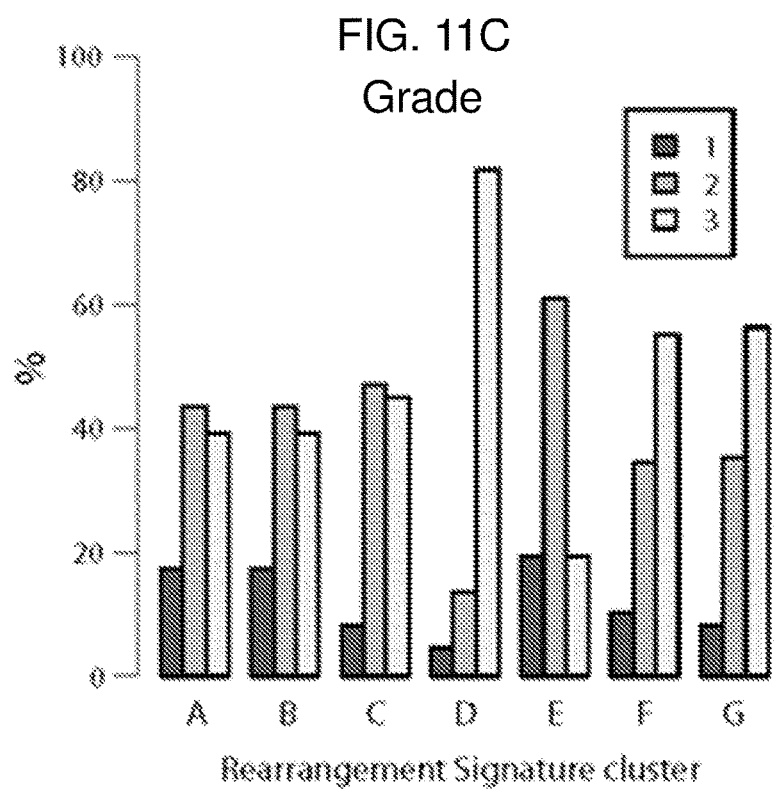
Figure 11D:
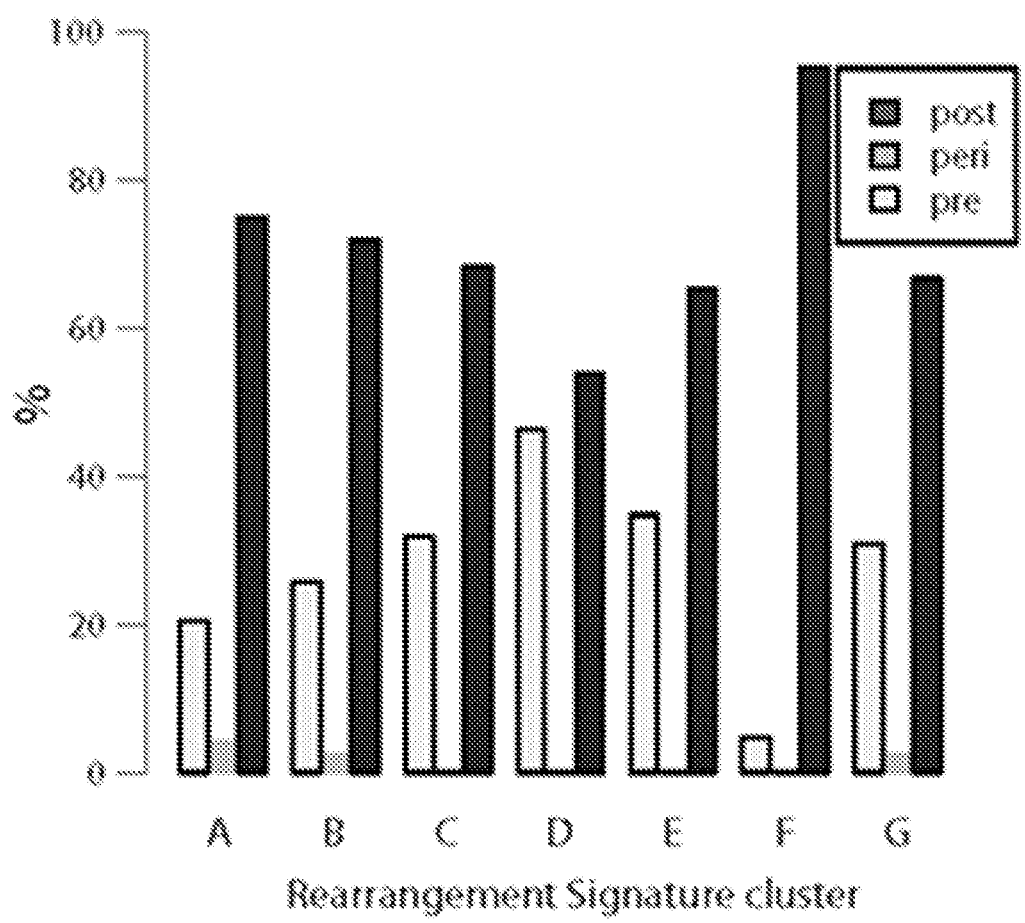
Figure 11E:
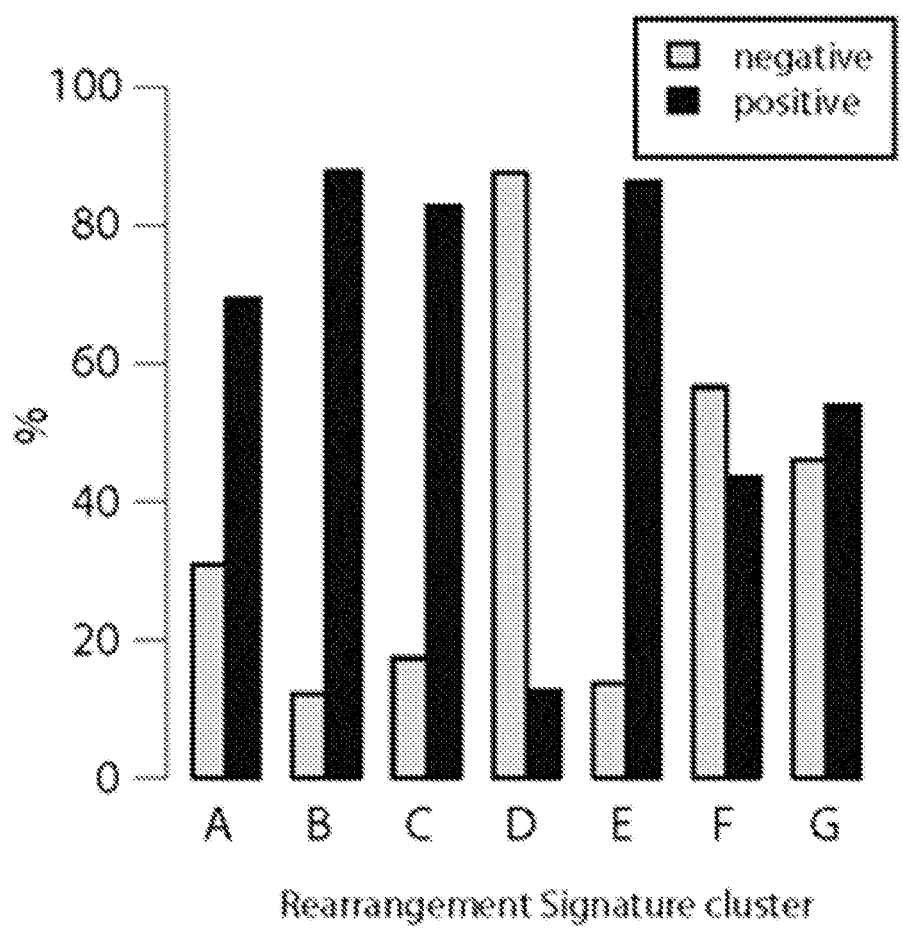
Figure 11F:
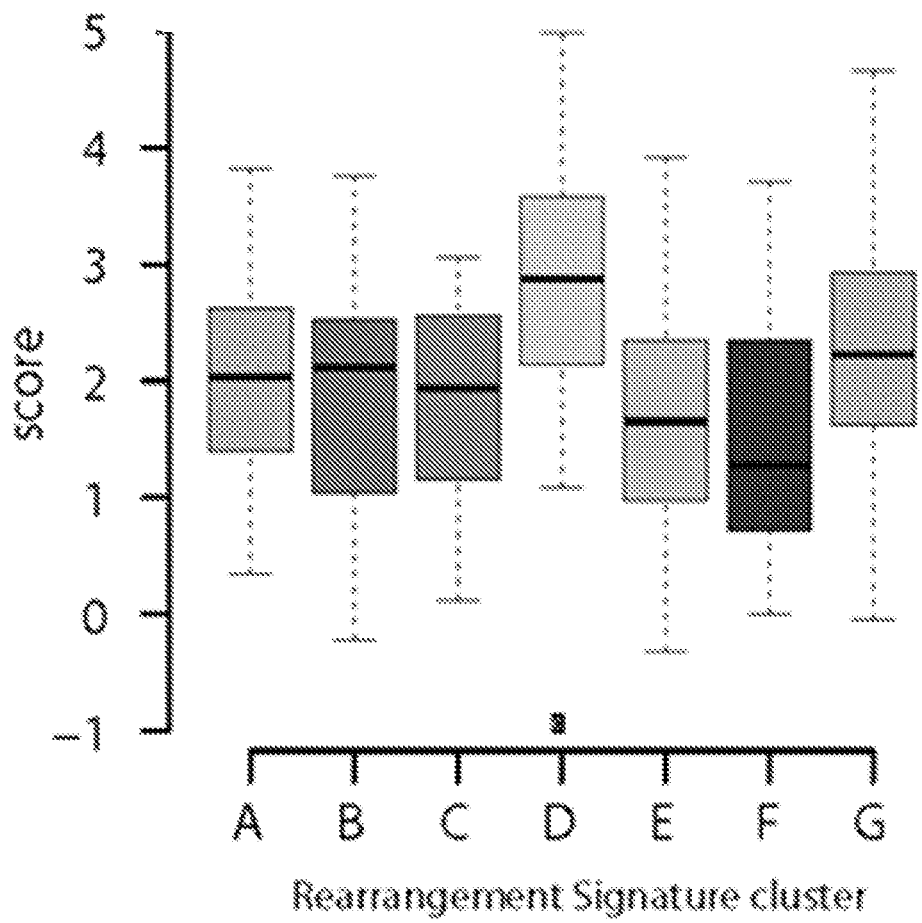
Figure 11G:
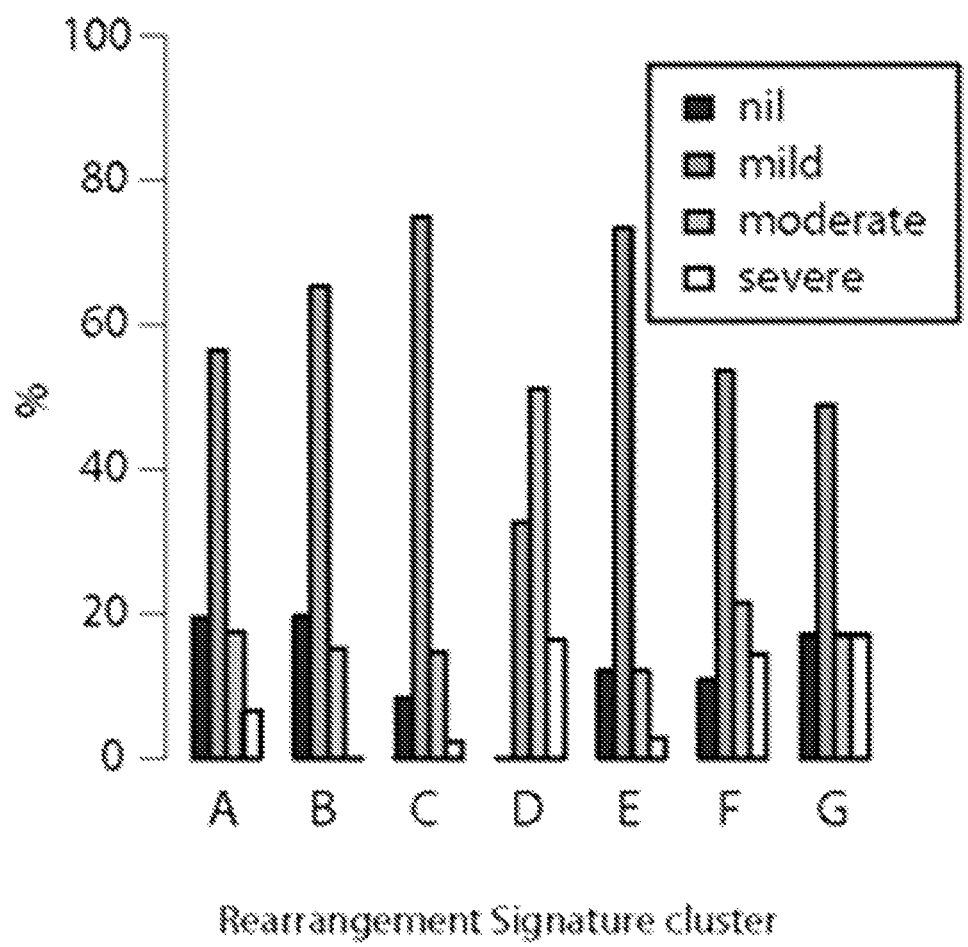

Rearrangement Signature 1 (FIG. 7B) and 3 (FIG. 7C) tandem duplications were generally evenly distributed over the genome. However, there were nine locations at which recurrence of tandem duplications was found across the breast cancers and which often showed multiple, nested tandem duplications in individual cases (FIG. 10). These may be mutational hotspots specific for these tandem duplication mutational processes although we cannot exclude the possibility that they represent driver events.

Rearrangement Signature 5 (accounting for 14% rearrangements) was characterised by deletions <100 kb. It was strongly associated with the presence of BRCA1 mutations or promoter hypermethylation (Cluster D, FIG. 8, BRCA2 mutations (Cluster G, FIG. 8) and with Rearrangement Signature 1 large tandem duplications (Cluster F, FIG. 8).

Rearrangement Signature 2 (accounting for 22% rearrangements) was characterised by non-clustered deletions (>100 kb), inversions and interchromosomal translocations, was present in most cancers but was particularly enriched in ER positive cancers with quiet copy number profiles (Cluster E, GISTIC Cluster 3, FIG. 8). Rearrangement Signature 4 (accounting for 18% of rearrangements) was characterised by clustered interchromosomal translocations while Rearrangement Signature 6 (19% of rearrangements) by clustered inversions and deletions (Clusters A, B, C, FIG. 8).

Figure 12A:
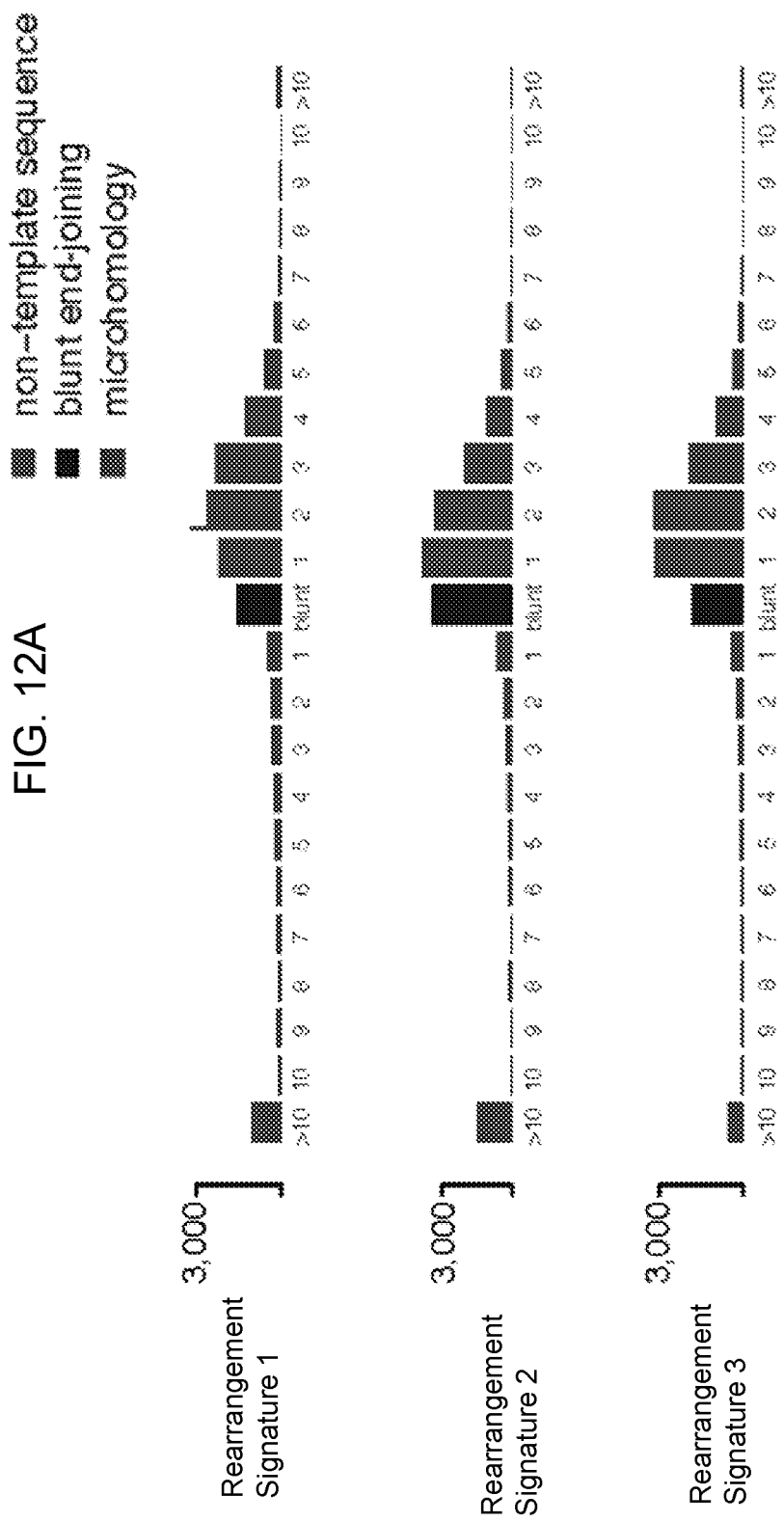
Figure 12C:
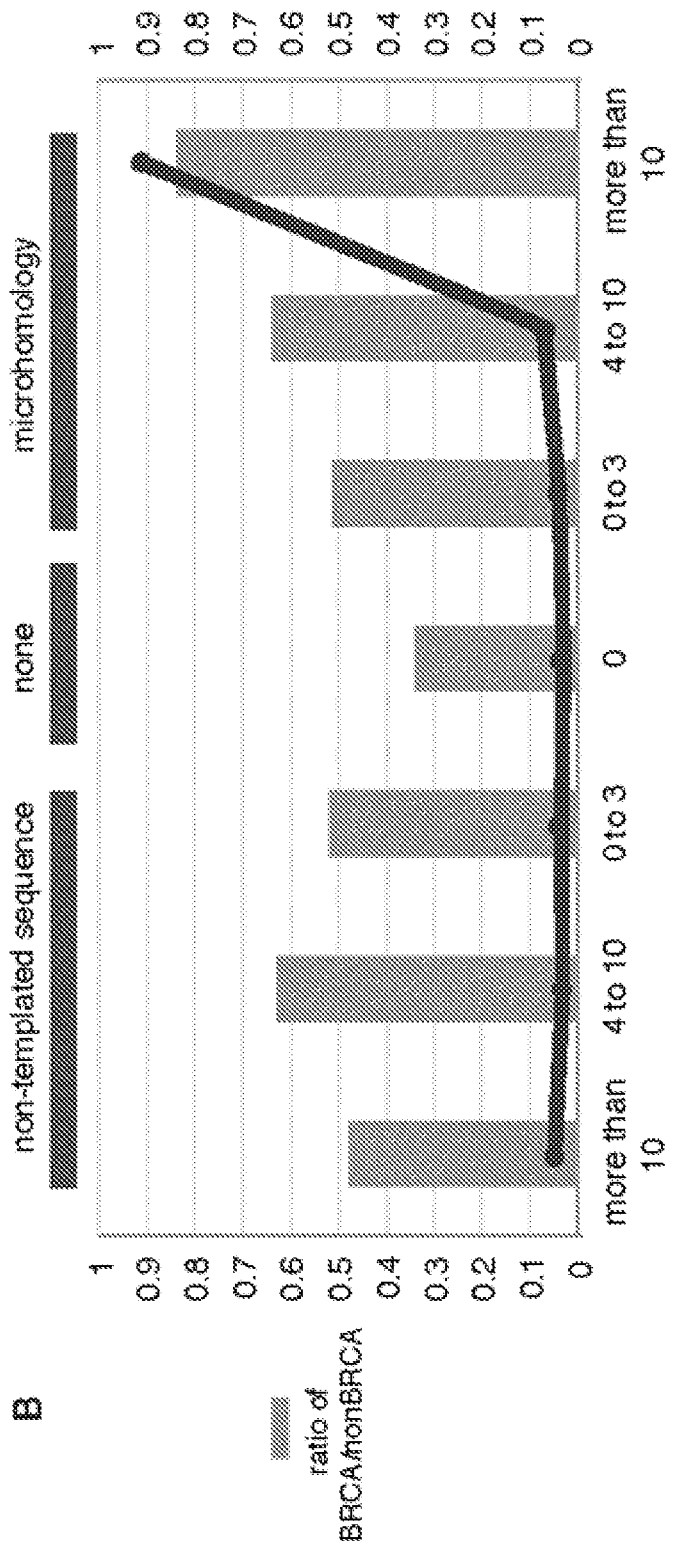
Figure 13B:
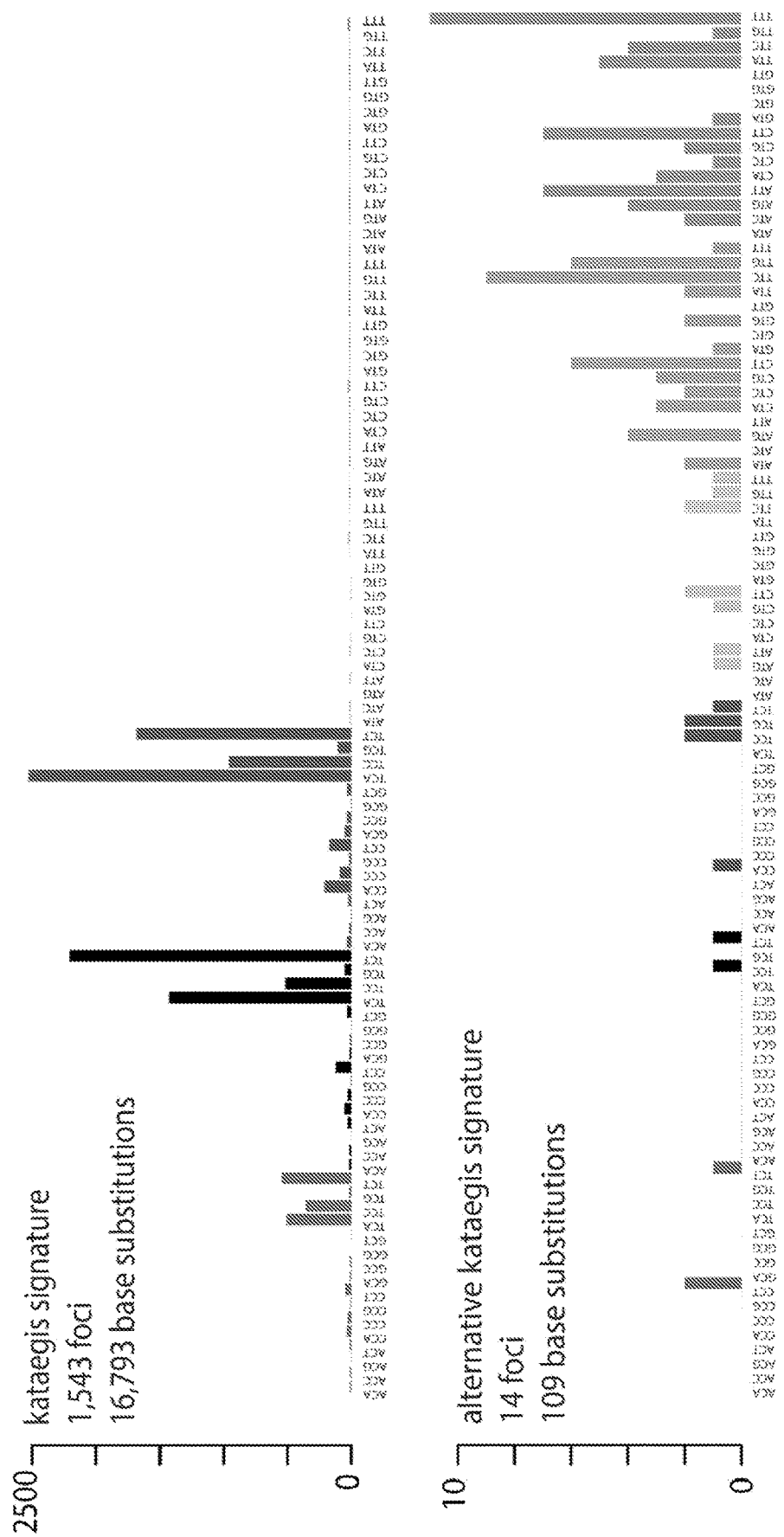

Short segments (1-5 bp) of overlapping microhomology characteristic of alternative methods of end joining repair were found at most rearrangements [2, 14]. Rearrangement Signatures 2, 4 and 6 were characterised by a peak at 1 bp of microhomology while Rearrangement Signatures 1, 3 and 5, associated with homologous recombination DNA repair deficiency, exhibited a peak at 2 bp (FIG. 12). Thus, different end-joining mechanisms may operate with different rearrangement processes. A proportion of breast cancers showed Rearrangement Signature 5 deletions with longer (>10 bp) microhomologies involving sequences from short-interspersed nuclear elements (SINEs), most commonly AluS (63%) and AluY (15%) family repeats (FIG. 12). Long segments (more than 10 bp) of non-templated sequence were particularly enriched amongst clustered rearrangements.

As a result of the above, a method for determining the number of rearrangements detected in a DNA sample which are associated with a particular rearrangement signature has also been developed, as set out in more detail in PCT/EP2017/060279, the contents of which are hereby incorporated by reference. In embodiments of the present invention, the detection of rearrangement signatures in a DNA sample from a tumour are carried out according to the methods set out in that application.

Microhomology-Mediated Indels

The determination of the presence or absence of microhomology-mediated indels (also called "microhomology-mediated deletions" as, of the overall range of insertions and deletions, only deletions are ever classified as microhomology-mediated) can be performed as follows.

First, indels are identified using cgpPindel, as described in [59] and [60].

For each insertion/deletion (indel), more than or equal to 25 bp of flanking sequence is identified using the Ensembl API.

Only deletions are taken into consideration for the rest of the analysis. If the first few nucleotides but not all of the nucleotides of the deletion motif matches the first few nucleotides of the immediate 3' flanking sequence, then this is referred to as "microhomology-mediated deletion" or "microhomology-mediated indel".

Localised Hypermutation: Kataegis

Focal base substitution hypermutation, termed kataegis, is generally characterised by substitutions with characteristic features of signatures 2 and 13 [2, 24]. Kataegis was observed in 49% breast cancers, with 4% exhibiting 10 or more foci. Kataegis colocalises with clustered rearrangements characteristic of rearrangement signatures 4 and 6 (FIG. 8). Cancers with tandem duplications or deletions of rearrangement signatures 1, 3 and 5 did not usually demonstrate kataegis. However, there must be additional determinants of kataegis since only 2% of rearrangements are associated with it. A rare (14/1,557 foci, 0.9%), alternative form of kataegis colocalising with rearrangements but with a base substitution pattern characterised by T>G and T>C mutations predominantly at NTT and NTA sequences was also observed. This pattern of base substitutions most closely matches Signature 9 (cancer.sanger.ac.uk/cosmic/signatures), previously observed in B lymphocyte neoplasms and attributed to polymerase eta activity [41].

Mutational Signatures Associated with BRCA1 and BRCA2 Mutations

Of the 560 breast cancers, 90 had germline (60) or somatic (14) inactivating mutations in BRCA1 (35) or BRCA2 (39) or showed methylation of the BRCA1 promoter (16). Loss of the wild-type chromosome 17 or 13 was observed in 80/90 cases. The latter exhibited many base substitution mutations of signature 3, accompanied by deletions of >3 bp with microhomology at rearrangement breakpoints, and signature 8 together with CC>AA double nucleotide substitutions. Cases in which the wild type chromosome 17 or 13 was retained did not show these signatures. Thus signature 3 and, to a lesser extent, signature 8 are associated with absence of BRCA1 and BRCA2 functions.

Cancers with inactivating BRCA1 or BRCA2 mutations usually carry many genomic rearrangements. Cancers with BRCA1, but not BRCA2, mutations exhibit large numbers of Rearrangement Signature 3 small tandem duplications. Cancers with BRCA1 or BRCA2 mutations show substantial numbers of Rearrangement Signature 5 deletions. No other Rearrangement Signatures were associated with BRCA1 or BRCA2 null cases. Some breast cancers without identifiable BRCA1/2 mutations or BRCA1 promoter methylation showed these features and segregated with BRCA1/2 null cancers in hierarchical clustering analysis (FIG. 8). In such cases, the BRCA1/2 mutations may have been missed or other mutated or promoter methylated genes may be exerting similar effects (Please see cancer.sanger.ac.uk/cosmic/sample/genomes for examples of whole genome profiles of typical BRCA1 null (e.g. PD6413a, PD7215a) and BRCA2 null tumours (e.g. PD4952a, PD4955a)).

A further subset of cancers (Cluster F, FIG. 8) show similarities in mutational pattern to BRCA1/2 null cancers, with many Rearrangement Signature 5 deletions and enrichment for base substitution signatures 3 and 8. However, these do not segregate together with BRCA1/2 null cases in hierarchical clustering analysis, have Rearrangement Signature 1 large tandem duplications and do not show BRCA1/2 mutations. Somatic and germline mutations in genes associated with the DNA double-strand break repair pathway including ATM, ATR, PALB2, RAD51C, RAD50, TP53, CHEK2 and BRIP1, were sought in these cancers. We did not observe any clear-cut relationships between mutations in these genes and these mutational patterns.

Cancers with BRCA1/2 mutations are particularly responsive to cisplatin and PARP inhibitors [43-45]. Combinations of base substitution, indel and rearrangement mutational signatures may be better biomarkers of defective homologous recombination based DNA double strand break repair and responsiveness to these drugs [46] than BRCA1/2 mutations or promoter methylation alone and thus may constitute the basis of future diagnostics.

As a development of these observations, a method for determining the likelihood of a tumour being HR deficient was developed, as set out in more detail in PCT/EP2017/060294, the contents of which are hereby incorporated by reference. In embodiments of the present invention, the "BRCAness predictor" methods of that application can form an additional part of the characterisation of the tumour.

Methods

Sample Selection

DNA was extracted from 560 breast cancers and normal tissue (peripheral blood lymphocytes, adjacent normal breast tissue or skin) from the same individuals. Samples were subjected to pathology review and only samples assessed as being composed of >70% tumor cells, were accepted for inclusion in the study.

Massively-Parallel Sequencing and Alignment

Short insert 500 bp genomic libraries were constructed, flowcells prepared and sequencing clusters generated according to Illumina library protocols [47]. 108 base/100 base (genomic), or 75 base (transcriptomic) paired-end sequencing were performed on Illumina GAIIx, Hiseq 2000 or Hiseq 2500 genome analyzers in accordance with the Illumina Genome Analyzer operating manual. The average sequence coverage was 40.4 fold for tumour samples and 30.2 fold for normal samples.

Short insert paired-end reads were aligned to the reference human genome (GRCh37) using Burrows-Wheeler Aligner, BWA (v0.5.9) [48].

Processing of Genomic Data

CaVEMan (Cancer Variants Through Expectation Maximization: cancerit.github.io/CaVEMan/) was used for calling somatic substitutions.

Indels in the tumor and normal genomes were called using a modified Pindel version 2.0. (cancerit.github.io/cgpPindel/) on the NCBI37 genome build [49].

Structural variants were discovered using a bespoke algorithm, BRASS (BReakpoint AnalySiS) (github.com/cancerit/BRASS) through discordantly mapping paired-end reads. Next, discordantly mapping read pairs that were likely to span breakpoints, as well as a selection of nearby properly-paired reads, were grouped for each region of interest. Using the Velvet de novo assembler [50], reads were locally assembled within each of these regions to produce a contiguous consensus sequence of each region. Rearrangements, represented by reads from the rearranged derivative as well as the corresponding non-rearranged allele were instantly recognisable from a particular pattern of five vertices in the de Bruijn graph (a mathematical method used in de novo assembly of (short) read sequences) of component of Velvet. Exact coordinates and features of junction sequence (e.g. microhomology or non-templated sequence) were derived from this, following aligning to the reference genome, as though they were split reads.

Single nucleotide polymorphism (SNP) array hybridization using the Affymetrix SNP6.0 platform was performed according to Affymetrix protocols. Allele-specific copy number analysis of tumors was performed using ASCAT (v2.1.1), to generate integral allele-specific copy number profiles for the tumor cells [51]. ASCAT was also applied to NGS data directly with highly comparable results.

Identification of Novel Breast Cancer Genes

To identify recurrently mutated driver genes, a dN/dS method that considers the mutation spectrum, the sequence of each gene, the impact of coding substitutions (synonymous, missense, nonsense, splice site) and the variation of the mutation rate across genes [52, 53] was used for substitutions. Owing to the lack of a neutral reference for the indel rate in coding sequences, a different approach was required. To detect genes under significant selective pressure by either point mutations or indels, for each gene the P-values from the dN/dS analysis of substitutions and from the recurrence analysis of indels were combined using Fisher's method. Multiple testing correction (Benjamini-Hochberg FDR) was performed separately for the 600+ putative driver genes and for all other genes, stratifying the FDR correction to increase sensitivity (as described in Sun et al. 2006 [54]). To achieve a low false discovery rate a conservative q-value cutoff of <0.01 was used for significance.

This analysis was applied to the 560 whole genome sequenced breast cancers as well as a further 772 breast cancers that have been sequenced previously by other institutions.

Recurrence in the Non-Coding Regions

Partitioning the Genome into Functional Regulatory Elements/Gene Features

To identify non-coding regions with significant recurrence, the inventors used a method similar to the one described for searching for novel indel drivers.

The genome was partitioned according to different sets of regulatory elements/gene features, with a separate analysis performed for each set of elements, including exons (n=20, 245 genes), core promoters (n=20,245 genes, where a core promoter is the interval [−250,+250] bp from any transcription start site (TSS) of a coding transcript of the gene, excluding any overlap with coding regions), 5' UTR (n=9, 576 genes), 3' UTR (n=19,502 genes), intronic regions flanking exons (n=20,212 genes, represents any intronic sequence within 75 bp from an exon, excluding any base overlapping with any of the above elements. This attempts to capture recurrence in essential splice site or proximal splicing-regulatory elements), any other sequence within genes (n=18,591 genes, for every protein-coding gene, this contains any region within the start and end of transcripts not included in any of the above categories), ncRNAs (n=10, 684, full length lincRNAs, miRNAs or rRNAs), enhancers (n=194,054) [55], ultra-conserved regions (n=187,057, a collection of regions under negative selection based on 1,000 genomes data [20].

Every element set listed above was analysed separately to allow for different mutation rates across element types and to stratify the FDR correction [54]. Within each set of elements, a negative binomial regression approach was used to learn the underlying variation of the mutation rate across elements. The offset reflects the expected number of mutations in each element assuming uniform mutation rates across them (i.e. $E_{subs,element} = \Sigma_{j \in \{1,2,\ldots,192\}} (t^* r_j^* S_j)$, and, $E_{indels,element} = \mu_{indel}^* S_{indel,element}$). As covariate here the local density of mutations in neighbouring non-coding regions was used, corrected for sequence composition and trinucleotide mutation rates, that is, the t parameter of the dN/dS equations. Normalised local rates were pre-calculated for 100 kb non-overlapping bins of the genome and used in all analyses. Other covariates (expression, replication time or HiC) were not used here as they were not found to substantially improve the model once the local mutation rate was used as a covariate. A separate regression analysis was performed for substitutions and indels, to account for the different level of uncertainty in the distribution of substitution and indel rates across elements.

$$model_{subs} = glm.nb(formula = n_{subs} \sim offset(\log(E_{subs})) + \mu_{local,subs})$$

$$model_{indels} = glm.nb(formula = n_{indels} \sim offset(\log(E_{indels})) + \mu_{local,indels})$$

The observed counts for each element ($n_{subs,element}$ and $n_{indels,element}$) are compared to the background distributions using a negative binomial test, with the estimated overdispersion parameters ($\theta_{subs}$ and $\theta_{indels}$) estimated by the negative binomial regression, yielding P-values for substitution and indel recurrence for each element. These P-values were combined using Fisher's method and corrected for multiple testing using FDR.

Partitioning the Genome into Discrete Bins

Figure 9A:
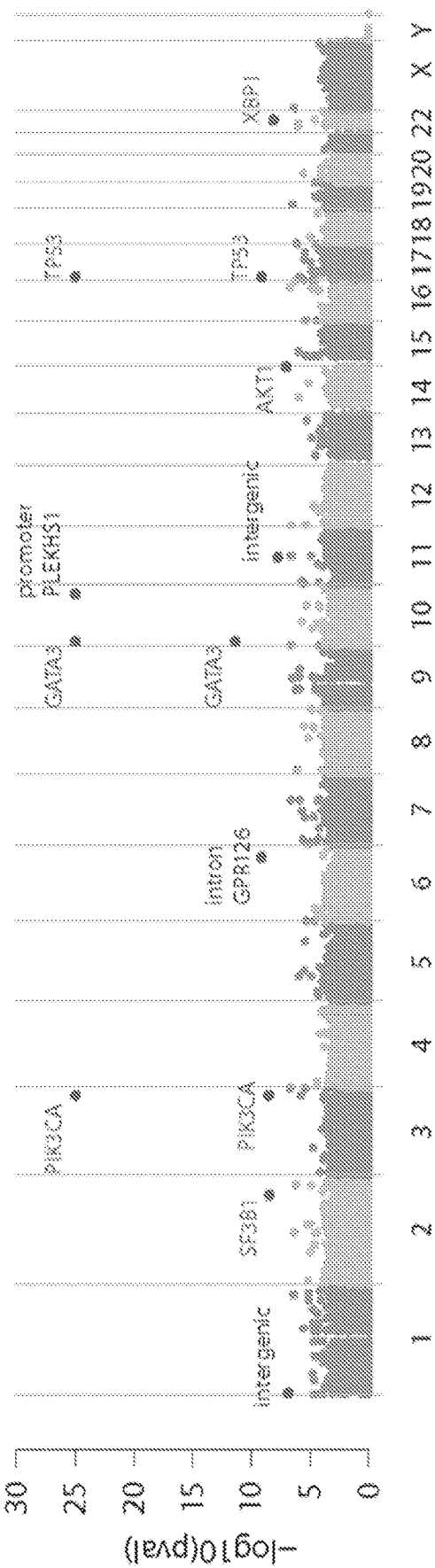
FIGS. 9A-9D show recurrent non-coding events in breast cancers.
Figure 9B:
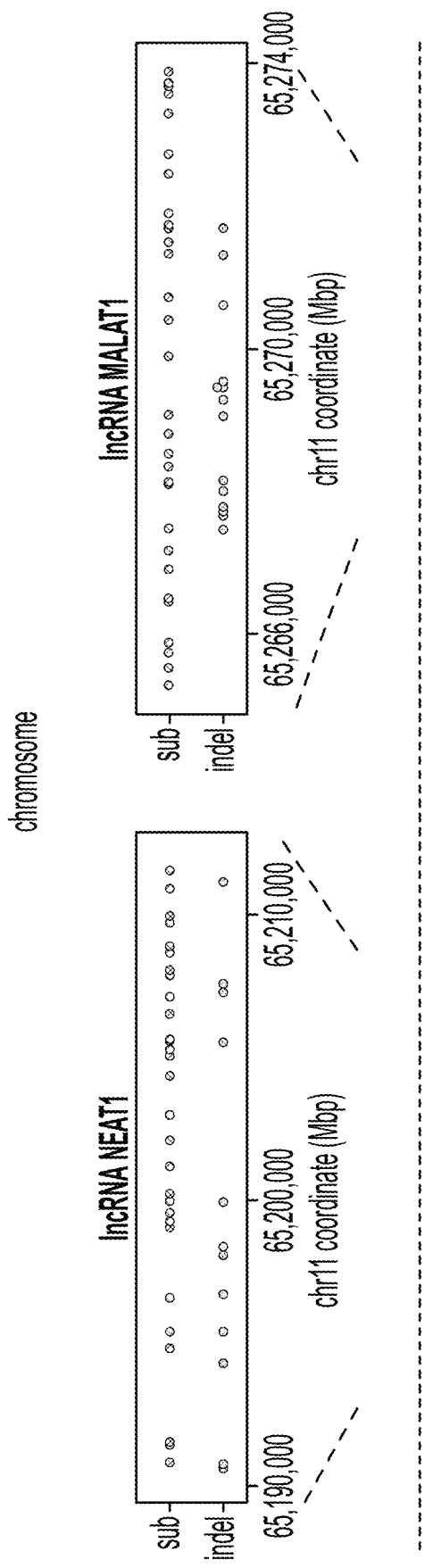
Figure 9C:
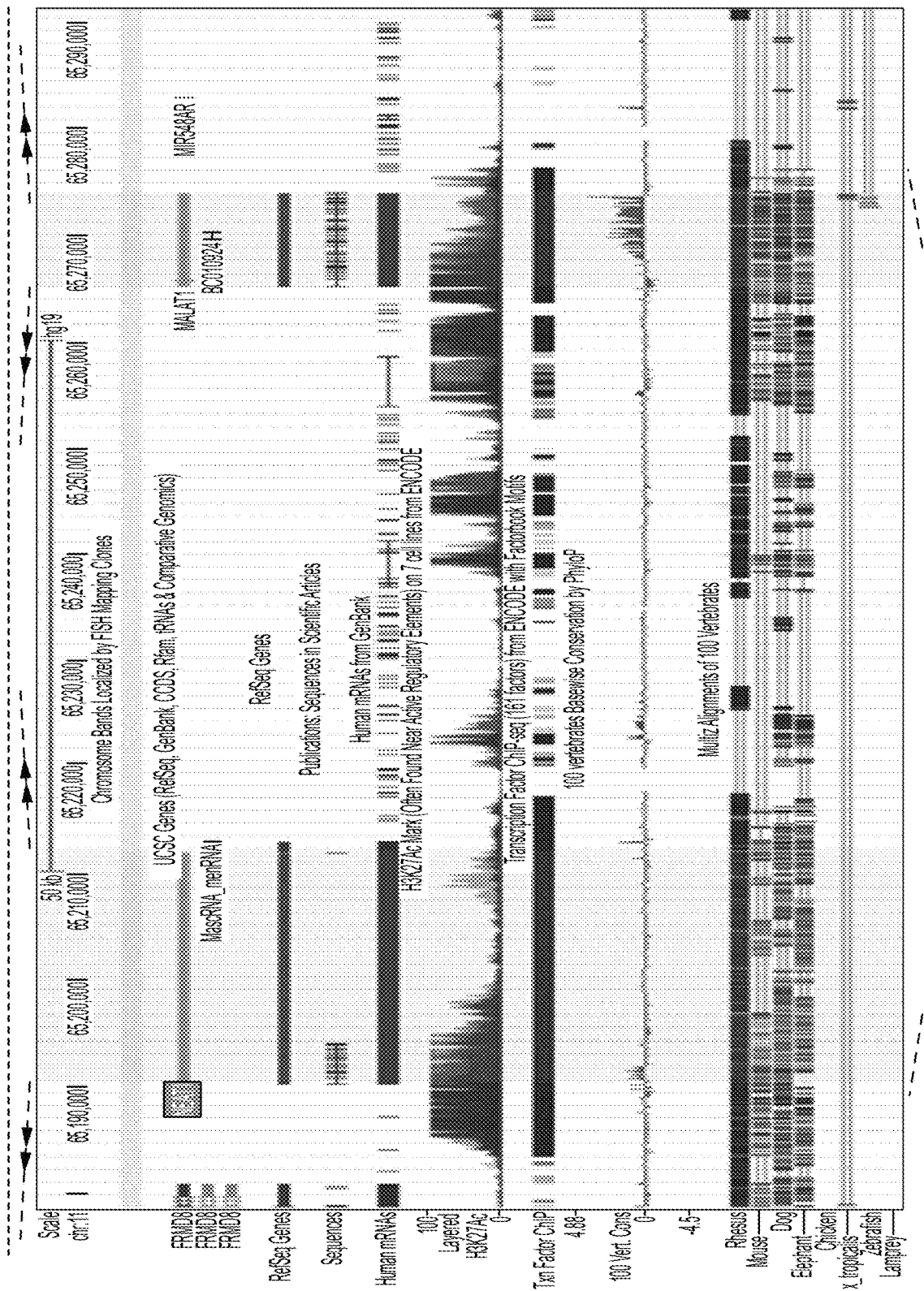
Figure 9D:
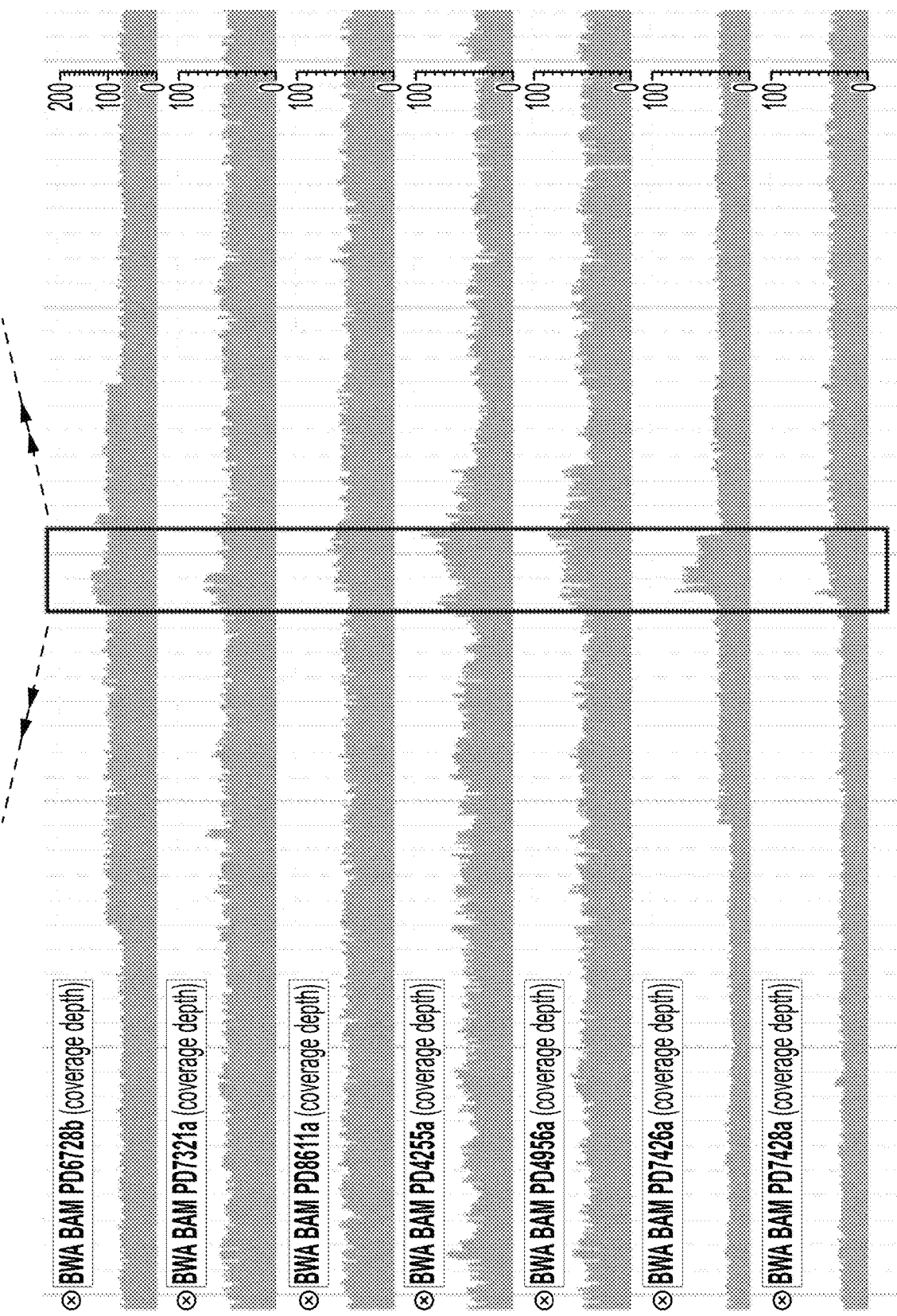

A genome-wide screening of recurrence in 1 kb non-overlapping bins was performed. The method described in the earlier section was employed, using as covariate the local mutation rate calculated from 5 Mb up and downstream from the bin of interest and excluding any low-coverage region from the estimate (FIG. 9A for example). Significant hits were subjected to manual curation to remove false positives caused by sequencing or mapping artefacts.

Mutational Signatures Analysis

Mutational signatures analysis was performed following a three-step process: (i) hierarchical de novo extraction based on somatic substitutions and their immediate sequence context, (ii) updating the set of consensus signatures using the mutational signatures extracted from breast cancer genomes, and (iii) evaluating the contributions of each of the updated consensus signatures in each of the breast cancer samples. These three steps are discussed in more detail in the next sections.

Hierarchical De Novo Extraction of Mutational Signatures

The mutational catalogues of the 560 breast cancer whole genomes were analysed for mutational signatures using a hierarchical version of the Wellcome Trust Sanger Institute mutational signatures framework [25]. Briefly, we converted all mutation data into a matrix, M, that is made up of 96 features comprising mutations counts for each mutation type (C>A, C>G, C>T, T>A, T>C, and T>G; all substitutions are referred to by the pyrimidine of the mutated Watson-Crick base pair) using each possible 5' (C, A, G, and T) and 3' (C, A, G, and T) context for all samples. After conversion, the previously developed algorithm was applied in a hierarchical manner to the matrix M that contains K mutation types and G samples. The algorithm deciphers the minimal set of mutational signatures that optimally explains the proportion of each mutation type and then estimates the contribution of each signature across the samples. More specifically, the algorithm makes use of a well-known blind source separation technique, termed nonnegative matrix factorization (NMF). NMF identifies the matrix of mutational signature, P, and the matrix of the exposures of these signatures, E, by minimizing a Frobenius norm while maintaining non-negativity:

$$\min_{P \in \mathfrak{M}_{\mathbb{R}_+}^{(K,N)} E \in \mathfrak{M}_{\mathbb{R}_+}^{(N,G)}} \|M - P \times E\|_F^2$$

Figure 5C:
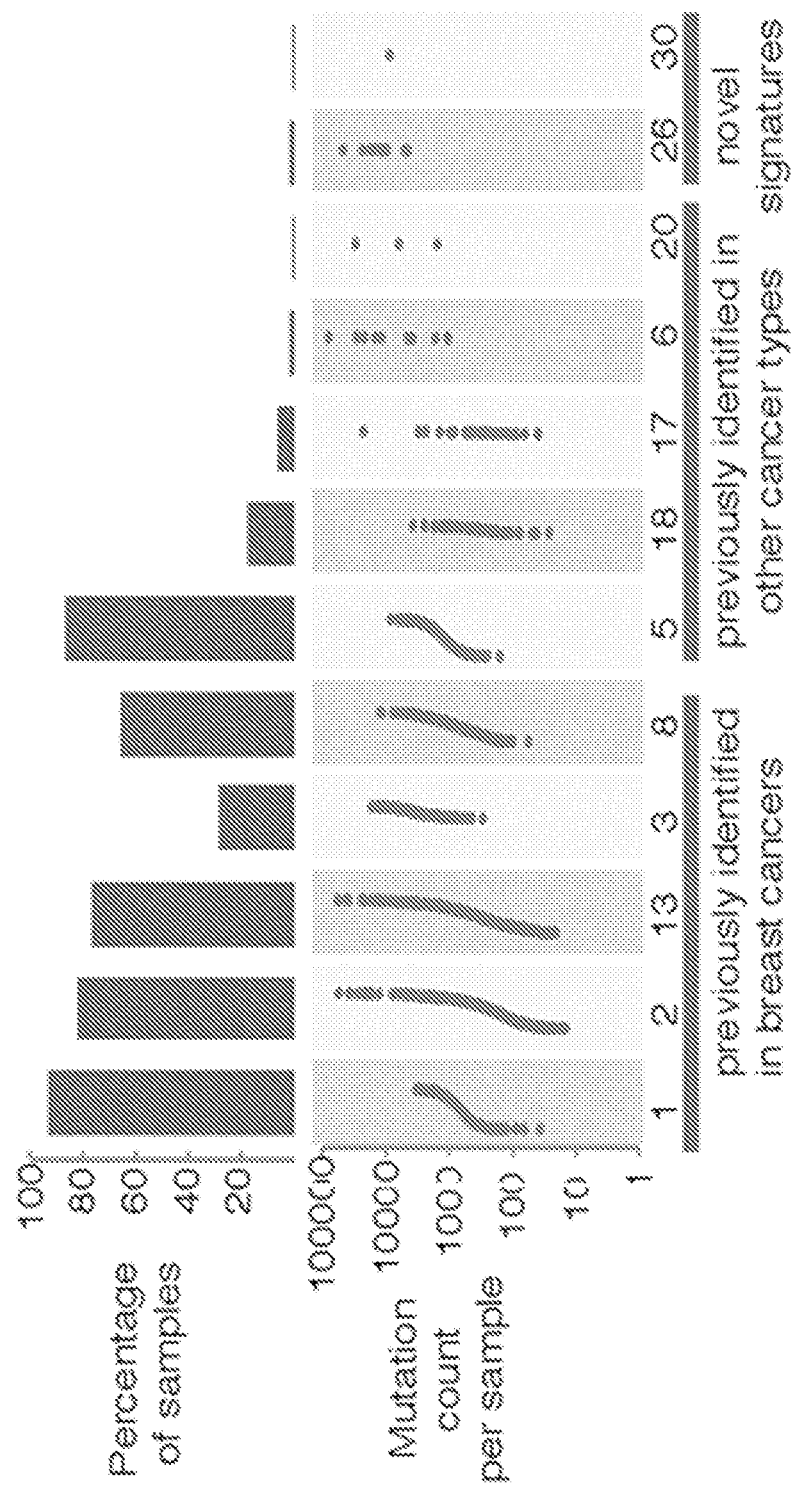

The method for deciphering mutational signatures, including evaluation with simulated data and list of limitations, can be found in [25]. The framework was applied in a hierarchical manner to increase its ability to find mutational signatures present in few samples as well as mutational signatures exhibiting a low mutational burden. More specifically, after application to the original matrix M containing 560 samples, we evaluated the accuracy of explaining the mutational patterns of each of the 560 breast cancers with the extracted mutational signatures. All samples that were well explained by the extracted mutational signatures were removed and the framework was applied to the remaining sub-matrix of M. This procedure was repeated until the extraction process did not reveal any new mutational signatures. Overall, the approach extracted 12 unique mutational signatures operative across the 560 breast cancers (FIG. 5).

Updating the Set of Consensus Mutational Signatures

The 12 hierarchically extracted breast cancer signatures were compared to the census of consensus mutational signatures [25]. 11 of the 12 signatures closely resembled previously identified mutational patterns. The patterns of these 11 signatures, weighted by the numbers of mutations contributed by each signature in the breast cancer data, were used to update the set of consensus mutational signatures as previously done in [25]. 1 of the 12 extracted signatures is novel and at present, unique for breast cancer. This novel signature is consensus signature 30 (cancer.sanger.ac.uk/cosmic/signatures).

Evaluating the Contributions of Consensus Mutational Signatures in 560 Breast Cancers The complete compendium of consensus mutational signatures that was found in breast cancer includes: signatures 1, 2, 3, 5, 6, 8, 13, 17, 18, 20, 26, and 30. We evaluated the presence of all these signatures in the 560 breast cancer genomes by re-introducing them into each sample. More specifically, the updated set of consensus mutational signatures was used to minimize the constrained linear function for each sample:

$$\min_{Exposures_i \geq 0} \left\| SampleMutations - \sum_{i=1}^{N} (\overrightarrow{Signature_i} * Exposure_i) \right\|_F^2$$

Here, $\overrightarrow{Signature_i}$ represents a vector with 96 components (corresponding to a consensus mutational signature with its six somatic substitutions and their immediate sequencing context) and Exposure, is a nonnegative scalar reflecting the number of mutations contributed by this signature. N is equal to 12 and it reflects the number of all possible signatures that can be found in a single breast cancer sample. Mutational signatures that did not contribute large numbers (or proportions) of mutations or that did not significantly improve the correlation between the original mutational pattern of the sample and the one generated by the mutational signatures were excluded from the sample. This procedure reduced over-fitting the data and allowed only the essential mutational signatures to be present in each sample (Supplementary Table 21B).

Kataegis

Kataegis or foci of localized hypermutation has been previously defined [25] as 6 or more consecutive mutations with an average intermutation distance of less than or equal to 1,000 bp. Kataegis were sought in 560 whole-genome sequenced breast cancers from high-quality base substitution data using the method described previously [25]. This method likely misses some foci of kataegis sacrificing sensitivity of detection for a higher positive predictive value of kataegic foci.

Rearrangement Signatures

Clustered Vs Non-Clustered Rearrangements

Rearrangements that occurred as focal catastrophic events or focal driver amplicons were separated from genome-wide rearrangement mutagenesis using a piecewise constant fitting (PCF) method. For each sample, both breakpoints of each rearrangement were considered individually and all breakpoints were ordered by chromosomal position. The inter-rearrangement distance, defined as the number of base pairs from one rearrangement breakpoint to the one immediately preceding it in the reference genome, was calculated. Putative regions of clustered rearrangements were identified as having an average inter-rearrangement distance that was at least 10 times greater than the whole genome average for the individual sample. PCF parameters used were $\gamma=25$ and kmin=10. The respective partner breakpoint of all breakpoints involved in a clustered region are likely to have arisen at the same mechanistic instant and so were considered as being involved in the cluster even if located at a distant chromosomal site. Extended Data Table 4A summarises the rearrangements within clusters ("clustered") and not within clusters ("non-clustered").

Classification—Types and Size

In both classes of rearrangements, clustered and non-clustered, rearrangements were subclassified into deletions, inversions and tandem duplications, and then further subclassified according to size of the rearranged segment (1-10 kb, 10 kb-100 kb, 100 kb-1 Mb, 1 Mb-10 Mb, more than 10 Mb). The final category in both groups was interchromosomal translocations.

Rearrangement Signatures by NNMF

The classification produces a matrix of 32 distinct categories of structural variants across 544 breast cancer genomes. This matrix was decomposed using the previously developed approach for deciphering mutational signatures by searching for the optimal number of mutational signatures that best explains the data without over-fitting the data [25].

Consensus Clustering of Rearrangement Signatures

To identify subgroups of samples sharing similar combinations of six identified rearrangement signatures derived from whole genome sequencing analysis consensus clustering was performed using the ConsensusClusterPlus R package [56]. Input data for each sample (n=544, a subset of the full sample cohort) was the proportion of rearrangements assigned to each of the six signatures. Thus, each sample has 6 data values, with a total sum of 1. Proportions for each signature were mean-centred across samples prior to clustering. The following settings were used in the consensus clustering:

Number of repetitions: 1000
pItem=0.9 (resampling frequency samples)
pFeature=0.9 (resampling frequency)
Pearson distance metric
Ward linkage method Individual Patient Whole Genome Profiles Breast cancer whole genome profiles were adapted from the R Circos package [57]. Features depicted in circos plots from outermost rings heading inwards: Karyotypic ideogram outermost. Base substitutions next, plotted as rainfall plots (log 10 intermutation distance on radial axis, dot colours: blue=C>A, black=C>G, red=C>T, grey=T>A, green=T>C, pink=T>G). Ring with short green lines=insertions, ring with short red lines=deletions. Major copy number allele (green=gain) ring, minor copy number allele ring (pink=loss), Central lines represent rearrangements (green=tandem duplications, pink=deletions, blue=inversions and gray=interchromosomal events. Top right hand panel displays the number of mtations contributing to each mutation signature extracted using NNMF in individual cancers. Middle right hand panel represents indels. Bottom right corner shows histogram of rearrangements present in this cancer. Bottom left corner shows all curated driver mutations, top and middle left panels show clinical and pathology data respectively.

The systems and methods of the above embodiments may be implemented in a computer system (in particular in computer hardware or in computer software) in addition to the structural components and user interactions described.

The term "computer system" includes the hardware, software and data storage devices for embodying a system or carrying out a method according to the above described embodiments. For example, a computer system may comprise a central processing unit (CPU), input means, output means and data storage. Preferably the computer system has a monitor to provide a visual output display (for example in the design of the business process). The data storage may comprise RAM, disk drives or other computer readable media. The computer system may include a plurality of computing devices connected by a network and able to communicate with each other over that network.

The methods of the above embodiments may be provided as computer programs or as computer program products or computer readable media carrying a computer program which is arranged, when run on a computer, to perform the method(s) described above.

The term "computer readable media" includes, without limitation, any non-transitory medium or media which can be read and accessed directly by a computer or computer system. The media can include, but are not limited to, magnetic storage media such as floppy discs, hard disc storage media and magnetic tape; optical storage media such as optical discs or CD-ROMs; electrical storage media such as memory, including RAM, ROM and flash memory; and hybrids and combinations of the above such as magnetic/optical storage media.

---

Lengthy table referenced here

US12062416-20240813-T00001

Please refer to the end of the specification for access instructions.

Lengthy table referenced here

US12062416-20240813-T00002

Please refer to the end of the specification for access instructions.

Lengthy table referenced here

US12062416-20240813-T00003

Please refer to the end of the specification for access instructions.

Lengthy table referenced here

US12062416-20240813-T00004

Please refer to the end of the specification for access instructions.

Lengthy table referenced here

US12062416-20240813-T00005

Please refer to the end of the specification for access instructions.

Lengthy table referenced here

US12062416-20240813-T00006

Please refer to the end of the specification for access instructions.

Lengthy table referenced here

US12062416-20240813-T00007

Please refer to the end of the specification for access instructions.

Lengthy table referenced here

US12062416-20240813-T00008

Please refer to the end of the specification for access instructions.

Lengthy table referenced here

US12062416-20240813-T00009

Please refer to the end of the specification for access instructions.

Lengthy table referenced here

US12062416-20240813-T00010

Please refer to the end of the specification for access instructions.

Lengthy table referenced here

US12062416-20240813-T00011

Please refer to the end of the specification for access instructions.

Lengthy table referenced here

US12062416-20240813-T00012

Please refer to the end of the specification for access instructions.

Lengthy table referenced here

US12062416-20240813-T00013

Please refer to the end of the specification for access instructions.

Lengthy table referenced here

US12062416-20240813-T00014

Please refer to the end of the specification for access instructions.

Lengthy table referenced here

US12062416-20240813-T00015

Please refer to the end of the specification for access instructions.

Lengthy table referenced here

US12062416-20240813-T00016

Please refer to the end of the specification for access instructions.

Lengthy table referenced here

US12062416-20240813-T00017

Please refer to the end of the specification for access instructions.

REFERENCES

1 Stratton, M. R., Campbell, P. J. & Futreal, P. A. The cancer genome. *Nature* 458, 719-724, doi:10.1038/nature07943 (2009).
2 Nik-Zainal, S. et al. Mutational processes molding the genomes of 21 breast cancers. *Cell* 149, 979-993, doi: 10.1016/j.cell.2012.04.024 (2012).
3 Nik-Zainal, S. et al. The life history of 21 breast cancers. *Cell* 149, 994-1007, doi:10.1016/j.cell.2012.04.023 (2012).
4 Hicks, J. et al. Novel patterns of genome rearrangement and their association with survival in breast cancer. *Genome research* 16, 1465-1479, doi:10.1101/gr.5460106 (2006).

5 Bergamaschi, A. et al. Extracellular matrix signature identifies breast cancer subgroups with different clinical outcome. *The Journal of pathology* 214, 357-367, doi: 10.1002/path.2278 (2008).

6 Ching, H. C., Naidu, R., Seong, M. K., Har, Y. C. & Taib, N. A. Integrated analysis of copy number and loss of heterozygosity in primary breast carcinomas using high-density SNP array. *International journal of oncology* 39, 621-633, doi:10.3892/ijo.2011.1081 (2011).

7 Fang, M. et al. Genomic differences between estrogen receptor (ER)-positive and ER-negative human breast carcinoma identified by single nucleotide polymorphism array comparative genome hybridization analysis. *Cancer* 117, 2024-2034, doi:10.1002/cncr.25770 (2011).

8 Curtis, C. et al. The genomic and transcriptomic architecture of 2,000 breast tumours reveals novel subgroups. *Nature* 486, 346-352, doi:10.1038/nature10983 (2012).

9 Pleasance, E. D. et al. A comprehensive catalogue of somatic mutations from a human cancer genome. *Nature* 463, 191-196, doi:10.1038/nature08658 (2010).

Pleasance, E. D. et al. A small-cell lung cancer genome with complex signatures of tobacco exposure. *Nature* 463, 184-190, doi:10.1038/nature08629 (2010).

11 Banerji, S. et al. Sequence analysis of mutations and translocations across breast cancer subtypes. *Nature* 486, 405-409, doi:10.1038/nature11154 (2012).

12 Ellis, M. J. et al. Whole-genome analysis informs breast cancer response to aromatase inhibition. *Nature* 486, 353-360, doi:10.1038/nature11143 (2012).

13 Shah, S. P. et al. The clonal and mutational evolution spectrum of primary triple-negative breast cancers. *Nature* 486, 395-399, doi:10.1038/nature10933 (2012).

14 Stephens, P. J. et al. The landscape of cancer genes and mutational processes in breast cancer. *Nature* 486, 400-404, doi:10.1038/nature11017 (2012).

15 Cancer Genome Atlas, N. Comprehensive molecular portraits of human breast tumours. *Nature* 490, 61-70, doi:10.1038/nature11412 (2012).

16 Wu, Y. M. et al. Identification of targetable FGFR gene fusions in diverse cancers. *Cancer discovery* 3, 636-647, doi:10.1158/2159-8290.CD-13-0050 (2013).

17 Giacomini, C. P. et al. Breakpoint analysis of transcriptional and genomic profiles uncovers novel gene fusions spanning multiple human cancer types. *PLoS genetics* 9, e1003464, doi:10.1371/journal.pgen.1003464 (2013).

18 Robinson, D. R. et al. Functionally recurrent rearrangements of the MAST kinase and Notch gene families in breast cancer. *Nature medicine* 17, 1646-1651, doi: 10.1038/nm.2580 (2011).

19 Karlsson, J. et al. Activation of human telomerase reverse transcriptase through gene fusion in clear cell sarcoma of the kidney. *Cancer letters* 357, 498-501, doi:10.1016/j.canlet.2014.11.057 (2015).

20 Khurana, E. et al. Integrative annotation of variants from 1092 humans: application to cancer genomics. *Science* 342, 1235587, doi:10.1126/science.1235587 (2013).

21 West, J. A. et al. The long noncoding RNAs NEAT1 and MALAT1 bind active chromatin sites. *Molecular cell* 55, 791-802, doi:10.1016/j.molcel.2014.07.012 (2014).

22 Huang, F. W. et al. Highly recurrent TERT promoter mutations in human melanoma. *Science* 339, 957-959, doi:10.1126/science.1229259 (2013).

23 Vinagre, J. et al. Frequency of TERT promoter mutations in human cancers. *Nature communications* 4, 2185, doi: 10.1038/ncomms3185 (2013).

24 Alexandrov, L. B. et al. Signatures of mutational processes in human cancer. *Nature* 500, 415-421, doi: 10.1038/nature12477 (2013).

25 Alexandrov, L. B., Nik-Zainal, S., Wedge, D. C., Campbell, P. J. & Stratton, M. R. Deciphering signatures of mutational processes operative in human cancer. *Cell reports* 3, 246-259, doi:10.1016/j.celrep.2012.12.008 (2013).

26 Lawrence, M. S. et al. Discovery and saturation analysis of cancer genes across 21 tumour types. *Nature* 505, 495-501, doi:10.1038/nature12912 (2014).

27 Natrajan, R. et al. Characterization of the genomic features and expressed fusion genes in micropapillary carcinomas of the breast. *The Journal of pathology* 232, 553-565, doi:10.1002/path.4325 (2014).

28 Kalyana-Sundaram, S. et al. Gene fusions associated with recurrent amplicons represent a class of passenger aberrations in breast cancer. *Neoplasia* 14, 702-708 (2012).

29 Tubio, J. M. Somatic structural variation and cancer. *Briefings in functional genomics*, doi:10.1093/bfgp/elv016 (2015).

30 Weinhold, N., Jacobsen, A., Schultz, N., Sander, C. & Lee, W. Genome-wide analysis of noncoding regulatory mutations in cancer. *Nature genetics* 46, 1160-1165, doi: 10.1038/ng.3101 (2014).

31 Ussery, D. W., Binnewies, T. T., Gouveia-Oliveira, R., Jarmer, H. & Hallin, P. F. Genome update: DNA repeats in bacterial genomes. *Microbiol-Sgm* 150, 3519-3521, doi:Doi 10.1099/Mic.0.27628-0 (2004).

32 Lu, S. et al. Short Inverted Repeats Are Hotspots for Genetic Instability: Relevance to Cancer Genomes. *Cell reports*, doi:10.1016/j.celrep.2015.02.039 (2015).

33 Voineagu, I., Narayanan, V., Lobachev, K. S. & Mirkin, S. M. Replication stalling at unstable inverted repeats: interplay between DNA hairpins and fork stabilizing proteins. *Proceedings of the National Academy of Sciences of the United States of America* 105, 9936-9941, doi:10.1073/pnas.0804510105 (2008).

34 Wojcik, E. A. et al. Direct and inverted repeats elicit genetic instability by both exploiting and eluding DNA double-strand break repair systems in mycobacteria. *PloS one* 7, e51064, doi:10.1371/journal.pone.0051064 (2012).

35 Pearson, C. E., Zorbas, H., Price, G. B. & Zannis-Hadjopoulos, M. Inverted repeats, stem-loops, and cruciforms: significance for initiation of DNA replication. *Journal of cellular biochemistry* 63, 1-22, doi:10.1002/(SICI)1097-4644(199610)63:1<1::AID-JCB1 > 3.0.CO;2-3 (1996).

36 Kozak, M. Interpreting cDNA sequences: some insights from studies on translation. *Mammalian genome: official journal of the International Mammalian Genome Society* 7, 563-574 (1996).

37 Helleday, T., Eshtad, S. & Nik-Zainal, S. Mechanisms underlying mutational signatures in human cancers. *Nature reviews. Genetics* 15, 585-598, doi:10.1038/nrg3729 (2014).

38 Birkbak, N. J. et al. Telomeric allelic imbalance indicates defective DNA repair and sensitivity to DNA-damaging agents. *Cancer discovery* 2, 366-375, doi:10.1158/2159-8290.CD-11-0206 (2012).

39 Abkevich, V. et al. Patterns of genomic loss of heterozygosity predict homologous recombination repair defects in epithelial ovarian cancer. *British journal of cancer* 107, 1776-1782, doi:10.1038/bjc.2012.451 (2012).

40 Popova, T. et al. Ploidy and large-scale genomic instability consistently identify basal-like breast carcinomas with BRCA1/2 inactivation. *Cancer research* 72, 5454-5462, doi:10.1158/0008-5472.CAN-12-1470 (2012).
41 Puente, X. S. et al. Whole-genome sequencing identifies recurrent mutations in chronic lymphocytic leukaemia. *Nature* 475, 101-105, doi:10.1038/nature10113 (2011).
42 Morganella, S. A., L. B.; The topography of mutational processes in breast cancer. Submitted (2015).
43 Fong, P. C. et al. Inhibition of poly(ADP-ribose) polymerase in tumors from BRCA mutation carriers. *The New England journal of medicine* 361, 123-134, doi:10.1056/NEJMoa0900212 (2009).
44 Forster, M. D. et al. Treatment with olaparib in a patient with PTEN-deficient endometrioid endometrial cancer. *Nature reviews. Clinical oncology* 8, 302-306, doi: 10.1038/nrclinonc.2011.42 (2011).
45 Turner, N., Tutt, A. & Ashworth, A. Targeting the DNA repair defect of BRCA tumours. *Current opinion in pharmacology* 5, 388-393, doi:10.1016/j.coph.2005.03.006 (2005).
46 Waddell, N. et al. Whole genomes redefine the mutational landscape of pancreatic cancer. *Nature* 518, 495-501, doi:10.1038/nature14169 (2015).
47 Kozarewa, I. et al. Amplification-free Illumina sequencing-library preparation facilitates improved mapping and assembly of (G+C)-biased genomes. Nature methods 6, 291-295, doi:10.1038/nmeth.1311 (2009).
48 Li, H. & Durbin, R. Fast and accurate short read alignment with Burrows-Wheeler transform. Bioinformatics 25, 1754-1760, doi:10.1093/bioinformatics/btp324 (2009).
49 Ye, K., Schulz, M. H., Long, Q., Apweiler, R. & Ning, Z. Pindel: a pattern growth approach to detect break points of large deletions and medium sized insertions from paired-end short reads. Bioinformatics 25, 2865-2871, doi:10.1093/bioinformatics/btp394 (2009).
50 Zerbino, D. R. & Birney, E. Velvet: algorithms for de novo short read assembly using de Bruijn graphs. Genome research 18, 821-829, doi:10.1101/gr.074492.107 (2008).
51 Van Loo, P. et al. Allele-specific copy number analysis of tumors. Proceedings of the National Academy of Sciences of the United States of America 107, 16910-16915, doi: 10.1073/pnas.1009843107 (2010).
52 Greenman, C., Wooster, R., Futreal, P. A., Stratton, M. R. & Easton, D. F. Statistical analysis of pathogenicity of somatic mutations in cancer. Genetics 173, 2187-2198, doi:10.1534/genetics.105.044677 (2006).
53 Lawrence, M. S. et al. Mutational heterogeneity in cancer and the search for new cancer-associated genes. Nature 499, 214-218, doi:10.1038/nature12213 (2013).
54 Sun, L., Craiu, R. V., Paterson, A. D. & Bull, S. B. Stratified false discovery control for large-scale hypothesis testing with application to genome-wide association studies. Genetic epidemiology 30, 519-530, doi:10.1002/gepi.20164 (2006).
55 Consortium, E. P. An integrated encyclopedia of DNA elements in the human genome. Nature 489, 57-74, doi: 10.1038/nature11247 (2012).
56 Wilkerson, M. D. & Hayes, D. N. ConsensusClusterPlus: a class discovery tool with confidence assessments and item tracking. Bioinformatics 26, 1572-1573, doi:btq170 [pii]10.1093/bioinformatics/btq170 (2010).
57 Zhang, H., Meltzer, P. & Davis, S. R Circos: an R package for Circos 2D track plots. BMC bioinformatics 14, 244, doi:10.1186/1471-2105-14-244 (2013).
58. Alexandrov, L. B. et al. A mutational signature in gastric cancer suggests therapeutic strategies. Nat. Commun. 6:8683 doi: 10.1038/ncomms9683 (2015).
59. Raine, K. M., Hinton, J., Butler, A. P., Teague, J. W., Davies, H., Tarpey, P., Nik-Zainal, S. and Campbell, P. J. 2015. cgpPindel: Identifying somatically acquired insertion and deletion events from paired end sequencing. *Curr. Protoc. Bioinform.* 52:15.7.1-15.7.12. doi: 10.1002/0471250953.bi1507s52.
60. Ye, K., Schulz, M. H., Long, Q., Apweiler, R., and Ning, Z. 2009. Pindel: A pattern growth approach to detect break points of large deletions and medium sized insertions from pairedend short reads. *Bioinformatics* (Oxford, England) 25:2865-2871. doi: 10.1093/bioinformatics/btp394.

---

LENGTHY TABLES

The patent contains a lengthy table section. A copy of the table is available in electronic form from the USPTO web site (https://seqdata.uspto.gov/?pageRequest=docDetail&DocID=US12062416B2). An electronic copy of the table will also be available from the USPTO upon request and payment of the fee set forth in 37 CFR 1.19(b)(3).

---

The invention claimed is:

1. A method of treating a patient having breast cancer by constructing an interpreted profile of a DNA sample obtained from a breast cancer tumour of the patient and using the interpreted profile to determine whether to administer cisplatin and/or a PARP inhibitor to the patient as a cancer therapy, the method comprising:
   a) determining, by a processor, from whole-genome sequencing data from said DNA sample a catalogue of one or more rearrangement signatures which are present in the DNA sample by:
      (i) classifying each rearrangement in the DNA sample in one of a plurality of categories, the one of the plurality of categories selected from the group consisting of a category of two or more categories of clustered deletions that differ by their size, a category of two or more categories of non-clustered deletions that differ by their size, a category of two or more categories of clustered inversions that differ by their size, a category of two or more categories of non-clustered inversions that differ by their size, a category of clustered translocations, a category of non-clustered translocations, a category of two or more categories of clustered tandem duplications that differ by their size, and a category of two or more categories of non-clustered tandem duplications that differ by their size, thereby obtaining a rearrangement catalogue for said DNA sample, wherein the rearrangement catalogue comprises a number of rearrangements in said DNA sample classified in each of said plurality of categories; and (ii) identifying one or more rearrangement signatures present in the DNA sample, wherein the one or more rearrangement signatures comprise defined patterns of rearrangements as classified between the plurality of categories, and wherein the number of the rearrangements in said rearrangement catalogue for said DNA sample that is attributable to each of the one or more rearrangement signatures that is present in said DNA sample is determined to be above a predetermined threshold;

b) determining, by said processor, from the whole-genome sequencing data from said DNA sample two or more items among:
  (i) a genome-wide catalogue of base substitution signatures which are present in the DNA sample;
  (ii) a genome-wide catalogue of insertion/deletion signatures which are present in the DNA sample;
  (iii) a genome-wide copy number profile in the DNA sample; and
  (iv) putative driver mutations present in the DNA sample;

c) constructing, by said processor, the interpreted profile from the determining steps (a) and (b), the interpreted profile including the two or more items determined in step (b) and identifying the presence of the one or more rearrangement signatures thereby indicating mutational processes in the breast cancer tumour that cause the breast cancer tumour to respond to the cancer therapy;

d) determining, using the interpreted profile, a score indicating a likelihood that the DNA sample is homologous recombination (HR) deficient, wherein determining the score is performed using two or more of the following steps i) through iv):
  i) determining the presence or absence of at least one base substitution signature in the DNA sample;
  ii) determining the presence or absence of at least one rearrangement signature in the DNA sample;
  iii) determining the presence or absence of at least one insertion/deletion signature in the DNA sample; and
  iv) determining a copy number profile for the DNA sample; and (e) determining that the score indicating the likelihood that the DNA sample is homologous recombination (HR) deficient exceeds a second predetermined threshold; and (f) after it is determined that the score indicating the likelihood that the DNA sample is HR deficient exceeds the second predetermined threshold, administering the cisplatin and/or the PARP inhibitor to the patient as the cancer therapy.

2. The method according to claim 1, further comprising the steps of:

e) identifying putative recurrently mutated non-coding sites from the whole-genome sequencing data from the DNA sample, and using the identified putative recurrently mutated non-coding sites in constructing the interpreted profile, and/or f) obtaining the genome-wide catalogue of the base substitution signatures by:
  i) cataloguing somatic mutations in said DNA sample to produce a mutational catalogue for the DNA sample,
  ii) determining the contributions of a plurality of mutational signatures to said mutational catalogue by determining a scalar factor for each of said plurality of mutational signatures which together minimize a function representing the difference between: (1) the mutations in said mutational catalogue and (2) the mutations expected from a combination of said plurality of mutational signatures scaled by said scalar factors, and
  iii) if the scalar factor corresponding to any one of said mutational signatures exceeds a predetermined threshold, including said mutation signature in the genome-wide catalogue of base substitution signatures for the sample;

and/or g) obtaining the catalogue of one or more rearrangement signatures present in the DNA sample by:
  i) cataloguing somatic mutations in said DNA sample to produce the rearrangement catalogue for the DNA sample which classifies identified rearrangements in the DNA sample into the plurality of categories,
  ii) determining the contributions of a plurality of rearrangement signatures to said rearrangement catalogue by computing a cosine similarity between the identified rearrangements in said rearrangement catalogue and the plurality of rearrangement signatures, and
  iii) identifying a rearrangement signature present in the sample, wherein the number or proportion of rearrangements in the rearrangement catalogue which are determined to be associated with the rearrangement signature of said plurality of rearrangement signatures that is identified to be present in the sample exceeds a predetermined threshold;

and/or wherein determining putative driver mutations present in the DNA sample comprises determining whether one or more breast cancer genes are present or not, wherein the one or more breast cancer genes are selected from: TP53, PK3CA, MYC, CCND1, PTEN, ERBB2, Chr8(ZNF703/FGFR1), GATA3, RB1, MAP3K1, MAP2K4, ZNF217, CDH1, MLL3, ARID1B, CDKN2A, MLLT4, AKT1, FBXW7, ARID1A, CCND3, CBFB, MDM2, CCNE1, CDKN2B, NCOR1, SF3B1,SPEN, TBX3, IGF1R, BRCA2, NF1, PIK3R1, EGFR, KRAS, ESR1, FOXA1, MED23, CDK6, NOTCH2, AKT2, BRCA1, CTCF, KDM6A, SETD2, CREBBP, DNMT3A, FOXP1, MLL2, RUNX1, USP9X, XBP1, PDGFRA, ATR, ERBB3, FGFR2, PALB2, RHOA, SMAD4, ATM, ATRX, AXIN1, BCOR, CDKN1B, CUX1, GNAS, MLH1, NOTCH1, PHF6, SMARCA4, STAG2, ZFP36L1, APC, CASP8, CBLB, CNOT3,ECT2L, MEN1, MSH2, NRAS, PBRM1, PMS2, STK11, TET2, ASXL1, BRAF, BUB1B, CIC, ERCC4, HRAS, NF2, PRDM1, and PREX2.

3. The method according to claim 1, further including the steps of:

identifying the presence of mis-match repair (MMR) deficiency in the DNA sample by using the presence or absence of the at least one base substitution signature in the DNA sample and the at least one insertion/deletion signature in the DNA sample, and using this identification in constructing the interpreted profile.

4. The method of claim 1, further comprising:

a) classifying a plurality of patients undergoing treatment for cancer, or participating in a clinical trial, the method comprising allocating patients to groups based on an interpreted profile constructed from a DNA sample obtained from a breast cancer tumour in each patient by the method of claim 1; and/or b) selecting a patient for a clinical trial of a cancer therapy comprising characterising a DNA sample obtained from a breast cancer tumour in said patient using the method according to claim 1;
and determining whether or not the patient is suitable for the clinical trial on the basis of the interpreted profile constructed for that patient; and/or
c) classifying patients who have completed a clinical trial or course of treatment comprising characterising a DNA sample obtained from a breast cancer tumour in each of said patients by the method of claim 1; and correlating an interpreted profile obtained for each patient with a clinical outcome of the trial or treatment; and/or
d) determining a prognosis of a breast cancer tumour comprising characterising a DNA sample obtained from said breast cancer tumour using the method of claim 1, thereby constructing a corresponding interpreted profile; and determining the prognosis from the corresponding interpreted profile.

5. The method of claim 1, wherein steps a) and b) are performed using whole genome-sequencing data from massively parallel sequencing.

6. The method of claim 5, wherein the DNA sample from the patient is a biopsy and/or wherein the method further comprises massively parallel sequencing of a normal, non-tumor sample from the patient.

7. The method of claim 1, further comprising:
obtaining the whole-genome sequencing data by performing massively parallel sequencing of the sample.

8. The method of claim 1, wherein determining, using the interpreted profile, the score indicating the likelihood that the DNA sample is homologous recombination (HR) deficient comprises determining the score using all of the following steps i) through iv):
   i) determining the presence or absence of at least one base substitution signature in the DNA sample;
   ii) determining the presence or absence of at least one rearrangement signature in the DNA sample;
   iii) determining the presence or absence of at least one insertion/deletion signature in the DNA sample; and
   iv) determining a copy number profile for the DNA sample.

9. The method of claim 1, wherein determining the presence or absence of at least one base substitution signature in the DNA sample comprises determining the presence or absence of at least two types of base substitution signatures signature in the DNA sample.

10. The method of claim 1, wherein determining the presence or absence of at least one rearrangement signature in the DNA sample comprises determining the presence or absence of a first rearrangement signature characterized by the presence of non-clustered deletions less than 100 kb in length, a second rearrangement signature characterized by the presence of non-clustered tandem duplications less than 10 kb in length, or both in the DNA sample.

11. The method of claim 1, wherein determining the presence or absence of at least one insertion/deletion signature in the DNA sample comprises determining the presence or absence of a microhomology-mediated insertions/deletion signature in the DNA sample.

12. The method of claim 1, wherein determining the copy number profile for the DNA sample comprises determining a homologous recombination (HR) deficient copy number-based index for the DNA sample.

13. A method of treating a patient having breast cancer by constructing an interpreted profile of a DNA sample obtained from a breast cancer tumour of the patient and using the interpreted profile to determine whether to administer cisplatin and/or a PARP inhibitor to the patient as a cancer therapy, the method comprising:
   a) determining, by a processor, from whole-genome sequencing data from said DNA sample a catalogue of one or more rearrangement signatures which are present in the DNA sample by:
      (i) classifying each rearrangement in the DNA sample in one of a plurality of categories, the one of the plurality of categories selected from the group consisting of a category of two or more categories of clustered deletions that differ by their size, a category of two or more categories of non-clustered deletions that differ by their size, a category of two or more categories of clustered inversions that differ by their size, a category of two or more categories of non-clustered inversions that differ by their size, a category of clustered translocations, a category of non-clustered translocations, a category of two or more categories of clustered tandem duplications that differ by their size, and a category of two or more categories of non-clustered tandem duplications that differ by their size, thereby obtaining a rearrangement catalogue for said DNA sample, wherein the rearrangement catalogue comprises a number of rearrangements in said DNA sample classified in each of said plurality of categories; and
      (ii) identifying one or more rearrangement signatures present in the DNA sample, wherein the one or more rearrangement signatures comprise defined patterns of rearrangements as classified between the plurality of categories;
   b) determining, by said processor, from the whole-genome sequencing data from said DNA sample three or more items among:
      (i) a catalogue of base substitution signatures which are present in the DNA sample;
      (ii) a catalogue of rearrangement signatures which are preset in the DNA sample;
      (iii) a catalogue of insertion/deletion signatures which are present in the DNA sample;
      (iv) a genome-wide copy number profile in the DNA sample; and
      (v) putative driver mutations present in the DNA sample;
   c) constructing, by said processor, the interpreted profile from the determining steps (a) and (b), the interpreted profile including the three or more items determined in step (b) and identifying the presence of the one or more rearrangement signatures thereby indicating mutational processes in the breast cancer tumour that cause the breast cancer tumour to respond to the cancer therapy;
   d) determining, using the interpreted profile, a score indicating a likelihood that the DNA sample is homologous recombination (HR) deficient, wherein determining the score is performed using two or more of the following steps i) through iv):
      i) determining the presence or absence of at least one base substitution signature in the DNA sample;
      ii) determining the presence or absence of at least one rearrangement signature in the DNA sample;
      iii) determining the presence or absence of at least one insertion/deletion signature in the DNA sample; and
      iv) determining a copy number profile for the DNA sample; and (e) determining that the score indicating the likelihood that the DNA sample is homologous recombination (HR) deficient exceeds a predetermined threshold; and (f) after it is determined that the score indicating the likelihood that the DNA sample is HR deficient exceeds the predetermined threshold, administering the cisplatin and/or the PARP inhibitor to the patient as the cancer therapy.

* * * * *